United States Patent [19]
Jazwinski

[11] Patent Number: 5,817,782
[45] Date of Patent: Oct. 6, 1998

[54] LAG 1:GENE FOR INCREASING THE LONGEVITY OF EUKARYOTES

[75] Inventor: S. Michal Jazwinski, New Orleans, La.

[73] Assignee: Research Corporation Technologies, Inc., Tucson, Ariz.

[21] Appl. No.: 336,031

[22] Filed: Nov. 8, 1994

Related U.S. Application Data

[63] Continuation-in-part of Ser. No. 253,875, Jun. 3, 1994, abandoned.

[51] Int. Cl.$^6$ .......................... C07H 21/02; C07H 21/04; C12Q 1/68; C12P 19/34
[52] U.S. Cl. .................... 536/23.1; 536/24.3; 536/24.32; 435/69.1; 435/172.3; 435/6; 435/5; 435/254.2; 435/254.3; 435/91.2; 435/91.1; 435/240.2
[58] Field of Search ................................ 435/69.1, 172.3, 435/6, 5, 254.2, 252.3, 91.1, 91.2; 536/23.1, 24.3, 24.32; 514/2

[56] References Cited

PUBLICATIONS

Baixeras et al. Mol. Immunol 27: 1091–1102 (Cited in 08253875), 1990.
Davis et al. JBC 267: 5508–5514 (Cited in 08253875), 1992.
Davis et al. Characterization of a Yeast Mitochondrial Ribosomal Protein Structurally Related to the Mammalian 68–kDa High Affinity Laminin Receptor Journal of Biological Chemistry 267(8): 5508–5514, 1992.
D/mello et al. Cloning and Characterization of LAG1, a Longevity–assurance Gene in Yeast.The Journal of Biological Chemistry 269: 15451–15459, 1994.
Jazwinski, S The genetics of aging in the yeast *Saccharomyces cerevisiae*. Genetica 91: 35–51, 1993.
Jazwinski, S. Genes of Youth: Genetics of Aging in Baker's Yeast. ASM News 59 (4): 172–178, 1993.
N.P. D'Mello et al., (1993), "Functional Characterization of a Longevity Assurance Gene (LAG1) in Yeast," *Mol. Biol. of Aging*, 0308:159.
N.P. D'Mello et al., (1992), "Molecular Analysis of a Young–Specific Gene in the Yeast *Saccharomyces cerevisiae*," *Abstracts of the General Meeting*, H–284:230.
N.K. Egilmez et al., (1989), "Evidence for the Involvement of a Cytoplasmic Factor in the Aging of the Yeast *Saccharomyces cerevisiae*," *J. Bacteriology*, 171(1):37–42.
N.K. Egilmez et al., (1989), "Specific Alterations in Transcript Prevalence During the Yeast Life Span," *J. Biol. Chem.*, 264(24):14312–14317.
S.M. Jazwinski, (1990), "Aging and Senescence of the Budding Yeast *Saccharomyces cerevisiae*," *Mol. Microbiol.*, 4(3):337–343.
S.M. Jazwinski, (1990), "An Experimental System for the Molecular Analysis of the Aging Process: The Budding Yeast *Saccharomyces cerevisiae*," *J. Gerontology*, 45(1):B68–B74.
Johnston, et al. Complete Nucleotide Sequence of *Saccharomyces Cerevisiae* Chromosome VIII. Science 265: 2077–2082, 1994.

*Primary Examiner*—W. Gary Jones
*Assistant Examiner*—Dianne Rees
*Attorney, Agent, or Firm*—Scully, Scott, Murphy & Presser

[57] ABSTRACT

The present invention provides a unique eukaryotic gene, called LAG1, which controls the longevity of eukaryotic cells. According to the present invention, overexpression of LAG1 in older cells has a rejuvenating effect which not only increases cellular life span but also reproductive capacity and cellular tolerance to stress factors such as starvation and low pH. Moreover, the present invention identifies two domains in LAG1 one having a life span limiting function and the other a life span extending function. Hence, according to the present invention, the longevity and tolerance to stress of cells is increased when provided with the wild type polypeptide or mutant LAG1 polypeptides which, for example, lack the "life span limiting domain."

21 Claims, 18 Drawing Sheets

```
 589 AGTGATTTGTGGTTGTTCAAGACAAAACCAATGTACAGAACATATCCTGTTATAACCAATCCGTTCTTGTTAAGATATTTTAC  224
     SerAspLeuTrpLeuPheLysThrLysProMetTyrArgThrTyrProValIleThrAsnProPheLeuLysIlePheTyr
 673 TTGGGTCAAGCGGCATTTGGGCGCAACAGGCTTGTTGTTCTTGTTCTACAATTAGAAAAGCCAAGAATTACAAGGAATTG  252
     LeuGlyGlnAlaAlaPheTrpAlaGlnAlaCysValLeuValLeuGlnLeuGluLysProArgLysProArgLysGluLeu
 757 GTTTTCATCACATTGTGACATTATTATTGGTCATCATATGTTTCATTTTACCAAATGGATTGGCTATCTATATT  280
     ValPheHisHisIleValThrLeuLeuLeuIleTrpSerSerTyrValPheHisPheThrLysMetGlyLeuAlaIleTyrIle
 841 ACTATGATGTGTCAGATTTTTCCTTCTTGTAAGACATTAAACTATCTGAATTCTGTATTACTCCCTTTGTTCGGC  308
     ThrMetAspValSerAspPhePheLeuSerLeuSerPheLeuArgHisValPhePheThrProPheValPheGly
 925 TTGTTCGTGTTCTTTTGGATCTATCTGCGCCATGTCGTGAATATCAGAATATTATTGGTCAGTCTTAACAGAATTCCGTCATGAA  336
     LeuPheValPhePheTrpIleTyrLeuArgHisValValAsnIleArgIleLeuTrpSerValLeuThrGluPheArgHisGlu
1009 GGTAATTATGTGTTGAATTTTGCCACACAACAATACAAATGTTGGATTTGTTGCCAATTGTATTGTTGTACTAATTGTGCGTTA  364
     GlyAsnTyrValLeuAsnPheAlaThrGlnTyrLysCysTrpIleSerLeuProIleValPheValLeuIleAlaAlaLeu
1093 CAATTAGTTAACCTGTATTGGCTGTTTTAATTCTTAGAATCTTGTACAGATTGATATGGCAAGGTATCCAAAAGGACGAAAGA  392
     GlnLeuValAsnLeuTyrTrpLeuPheLeuIleLeuArgIleLeuTyrArgLeuIleLeuTrpGlnGlyIleGlnLysAspGluArg
1177 AGTGACAGTGATTCTGATGAGAGGCTGAAAATGAAGAATCTAAGGAAAAGTGTGAATAAACGTATCTTAAGGAGAATACGTAT
     SerAspSerAspSerAspGluSerAlaGluAsnGlyGluSerLysGlyLysCysGlu***
1261 CATCATATGATTCCCCCCTGTATGAAGGCCAAGTTAACATGGTATAGCTCATAGTTGTTGTTATAAGAAGCATAAACCCAAGT
1345 ACGAAAGTAATAATTCTGTAAAAAAAAAAAATGCGTTTATTTAGGCGTCTTCGGGTTGGCTATATATATATTTAAGGATAT
1429 ATGGGCATATGTACAAGTTTAGGTTAACAAGCCAAAAGAAAATAAAAGTGT
```

LAG 1:GENE FOR INCREASING THE LONGEVITY OF EUKARYOTES

CROSS-REFERENCE TO RELATED APPLICATIONS

This invention is a continuation-in-part application of U.S. Ser. No. 08/253,875, which was filed on Jun. 3, 1994 (now abandoned).

This invention was made with United States Government support under Grant No. AG06168 awarded by the National Institutes of Health. The United States Government may have certain rights in the invention.

BACKGROUND OF THE INVENTION

1. Field of the Invention

The present invention provides a gene, LAG1, which controls longevity and cellular tolerance to stress in eukaryotes. The present invention is, therefore, directed to LAG1 nucleic acids and the polypeptides encoded and expressed thereby, including appropriate vectors and host cells. The present invention contemplates antisense RNA and DNA. This invention further provides methods for increasing the longevity and the tolerance to stress, especially starvation and low pH, of eukaryotic cells by providing to the cell mutant or wild type LAG1 polypeptides. According to the present invention, mutant LAG1 polypeptides which lack a "life-span limiting domain" are particularly effective for increasing cellular longevity and cellular tolerance to stress. Methods for providing the cell with such LAG1 polypeptides include overexpressing the endogenous LAG1 gene, mutating the endogenous LAG1 gene or providing the cell with an expression vector containing the appropriate mutant or wild type LAG1 coding region. Such methods can be practiced, for example, in yeast and mammalian cells. The present invention is also directed to pharmaceutical compositions to effect such methods. Moreover, these methods have particular application in the yeast fermentation industry.

2. Discussion of the Prior Art

Aging is genetically determined as evidenced by the differing life spans of different species and by recent genetic studies. In *Saccharomyces cerevisiae*, controlled expression of the v-Ha-ras gene leads to a near doubling of life span (Chen et al. 1990 *Mol. Microbiol.* 4: 2081–86). In *Caenorhabditis elegans*, inbred recombinant and mutant strains have been generated which have an increased mean and maximum life span (Johnson 1987 *Proc. Natl. Acad. Sci. USA* 84: 3777–81; Friedman et al. 1988 *Genetics* 18: 75–86). Seletive breeding of *Drosophila melanogaster* has yielded long-lived strains (Rose 1984 *Evolution* 38: 1004–1010; Luckinbill et al. 1984 *Evolution* 38: 996–1003). The operation of a "senescence factor" which can limit replicative capacity has been discovered in both human fibroblasts and yeast (Lumpkin et al. 1986 *Science* 232: 393–95 and Egilmez et al. 1989 *J. Bacteriol.* 171: 37–42, respectively). Differential hybridization procedures have been used to screen for genes that are preferentially expressed in young or old cells as described in Egilmez et al. (1989 J. Biol. Chem. 264: 14312–17). For review of the genetic control of senescence, see, for example, Jazwinski (1990, Molec. Microbiol. 4: 33–343); Jazwinski (1990 J. Gerontol. 45: B68–B73); and Jazwinski (1993 Genetica 91:35–51).

The present invention provides a unique eukaryotic gene, called LAG1, which controls the longevity of eukaryotic cells. According to the present invention, overexpression of LAG1 in older cells has a rejuvenating effect which not only increases cellular life span but also reproductive capacity and cellular tolerance to stress factors such as starvation and low pH. Moreover, the present invention identifies two domains in LAG1 one having a life span limiting function and the other a life span extending function. Hence, according to the present invention, the longevity and tolerance to stress of cells is increased when provided with the wild type polypeptide or mutant LAG1 polypeptides which, for example, lack the "life span limiting domain."

While LAG1 has a general utility for increasing cellular longevity and tolerance to stress, the present invention also contemplates a particular utility for LAG1 in the yeast fermentation industry. Yeast are employed in a variety of ways to produce a wide range of beverages and food products, including for example, the production of alcoholic beverages, baked goods, single-cell protein and for the production of proteins and enzymes. However, during fermentation yeast can be subjected to stressful conditions such as low pH and starvation. See, for example, Y. H. Hui, ed., *Encyclopedia of Food Science and Technology*, Vols. 1–4 (John Wiley & Sons, Inc., New York, 1992). The present invention provides yeast strains which not only have greater longevity but are resistant to stressful conditions and have an increased reproductive capacity.

SUMMARY OF THE INVENTION

The present invention is directed to isolated nucleic acids encoding LAG1 polypeptides which increase the longevity and tolerance to cellular stress of eukayotic cells. Preferred nucleic acids include:

(a) nucleic acids having SEQ ID NO:1, SEQ ID NO:3 or SEQ ID NO:5;

(b) nucleic acids having the insert in pDF5 given ATCC No. 75790;

(c) nucleic acids capable of hybridizing to a DNA having SEQ ID NO:1 under moderate to stringent conditions;

(d) nucleic acids differing from any one of the nucleic acids of (a), (b) or (c) in codon sequence due to the degeneracy of the genetic code;

(e) nucleic acids encoding various species of LAG1 polypeptides such as, for example, yeast, mammals including human, bovine, murine; Podospora, galago, and salmon.

The present LAG1 nucleic acids preferably have at least 50% homology to SEQ ID NO:1, SEQ ID NO:3 or SEQ ID NO:5.

In another embodiment, the present invention provides LAG1 polypeptides, i.e. isolated or synthesized polypeptides or derivatives thereof which increase the longevity and tolerance to cellular stress of eukaryotic cells, including e.g. Podospora, mammalian including human, bovine and mouse; galago, salmon and the like. In one embodiment the present invention is drawn to an isolated *S. cerevisiae* LAG1 polypeptide having, for example, SEQ ID NO:2, SEQ ID NO:4 or SEQ ID NO:6. Preferably, these polypeptides have at least about 25% to 30% homology to SEQ ID NO:2, SEQ ID NO:4 or SEQ ID NO:6.

The present invention is also directed to an isolated LAG1 antisense RNA or DNA having sufficient length and sufficient complementarity to selectively hybridize to a nucleic acid having SEQ ID NO:1. In another embodiment the antisense RNA or DNA has sufficient length and sufficient complementarity to selectively hybridize to a nucleic acid having SEQ ID NO:7, especially a transcriptional regulatory region within SEQ ID NO:7. For example, such a transcriptional regulatory region can be a binding site for GCN4 protein or regulatory complex 2 (RC2). Preferably, such antisense nucleic acids have at least 50% complementarity to the non-template strand of SEQ ID NO:1 or to either strand of SEQ ID NO:7. The length of an antisense RNA and DNA is at least about 14 to about 17 nucleotides.

In a further embodiment the present invention provides isolated replication and expression vectors containing the present LAG1 nucleic acids as well as host cells for these vectors.

Another embodiment of the present invention provides a method for increasing the longevity, reproductive capacity and/or tolerance to stress of a eukaryotic cell. Such methods include administering mutant or wild type LAG1 polypeptides to the cell of interest. According to the present invention, the administration of wild type or mutant LAG1 polypeptides which lack the "life span limiting domain" increases cellular longevity, reproductive capacity and cellular tolerance to stress, e.g. starvation or acidic pH.

A further embodiment of the present invention provides a method for increasing the longevity, reproductive capacity, tolerance to starvation or tolerance to acidic pH of a eukaryotic cell which includes expressing a mutant or wild type LAG1 polypeptide in the cell. Preferably, a mutant LAG1 which lacks the life span limiting domain is expressed.

In a further embodiment, the present invention provides pharmaceutical compositions containing at least one of the present LAG1 nucleic acids, oligonucleotides or polypeptides, and a pharmaceutically acceptable carrier. As contemplated by the present invention, these LAG1 nucleic acids, oligonucleotides or polypeptides include, for example, yeast, Podospora, human, bovine, mouse, galago, salmon and related eukaryotic nucleic acids, oligonucleotides or polypeptides. Preferred compositions include LAG1 nucleic acids having at least 50% homology to SEQ ID NO:1, SEQ ID NO:3, SEQ ID NO:5 or SEQ ID NO:7. Preferred compositions also include polypeptides having at least about 25% to 30% homology to of SEQ ID NO:2, SEQ ID NO:4 or SEQ ID NO:6.

BRIEF DESCRIPTION OF THE DRAWINGS

FIG. 2 depicts the DNA and deduced protein sequences of the Saccharomyces cerevisiae LAG1 gene. Nucleotides are numbered at the left beginning with the A of the predicted translation initiation codon. Amino acid residues are numbered at the right. The asterisks indicate the termination codon. Transcriptional initiation sites (-127 and -135) are underlined.

THR1 and CDC12 segregated to give PD=5, NPD=5, and T=23. The genetic distance in centimorgans (cM) was calculated from the following equation:

$$cM=(1002)[(T+6NPD)/(PD+NPD+T)].$$

The solid oval at the left indicates the centromere.

Figure 9:
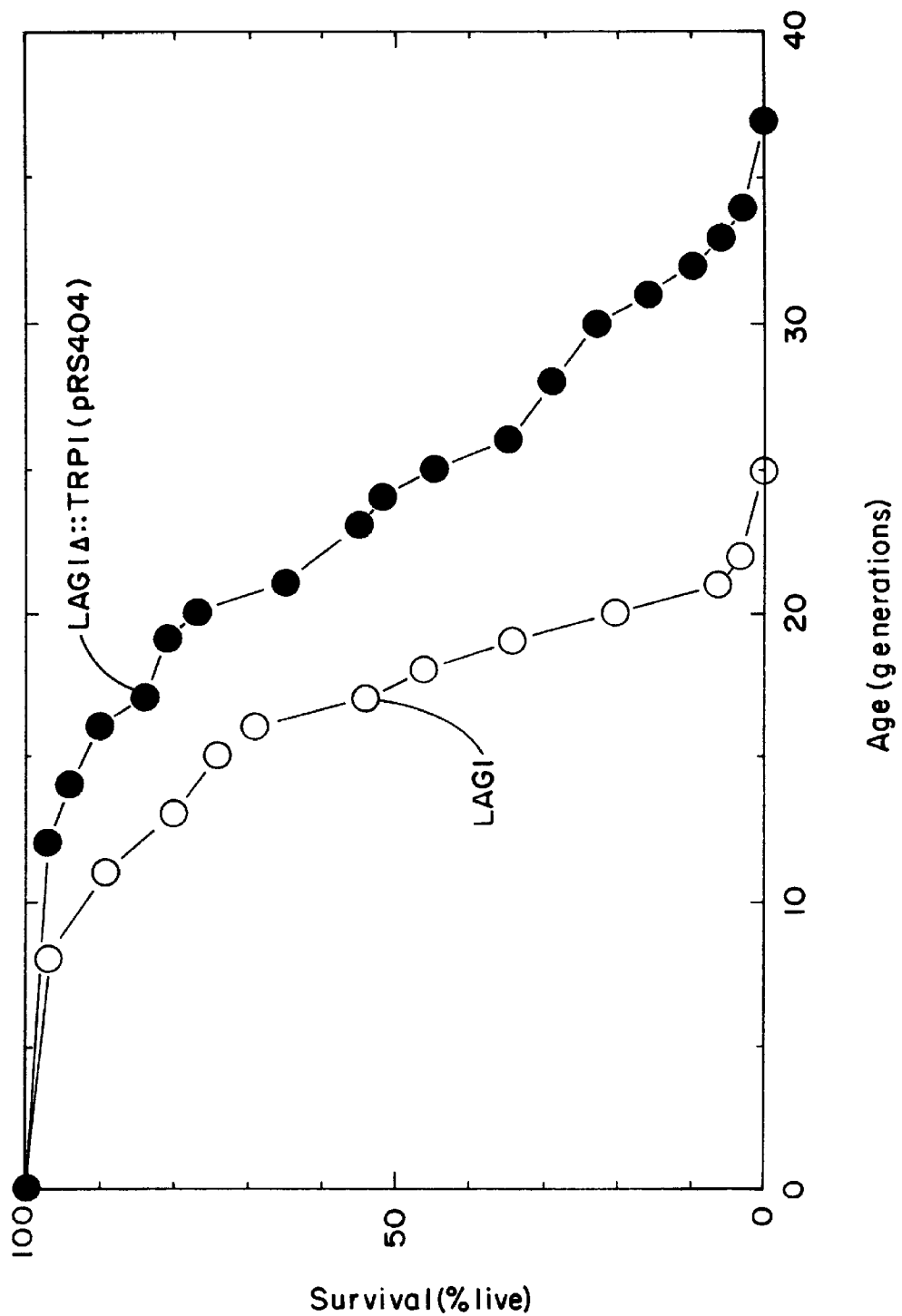

FIG. 9 depicts the life span of yeast cells having a deleted LAG1. The mean life span of cells with the LAG1 deletion was 25 generations, whereas the mean life span of cells with the intact, wild-type gene was 17 generations (p<<0.0001). Corresponding maximum life spans were 37 and 25 generations.

Figure 10A:
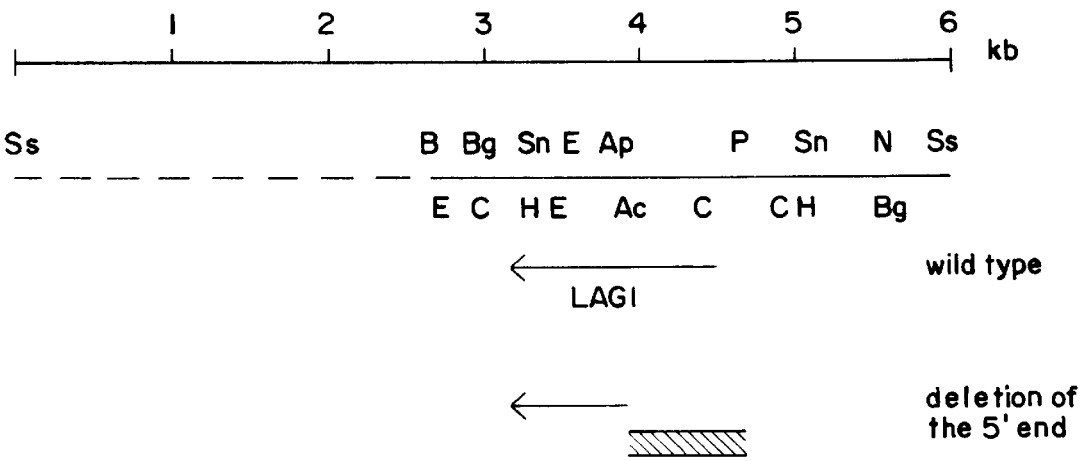

FIG. 10A depicts a genetic deletion performed on *S. cerevisiae* LAG1 in relation to the 6 kb SstI fragment restriction map. The arrows indicate the length of the transcript and direction of transcription. The 5' region of the LAG1 gene that was deleted is indicated by a hatched box. Restriction sites (Ap=ApaI, Ac=AccI, B=BamHI, Bg=BglII, Ss=SstI, Sn=SnaBI, P=PstI, N=NcoI, H=HpaI, C=ClaI, E=EcoRI) are indicated by vertical lines. The scale is in kilobases.

Figures 10B, 10C:
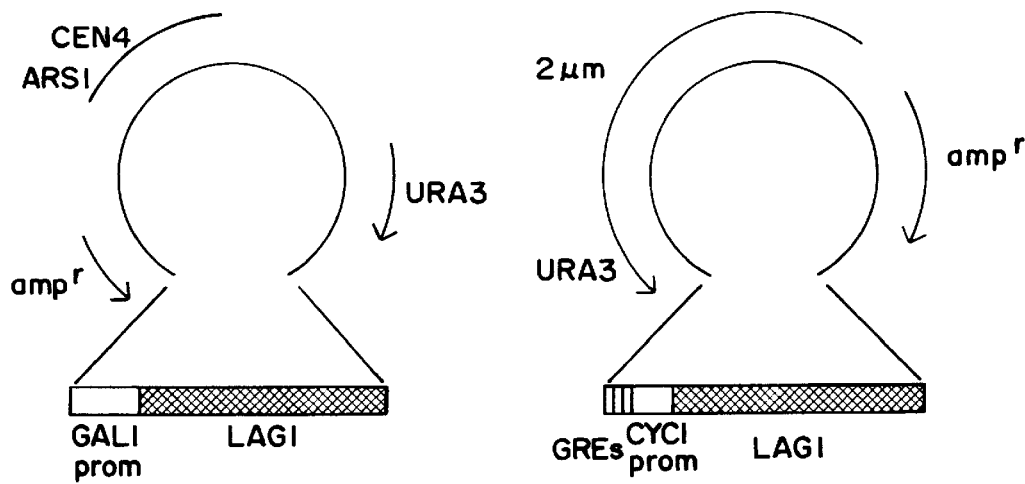

FIG. 10B depicts the construction of an expression vector permitting high levels of LAG1 overexpression. A 2-kb fragment spanning the coding region of the LAG1 gene was inserted in the BamHI site in the vector pBM150, downstream of the galactose-inducible GAL1 promoter.

FIG. 10C depicts the construction of an expression vector permitting low levels of LAG1 overexpression. A 2 kb LAG1 BamHI fragment was inserted in the BamHI site located downstream of the CYC1 promoter and glucocorticoid response elements (GREs) present in the vector 2UG. Cells were transformed with the plasmid 2UG containing the LAG1 gene and the plasmid G-N795 carrying the gene coding for the glucocorticoid receptor downstream of the constitutive GPD promoter. Expression of the LAG1 gene was induced by addition of deoxycorticosterone to the growth medium.

Figure 11:
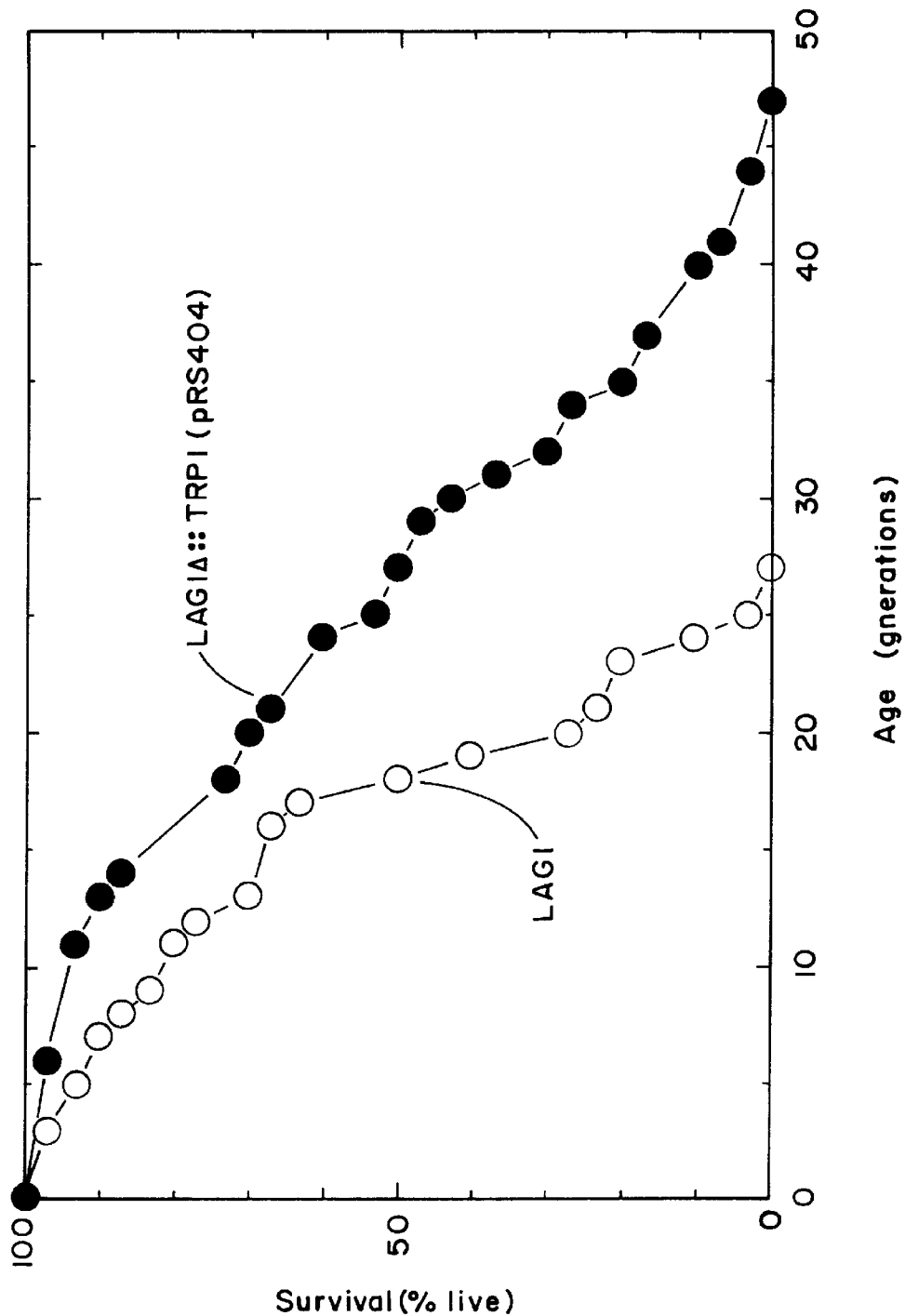

FIG. 11 depicts the increase in life span of cells with a deletion of the 5' end of the LAG1 gene (LAG1Δ::TRP1 (pRS404),●) relative to wild type (LAG1, ○). Life spans of individual cells were determined on YPD medium. The mean life span of cells with the LAG1 5' deletion was 27 generations, whereas the mean life span of wild type cells was 17 generations (p<0.0001). Corresponding maximum life spans were 47 and 27 generations, respectively. The presence of TRP1 had no significant effect on life span.

Figure 12:
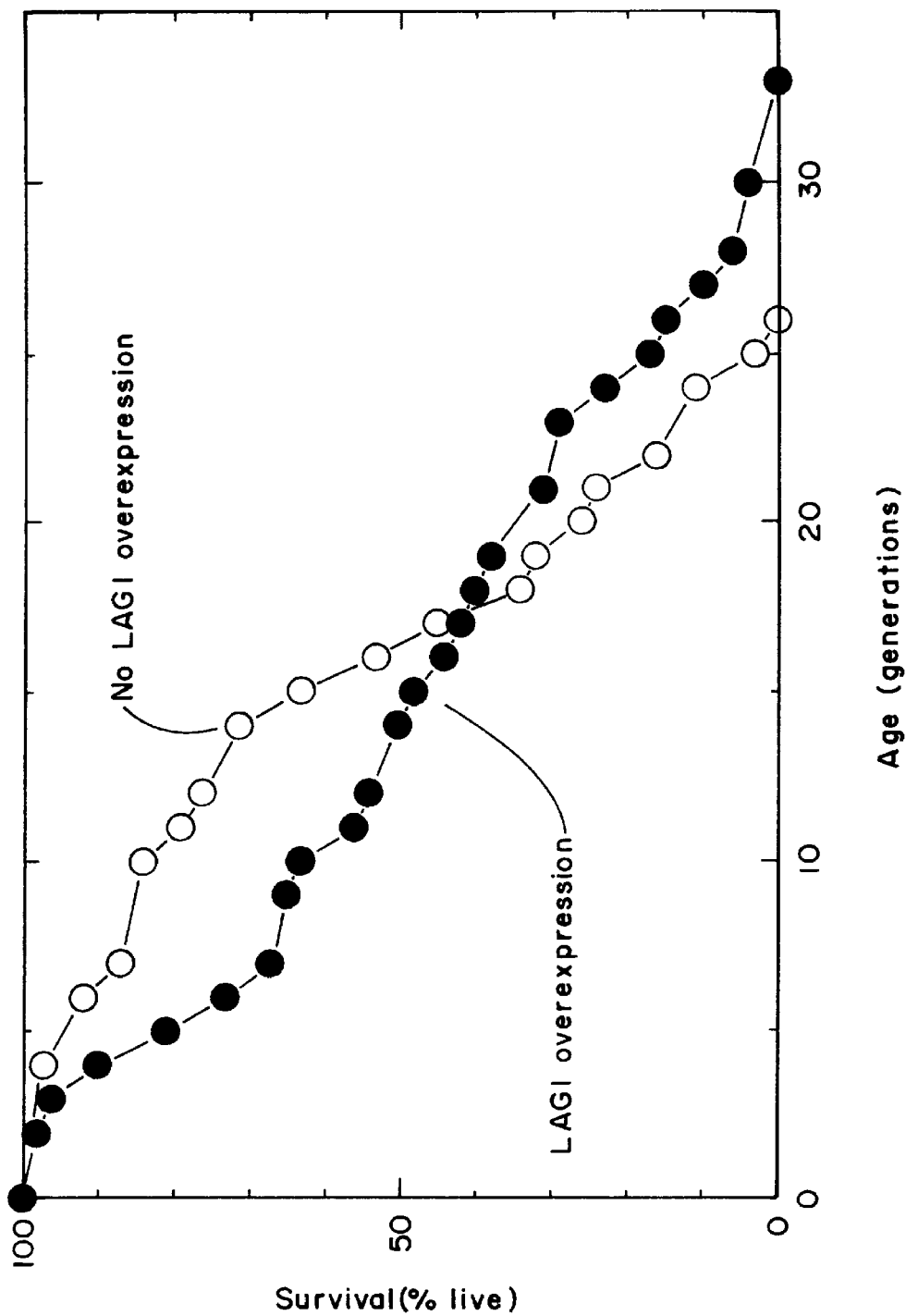

FIG. 12 depicts the life span of cells overexpressing the LAG1 gene from the GAL1 promoter (●), as compared to wild type (○). Life spans of the cells were determined on synthetic medium lacking uracil to select for cells with the plasmid and in the presence of galactose to induce expression of the gene or glucose to repress it. The mean life span of cells that survived the increase in initial mortality due to overexpression of the gene was 24 generations, and the maximum was 33 generations. The mean and maximum life span of cells in which the gene was repressed by glucose was 21 generations (p<0.005) and 26 generations, respectively. The crossover point of the two curves at about 17 generations was nominally taken to demarcate cells that survived the increase in initial mortality.

Figure 13A:
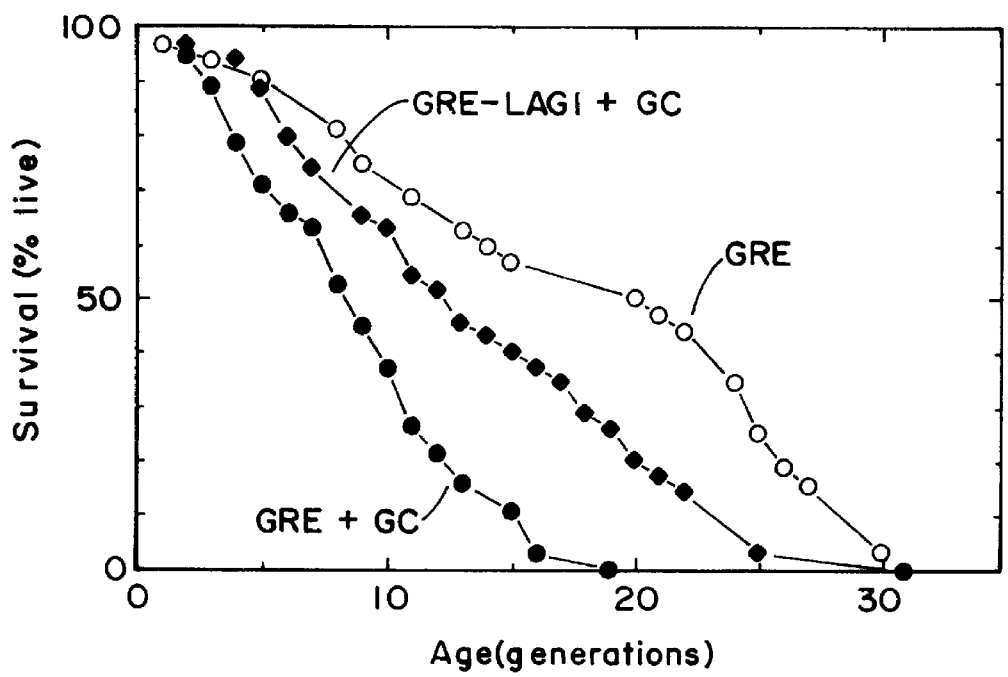

FIG. 13A depicts the life span of cells overexpressing LAG1 from the GRE promoter. Expression of LAG1 was induced by 10 μM deoxycorticosterone (GC) present in the medium from the inception of the experiment (GRE-LAG1+GC, ♦). Control cells had the 2UG plasmid without LAG1 and the G-N795 plasmid (GRE). The life spans of control GRE cells was observed with (GRE+GC, ●) and without (GRE, ○) deoxycorticosterone. Cells expressing LAG1 (♦) had a mean life span of 14 generations, as compared to a life span of 9 generations for cells not expressing LAG1 (●) which were also exposed to deoxycorticosterone (p<0.0005). The corresponding maximum life spans were 31 and 19 generations, respectively.

Figure 13B:
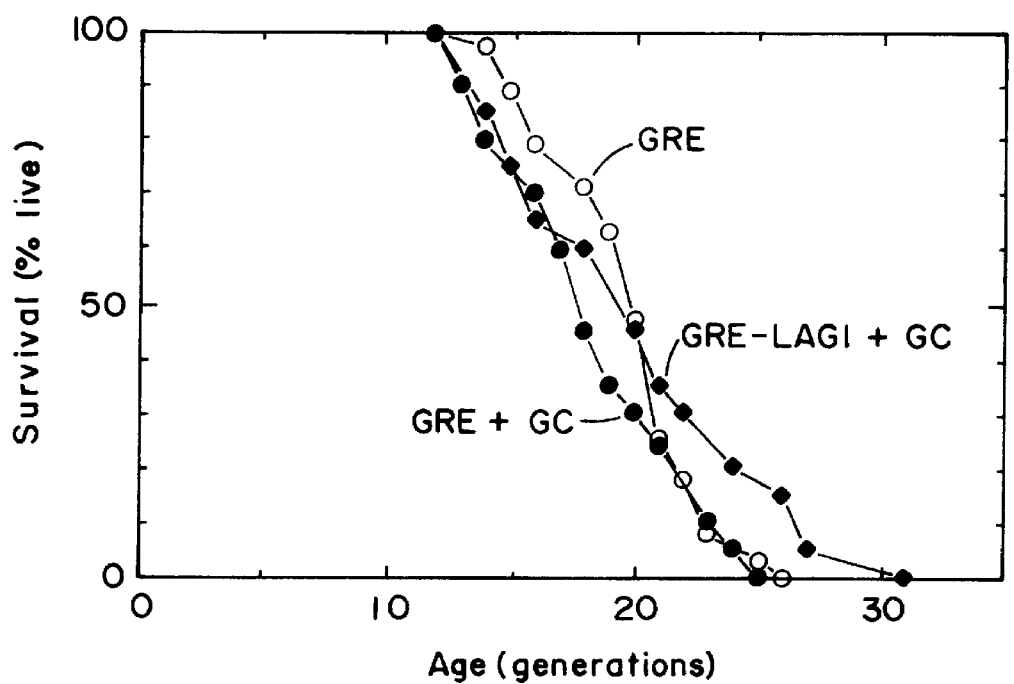

FIG. 13B depicts the life span of cells in which LAG1 expression was induced by deoxycorticosterone after 12 generations (GRE-LAG1+GC, ♦). Control cells again had the 2UG plasmid without LAG1 and the G-N795 plasmid (GRE). The life spans of control GRE cells was observed with (GRE+GC, ●) and without (GRE, ○) deoxycorticosterone addition after 12 generations. The mean life span of cells expressing LAG1 (♦) was 24 generations, as compared to 21 generations for cells with no overexpression of LAG1 (○), (p<0.01). The corresponding maximum life spans were 31 and 26 generations, respectively. The crossover point at about 20 generations of the cells overexpressing LAG1 (GRE-LAG1+GC, ♦) and those with no LAG1 overexpression (GRE, ○) was nominally taken to demarcate cells displaying extended longevity which had survived the initial increase in mortality.

Figure 14:
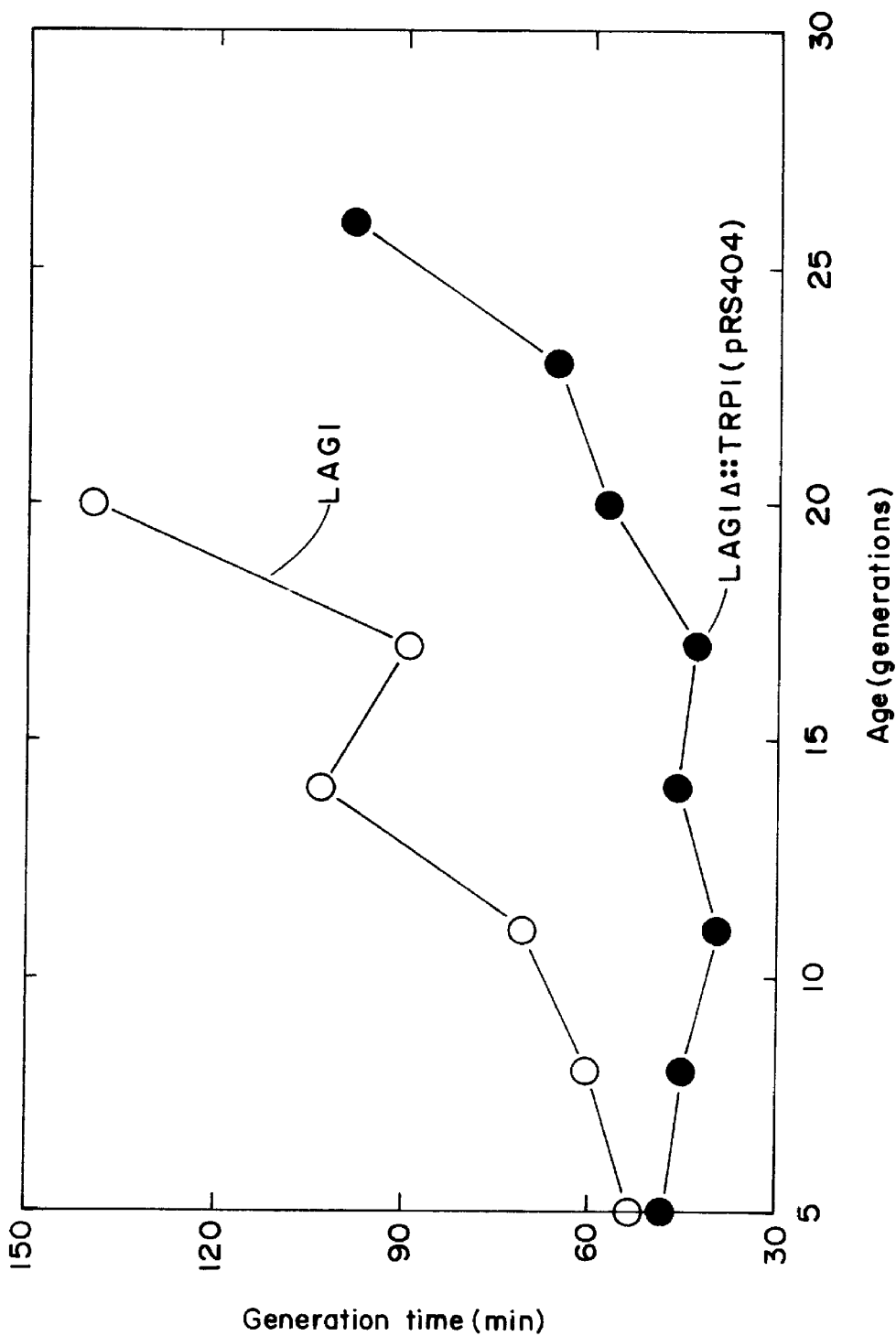

FIG. 14 depicts the effect of a 5' end deletion of LAG1 on generation time, illustrating that the LAG1 extension of life span postpones yeast senescence. The generation time, as measured by the interval between consecutive buddings, for mutant cells having a 5'-deletion in LAG1 (LAG1Δ::TRP1, ●) was compared with wild type cells (LAG1, ○) throughout the cellular life span. The mean values of generation times are graphed.

Figure 15:
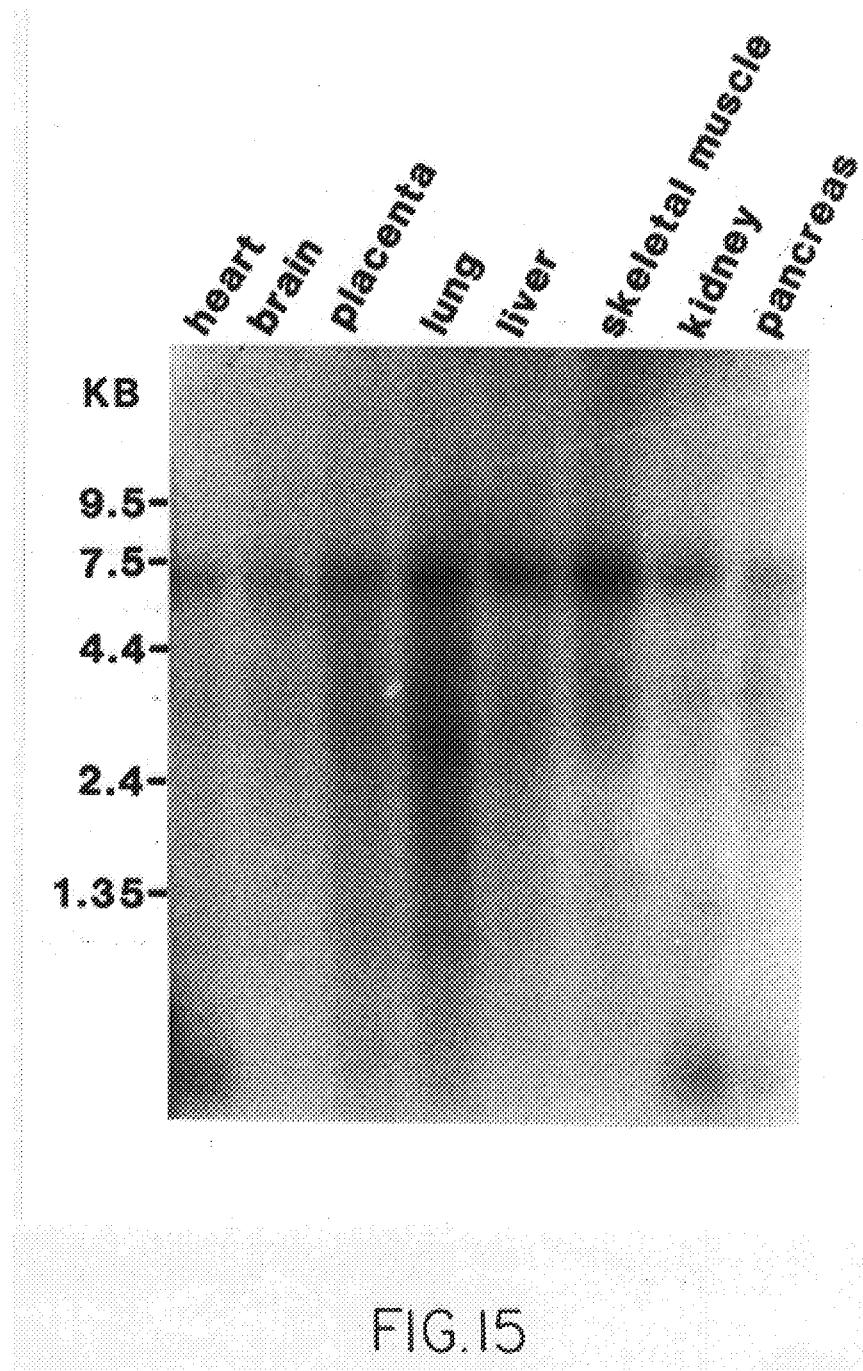

FIG. 15 depicts hybridization of a *S. cerevisiae* LAG1 probe to a Northern blot of human mRNA from several human tissues, including heart, brain, placenta, lung, liver, skeletal muscle, kidney and pancreatic tissues. As illustrated, an approximate 7 kb human LAG1 transcript is detected.

Figure 16:
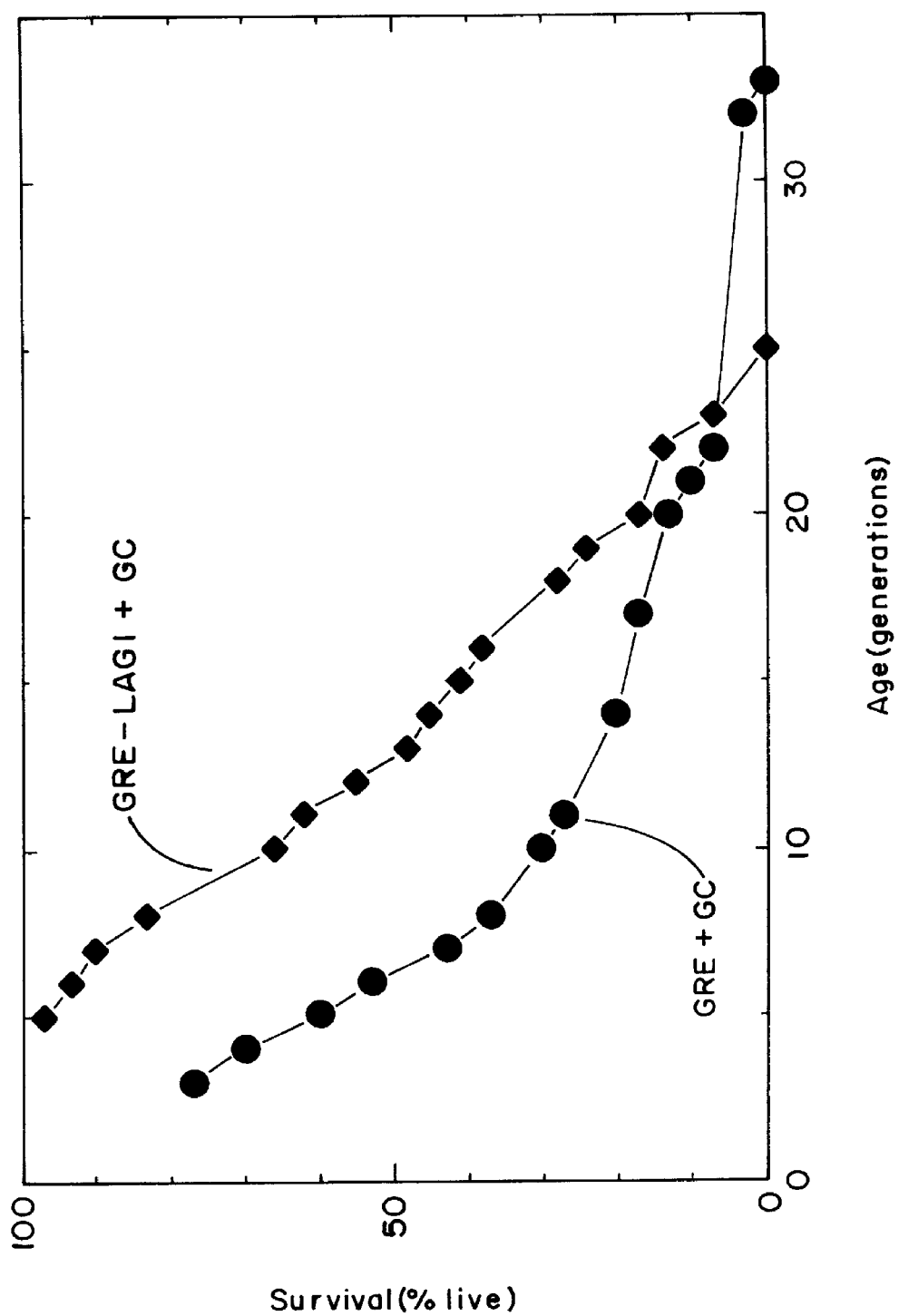

FIG. 16 depicts the survival of cells at pH 5.3 to 5.5 when LAG1 is overexpressed (GRE-LAG1+GC, ♦) compared to cells with no additional LAG1 expression (GRE+GC, ●).

Figure 17:
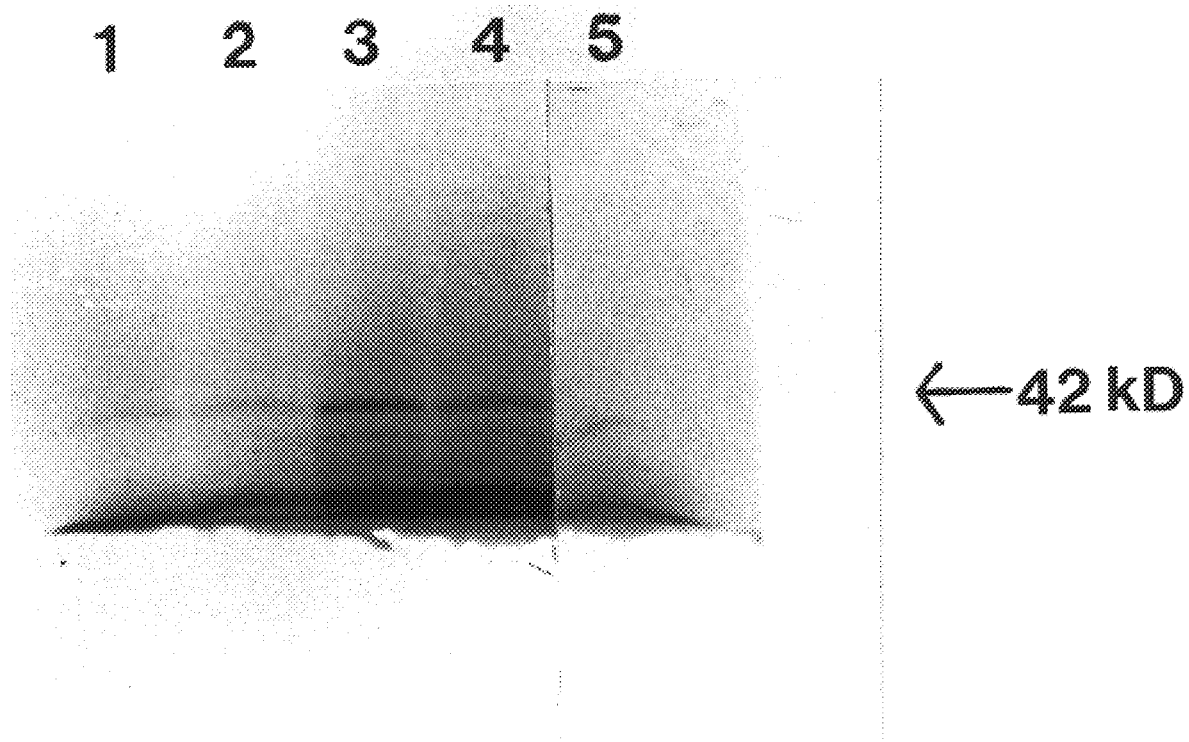

FIG. 17 depicts the LAG1 polypeptide products of in vitro translation of LAG1 RNA separated on an SDS polyacrylamide protein gel. In lanes 1 and 2, 1 μg of LAG1 RNA was added to the reaction. In lanes 3 and 4, 2 μg of LAG1 RNA was added to the reaction. Lane 5 is a control containing no exogenously added RNA. The arrow identifies the LAG1 polypeptide which was estimated to be 42 kd by this procedure.

DETAILED DESCRIPTION OF THE INVENTION

LAG1 is a unique, single-copy gene originally isolated in accordance with the present invention from *Saccharomyces cerevisiae*. The nucleotide sequence of *Saccharomyces cerevisiae* LAG1 is provided herein as SEQ ID NO:1. LAG1 was isolated by differential screening of a *Saccharomyces cerevisiae* genomic library using cDNA probes prepared from young and old cell poly(A)+mRNA as described in Egilmez et al. (1989 *J. Biol. Chem.* 264: 14312–17). LAG1 transcripts are moderately abundant in young yeast cells but decrease progressively as the cells age.

The present invention is directed to isolated nucleic acids encoding LAG1 polypeptides which can increase the longevity, reproductive capacity and tolerance to cellular stress of eukaryotic cells. Preferred nucleic acids include nucleic acids having SEQ ID NO:1, SEQ ID NO:3 or SEQ ID NO:5, and nucleic acids having the insert in pDF5 given ATCC No. 75790. Moreover, the present invention provides nucleic acids capable of hybridizing to a DNA having SEQ ID NO:1 under moderate to high stringency conditions. Such nucleic acids encode various species of LAG1 polypeptides such as, for example, yeast, Podospora, galago, salmon and mammalian species including human, bovine, murine and the like. Preferred nucleic acids of this invention are those which encode the yeast LAG1 polypeptide, the human LAG1 polypeptide and the murine LAG1 polypeptide. Furthermore, the present invention provides nucleic acids which encode a LAG1 polypeptide which differ from the aforementioned nucleic acids in codon sequence due to the degeneracy of the genetic code. Preferably, the present LAG1 nucleic acids have at least 50% homology to SEQ ID NO:1, SEQ ID NO:3 or SEQ ID NO:5.

In one embodiment, the present invention provides a *Saccharomyces cerevisiae* nucleic acid having SEQ ID NO:1 which encodes a full length LAG1 polypeptide. However, according to the present invention, longevity of yeast cells is increased by mutation of the LAG1 gene, especially deletion of the life-span limiting domain of LAG1. For example, a deletion of 1,234 base pairs, including the sequence coding for the N-terminal 193 amino acids, from the 5' end of SEQ ID NO:1 gives rise to a preferred nucleic acid having SEQ ID NO:3. A SEQ ID NO:3 nucleic acid encodes a mutant polypeptide with SEQ ID NO:4 which has no life-span limiting domain. Expression of the SEQ ID NO:4 polypeptide increases yeast cell longevity without any negative effects upon cell growth or viability. Thus, the life-span limiting domain resides within the region of SEQ ID NO:2 delimited by about amino acid 1 to about amino acid 190.

The present invention also provides a nucleic acid having SEQ ID NO:5 which encodes the life-span limiting domain but which has a deletion eliminating the life-span extending domain of LAG1.

A plasmid, identified as pDF5, which contains a nucleic acid encoding the entire *S. cerevisiae* LAG1 coding region was deposited with the American Type Culture Collection (12301 Parklawn Drive, Rockville, Md. 20852) on Jun. 1, 1994. This pDF5 plasmid was provided ATCC No. 75790.

As is known to the skilled artisan, a given amino acid is encoded by different three-nucleotide codons. Such degeneracy in the genetic code therefore means that the same polypeptide sequence can be encoded by numerous nucleotide sequences. The present invention is directed to any nucleotide sequence which can encode the present LAG1 polypeptides. Therefore, for example, while the LAG1 polypeptide sequence of SEQ ID NO:2 is encoded by a nucleic acid having SEQ ID NO:1, there are alternative nucleic acid sequences which can encode the same SEQ ID NO:2 polypeptide sequence. The present invention is also directed to any of the present isolated LAG1 nucleic acids which have such alternative nucleic acid sequences.

The present invention also provides nucleic acids capable of hybridizing to a DNA having SEQ ID NO:1. According to this invention, a *Saccharomyces cerevisiae* LAG1 DNA probe detects a nucleotide sequence in the human genome under moderate to high stringency hybridization conditions (see FIG. 5). Moreover, the human homologue of LAG1 is expressed in human tissues as a transcript of about 7.0 kb (see FIG. 15). Similarly, in accordance with the present invention, LAG1 has been detected in the genomic DNA of other eukaryotes including bovine, mouse, galago and salmon. Hence, the LAG1 gene is highly conserved across the spectrum of eukaryotes and LAG1 homologues from other species are isolated by techniques readily available to the skilled artisan.

Isolation of a LAG1 nucleic acid is accomplished or confirmed by assaying for LAG1 function. Hence, as provided herein, LAG1 nucleic acids encode a life-span extending function. LAG1 nucleic acids also encode a life-span limiting function, a tolerance to stress function and an increased reproductive capacity function. As used herein, the life-span extending function increases the length of time that eukaryotic cells remain viable. The life-span limiting function sets the normal life span of eukaryotic cells, and when this function is deleted or eliminated, cells live longer, for example, about 45% to about 60% longer. The tolerance to stress function increases a eukaryotic cell's resistance to and viability under stressful conditions such as low pH and starvation. Low pH is about pH 5.0 to about pH 5.5. The increased reproductive capacity function increases the number of cellular divisions that a eukaryotic cell undergoes, e.g. by at least about 10.

In one embodiment, a LAG1 genomic DNA can be isolated from another eukaryotic species, e.g. a mammal such as a mouse or a human, by hybridization methods. This method includes providing a LAG1 probe to a eukaryotic chromosomal library for a time and under conditions sufficient for hybridization; identifying a hybridization complex containing the probe and the eukaryotic LAG1 genomic DNA; and isolating the eukaryotic LAG1 genomic DNA. As used herein a LAG1 probe is selected from SEQ ID NO:1 such that the LAG1 probe has sufficient length and sufficient complementarity to hybridize to the eukaryotic LAG1 genomic DNA. Alternatively, LAG1 probe has sufficient length and sufficient complementarity to hybridize to SEQ ID NO:1. Preferably, the LAG1 probe has at least about 50% complementarity to SEQ ID NO:1. The LAG1 probe is preferably at least about 14 nucleotides to about 17 nucleotides.

This method is also used for isolating a eukaryotic LAG1 cDNA when a eukaryotic cDNA library is used.

In a related embodiment, the present invention provides a method of isolating a eukaryotic LAG1 nucleic acid by in vitro nucleic acid amplification. Such methodology includes contacting a sample containing the LAG1 nucleic acid with at least one appropriate oligonucleotide and an amplification enzyme for a time and under conditions sufficient to produce RNA or DNA copies of the LAG1 nucleic acid. These copies are identified and isolated. Preferably, the oligonucleotides used for in vitro amplification are selected from SEQ ID NO:1 to have sufficient complementarity and sufficient length to hybridize to the eukaryotic LAG1 nucleic acid and permit amplification. Alternatively, the oligonucleotide has sufficient complementarity and sufficient length to hybridize to SEQ ID NO:1. A preferred oligonucleotide has at least 50% complementarity to SEQ ID NO:1.

Preferred oligonucleotides have at least about 14 to about 17 nucleotides.

Complementarity between nucleic acids is the degree to which the bases in one nucleic acid strand can hydrogen bond, or base pair, with the bases in a second nucleic acid strand. As used herein, sufficient complementarity means that a sufficient number of the nucleotides in SEQ ID NO:1 form base pairs with nucleotides in a nucleic acid, e.g. a eukaryotic LAG1 nucleic acid from a mammal, a LAG1 oligonucleotide or a LAG1 probe, to generate a stable hybridization complex at about room temperature (i.e. at about 20° C. to about 25° C.)

Complementarity can sometimes be conveniently described by the percentage, i.e. proportion, of nucleotides which can form base pairs between two nucleic acid strands or within a specific region or domain of the two strands. When expressed or measured by percentage of base pairs formed, the degree of complementarity can range from at least about 50% to full, i.e. 100% complementarity. In general, the overall degree of complementarity between a eukaryotic LAG1 nucleic acid, oligonucleotide or probe and SEQ ID NO:1 is at least about 50%, and preferably about 60% or higher.

The term homology, as used herein, is the degree of sequence identity between two nucleic acid strands or two polypeptide sequences. When a target is a double-stranded nucleic acid, one target strand is complementary, and the other target strand is homologous, to a probe or oligonucleotide of the present invention. Moreover the sequence listing provided herein recites the sequence of only one nucleic acid strand. However as provided herein some of the sequences described in the sequence listing are intended to be double-stranded. Accordingly, when a double-stranded target is identified by sequence number a probe or oligonucleotide can also be homologous to the recited sequence and hence can hybridize to the strand not recited in the sequence listing.

The degree of homology can also be described by the percentage of identical nucleotides or amino acids in two nucleotide or polypeptide sequences, respectively. In particular, the degree of homology between a target nucleic acid and a probe or oligonucleotide of the present invention can vary so long as selective hybridization is attained, and can range from at least about 50% to about 100% homology. In general, the overall degree of homology between a eukaryotic LAG1 nucleic acid, oligonucleotide or probe and SEQ ID NO:1 is preferably about 60% or higher. Similarly, the degree of homology between a LAG1 polypeptide and SEQ ID NO:2, SEQ ID NO:4 or SEQ ID NO:6 can range preferably from at least about 25% to 30% to about 100% homology and is more preferably about 30% or higher.

Therefore, according to the present invention eukaryotic nucleic acids homologous to *S. cerevisiae* LAG1 nucleic acids are readily isolated, for example, from Podospora, human, bovine, mouse, galago, salmon and related eukaryotes. Hybridization and in vitro amplification conditions for such isolation can readily be ascertained by the skilled artisan. See, e.g., Sambrook et al. 1989 Molecular Cloning: A Laboratory Manual, Vol. 1–3, Cold Spring Harbor Press, Cold Spring Harbor, N.Y.

Figure 5:
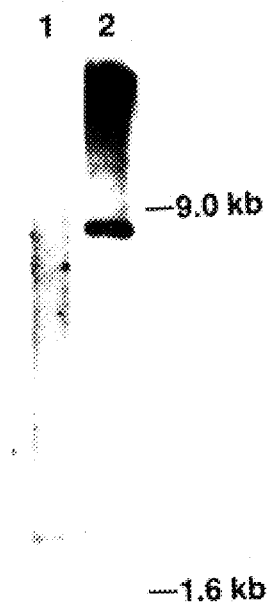
FIG. 5 depicts an autoradiogram of a Southern genomic blot of human DNA probed with the S. cerevisiae LAG1 1,052-bp PstI EcoRI fragment. Lane 1, human DNA; lane 2, yeast DNA. A 1-kb ladder (Bethesda Research Laboratories) was electrophoresed alongside the samples as a size marker.

For example, when moderate to high stringency hybridization conditions are used, a 1,052 base pair PstI-EcoRI fragment including the coding region of *S. cerevisiae* LAG1 detectably hybridizes to a human LAG1 homologue on a Southern blot of genomic human DNA (see FIG. 5). Such hybridization conditions include, for example, a temperature of about 42° C., a formamide concentration of about 35% and a salt concentration of about 1.1M NaCl.

In the aspect of this invention providing a method of isolating LAG1 nucleic acids from other eukaryotes by in vitro nucleic acid amplification, a LAG1 nucleic acid is copied using at least one appropriate oligonucleotide and an appropriate amplification enzyme. The oligonucleotide is selected such that it is sufficiently complementary to hybridize to the eukaryotic LAG1 nucleic acid to permit amplification. In one embodiment, the oligonucleotide is at least about 14 nucleotides long and at least 50% homologous to nucleic acid of SEQ ID NO:1. Preferably the oligonucleotide includes a nucleotide sequence of at least about 14 nucleotides which is about 70% homologous to SEQ ID NO:1.

As provided herein, the LAG1 target nucleic acid for in vitro amplification is that segment of nucleic acid which is copied during amplification. Accordingly, the oligonucleotide(s) employed for amplification hybridize to only a portion of the target nucleic acid. This portion is the oligonucleotide binding site. An oligonucleotide binding site can define the 3' or 5' end of the target nucleic acid. Therefore, when copies of the target nucleic acid are made during amplification the actual 3' or 5' ends of such copies are composed of oligonucleotides which, e.g. act as primers for synthesis of the copy. Alternatively, a portion or the whole of an oligonucleotide sequence is copied during the amplification procedure or the oligonucleotide sequence is not to be copied at all but instead forms a recognition site for binding the amplification enzyme.

As used herein, the methods of amplifying LAG1 target sequences are methods of in vitro nucleic acid amplification which include any procedure using an oligonucleotide to direct synthesis of a nucleic acid copy of the target sequence. In vitro nucleic acid amplification thus allows selective synthesis of a specific DNA or RNA target relative to the complex bulk of nucleic acid present in a sample. The specificity of the process is determined by the oligonucleotide, e.g. the oligonucleotide primers, capable of hybridizing with LAG1 nucleic acids to the exclusion of other nucleic acids.

Conditions for in vitro nucleic acid amplification generally include temperature and salt concentrations permitting selective hybridization between the oligonucleotide and target. The skilled artisan can readily manipulate such conditions to achieve selective hybridization. For example, preferred hybridization temperature is about 5° C. to about 10° C. below the melting temperature of the target: oligonucleotide hybrid (Sambrook et al.). This hybridization temperature can readily be varied to accommodate other considerations such as the thermal instability of the amplification enzyme. The skilled artisan can readily ascertain appropriate temperature and salt conditions for hybridization of a LAG1 oligonucleotides to LAG1 nucleic acids from other eukaryotes.

Conditions for in vitro nucleic acid amplification also include those salt, cation, pH, nucleotide subunit concentration and temperature conditions required for enzymatic activity of the amplification enzyme. For example, some amplification enzymes require a cation such as magnesium for optimal activity. Moreover, copying of LAG1 target nucleic acids requires that the appropriate nucleotide subunits be added to the amplification mixture, e.g. ATP, CTP, GTP, UTP, dATP, dCTP, dGTP or dTTP. While some amplification enzymes like the *Thermus aguaticus* or *Thermococcus litoralis* DNA polymerases are stable for extended periods of time at 98° C., others such as the SP6 or T7 RNA polymerases are rapidly denatured at a temperature of about 65° C. Optimal salt, cation, pH and temperature conditions for obtaining amplification enzyme activity are readily available to the skilled artisan, e.g. from a commercial manufacturer of these enzymes.

In general DNA polymerases can only copy DNA from a single-stranded target. Therefore the present methods can include at least one denaturing step for double-stranded target nucleic acids. Such methods can further include at least one denaturing step for separating a DNA or RNA copy from a target nucleic acid.

In vitro nucleic acid amplification techniques are known in the art. A review of such techniques can be found in Kwoh et al. (1990) Am. Biotechnol. Lab. 8:14. In vitro nucleic acid amplification techniques include polymerase chain reaction (PCR), transcription-based amplification system (TAS), self-sustained sequence replication system (3SR), ligation amplification reaction (LAR), ligase-based amplification system (LAS), Qβ RNA replication system and run-off transcription.

PCR is a method for primer-directed enzymatic amplification of target nucleic acids. PCR synthesis occurs by repeated cycles of heat denaturation of the target, primer annealing and primer extension. These cycles can be performed manually or, preferably, automatically. Thermal cyclers such as the Perkin-Elmer Cetus cycler are specifically designed for automating the PCR process, and are preferred. The number of cycles per round of synthesis can be varied from 2 to more than 50, and is readily determined by considering the source and amount of the nucleic acid template, the desired yield and the procedure for detection of the synthesized DNA fragment. PCR techniques and many variations of PCR are known. Basic PCR techniques are described by Saiki et al. (1988 Science 239:487–491) and by U.S. Pat. Nos. 4,683,195, 4,683,202 and 4,800,159, which are incorporated herein by reference.

The conditions generally required for PCR include temperature, salt, cation, pH and related conditions needed for efficient copying of the target. PCR conditions include repeated cycles of heat denaturation (i.e. heating to at least about 95° C.) and incubation at a temperature permitting target: oligonucleotide hybridization and copying of the target by the amplification enzyme. Heat stable amplification enzymes like the *Thermus aguaticus* or *Thermococcus litoralis* DNA polymerases are commercially available which eliminate the need to add enzyme after each denaturation cycle. The salt, cation, pH and related factors needed for amplification enzyme activity are available from commercial manufacturers of amplification enzymes.

The transcription-based amplification system (TAS) utilizes a sample (sense) RNA template from which a double stranded complementary DNA (i.e. cDNA) is made. One or more of the oligonucleotides used for synthesis of the cDNA contains an RNA polymerase recognition site. An RNA polymerase capable of recognizing and synthesizing RNA starting at that recognition site is then added to produce many RNA copies of the cDNA. To achieve even greater amounts of an RNA synthetic product, additional rounds of cDNA synthesis can be performed using the synthesized RNA as template and this additional cDNA can be used to make even more RNA product. RNA polymerases which can be used for TAS include, for example, SP6, T3, T7 and other RNA polymerases. TAS techniques are described by Kwoh et al.

Conditions for TAS amplification are generally determined by the temperature, salt, cation and pH requirements of the RNA polymerase employed. These conditions are readily available to the skilled artisan, e.g. as provided by commercial manufacturers of such RNA polymerases.

When a TAS technique is performed the subject oligonucleotides can contain an additional sequence which encodes a recognition or binding site for an RNA polymerase, e.g. a T7, T3 or SP6 RNA polymerase recognition sequence. RNA polymerase recognition sequences are well known in the art and are readily incorporated into the present oligonucleotides by the skilled artisan.

The self-sustained sequence replication (3SR) procedure involves continuous cycling of reverse transcriptase and RNA polymerase synthesis. 3SR utilizes RNase H enzymatic degradation of the RNA in an RNA:cDNA duplex, an innovation which eliminates thermal denaturation and repetitive addition of reagents. The 3SR procedure involves synthesis of a double stranded cDNA wherein the oligonucleotide used for synthesis of either the first or second cDNA strand, has an RNA polymerase recognition site. The double-stranded cDNA then acts as target for synthesis of either an antisense or sense RNA, depending on whether the first or second cDNA strand, respectively, has the RNA polymerase recognition site. Since there is no thermal denaturation step, the enzymes used for cDNA synthesis remain active and can produce more cDNA from the sense or antisense RNA product which can itself serve as a target for more RNA product. 3SR techniques are described by Kwoh et al.

Conditions for 3SR amplification are generally determined by the temperature, salt, cation and pH requirements of the reverse transcriptase and the RNA polymerase employed. These conditions are readily available to the skilled artisan, e.g. as provided by commercial manufacturers of such enzymes.

The 3SR procedure has some advantages over PCR or TAS in that all reagents are placed in a single tube and incubation is at a single temperature. Accordingly, no thermal cycling or repeated addition of reagents is required. 3SR is also more rapid than many other in vitro nucleic acid amplification procedures since an approximate $10^6$-fold amplification of a desired DNA or RNA is achieved in about an hour.

DNA ligase is used to synthesize DNA by repeatedly joining oligonucleotides hybridized to a template nucleic acid. Such procedures have been termed ligation amplification (LAR) and ligase-based amplification systems (LAS). LAR or LAS utilizes four oligonucleotides wherein two oligonucleotides hybridize to one strand of the target DNA and the other two hybridize to the complementary sequences. The adjacently hybridizing oligonucleotides are then joined by DNA ligase. After thermal denaturation, an additional cycle of hybridization and ligation can be performed. Each round of denaturation, hybridization and ligation increases the ligated product by about two-fold. Blunt end ligation of oligonucleotides hybridizing to complementary oligonucleotides can be controlled by adjusting the temperature of the ligation step.

Conditions for LAS include temperature, salt, cation, pH and the like needed for repeated rounds of denaturation, hybridization and ligation. Denaturation is generally performed at about 95° C. to about 100° C. Hybridization is preferably performed at about 5° C. to about 10° C. below the melting temperature of the target:oligonucleotide hybrid, however slow cooling from the denaturation temperature can also lead to selective hybridization between the target and the oligonucleotide(s). The conditions needed for efficient ligation are well known to the skilled artisan (e.g. see Sambrook et al.). The LAS technique is also described by Kwoh et al.

An RNA can be synthesized from a nucleic acid by employing a Qβ replicase RNA replication system in which a first strand of a cDNA is made having a Qβ replicase 5'-recognition site lying on the 3'-side of an RNA polymerase recognition site. This is done with an oligonucleotide capable of hybridizing to an RNA target which also encodes the 5'-Qβ and RNA polymerase recognition sites in the correct positions. A second cDNA strand is then synthesized using an oligonucleotide encoding a Qβ 3'-recognition site. An RNA polymerase can then use the double-stranded cDNA as a template for synthesis of antisense RNA having, as 5' and 3' ends, the respective 5'- and 3'-Qβ replicase recognition sites. This antisense RNA can then serve as a template for Qβ replicase synthesis of sense and antisense RNA. This Qβ replicase technique is described by Kwoh et al.

In this regard, the subject oligonucleotides can contain additional nucleotide sequences which encode an RNA polymerase recognition site, the 5' Qβ replicase recognition site and the 3' Qβ replicase recognition site as necessary to conduct Qβ replicase RNA replication. Such sites are well known in the art and can readily be incorporated in the oligonucleotides of the present invention.

A suitable amount of each oligonucleotide for in vitro nucleic acid amplification to enable isolation of a eukaryotic LAG1 RNA or DNA is about 0.01 μmole to about 5 μmole, and preferably about 0.05 μmole to about 1.0 μmole. Other reagents as needed are added to the amplification reaction mixtures. Such reagents include nucleotides, additional enzymes, a source of a high-energy phosphate (e.g. ATP), and the like. Moreover the target nucleic acid can be either DNA, RNA or both and depends on the in vitro nucleic acid amplification system selected. In many of these procedures DNA is the preferred template.

As provided herein an amplification enzyme is any enzyme which can be used for in vitro nucleic acid amplification, e.g. by the above-described procedures. Such amplification enzymes include *Escherichia coli* DNA polymerase I, Klenow fragment of *E. coli* DNA polymerase I, T4 DNA polymerase, T7 DNA polymerase, *Thermus aguaticus* DNA polymerase, *Thermococcus litoralis* DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Qβ replicase.

The preferred oligonucleotides for the present amplification methods include oligonucleotides which can selectively hybridize to LAG1 from the selected eukaryotic species, e.g. as observed by Southern or Northern analysis of nucleic acids from that species. To achieve selective hybridization, oligonucleotides are selected to be of sufficient length and complementarity to provide detectable hybridization to one to two bands on a Southern or Northern blot of that eukaryote's DNA or RNA. In one embodiment, oligonucleotides each have a nucleotide sequence with at least about 50% complementarity to either strand of SEQ ID NO:1. Preferred oligonucleotides have at least about 70%, and more preferably 80%, sequence homology to SEQ ID NO:1.

Moreover, preferred oligonucleotides are not selected from regions common to a wide variety of genes. For example, oligonucleotides and probes encoding the membrane spanning domains of LAG1 polypeptides are preferably not selected. Preferred oligonucleotides are selected from either the LAG1 non-coding or coding regions. When two oligonucleotides are employed, preferred oligonucleotides are at least 50% homologous to SEQ ID NO:1, e.g. to the 5' and 3' ends of SEQ ID NO:1.

Any of these oligonucleotides can have additional sequences which encode RNA polymerase recognition sites or Qβ replicase recognition sites in the configuration necessary to practice in vitro nucleic acid amplification.

The length of the nucleic acids or oligonucleotides for use in isolating eukaryotic LAG1 nucleic acids depends on several factors including the nucleotide sequence and the temperature at which these nucleic acids are hybridized or used during in vitro nucleic acid amplification. The considerations necessary to determine a preferred length for a nucleic acid or oligonucleotide are well known to the skilled artisan (Sambrook et al.).

For example, as is known to the skilled artisan, the length of a short nucleic acid or oligonucleotide can relate to its hybridization selectivity. When a test sample contains complex mixtures of nucleic acids, e.g. mammalian genomic DNA, oligonucleotides which have less than about 14 nucleotides may hybridize to more than one site in the mammalian genome. These short oligonucleotides accordingly would not have sufficient hybridization selectivity for detecting a single target nucleic acid. However the sequence of a nucleic acid which is at least about 14–15 nucleotides is generally represented only once in a mammalian genome (Sambrook et al. 1989 Molecular Cloning: A Laboratory Manual, Vol. 2, Cold Spring Harbor Press, Cold Spring Harbor, N.Y.; pp. 11.7–11.8). Accordingly, to eliminate cross hybridization with mammalian genomic DNA, the nucleic acid probes and oligonucleotides of the present invention are generally at least about 14 nucleotides long.

However, as is known to the skilled artisan nucleic acids or oligonucleotides which are shorter than 14 nucleotides, e.g. oligonucleotides of about 10 to about 12 or more nucleotides, are specific for a given target. Therefore the term at least "about" is used to include any such nucleic acids and oligonucleotides which are less than 14 nucleotides long but which can specifically hybridize to a eukaryotic LAG1 nucleic acid.

Preferably, the present nucleic acids and oligonucleotides are at least 15 nucleotides in length. More preferred nucleic acids and oligonucleotides are at least 17 nucleotides in length (Sambrook et al., pp. 11.7–11.8).

Nucleic acid probes of the present invention contain at least about 14 nucleotides to about 2500 nucleotides. Oligonucleotides of the present invention typically contain at least about 14 to about 150 or more nucleotides.

Preferred nucleic acid probes and oligonucleotides include the 1,052 bp PstI-EcoRI fragment of SEQ ID NO:1 and the 3' and 5' ends of SEQ ID NOS:1 and 3.

A further embodiment of the present invention includes isolated nucleic acids having an antisense nucleotide sequence of an RNA transcribed by any of the present nucleic acids. These antisense oligonucleotides are used to bind to LAG1 mRNA, e.g. as described in Uhlmann et al. (1990 Chemical Reviews 90: 544–584). Thus, in this embodiment, the present antisense nucleic acids preferably have sufficient length and complementarity to hybridize to a non-template strand of one of the present isolated nucleic acids, e.g. SEQ ID NO:1. As used herein the template strand is the DNA strand read by RNA polymerase; such a template strand is complementary to an RNA synthesized therefrom. Similarly, the non-template strand of the DNA has a sequence similar to the transcribed RNA. Thus, for example, the present antisense nucleic acids are at least about 50% complementary to the non-template strand of SEQ ID NO:1, SEQ ID NO:3 or SEQ ID NO:5. These antisense oligonucleotides preferably are at least about 14 to about 17 or more nucleotides in length, thereby permitting selective hybridization to a target nucleic acid.

Moreover, the present invention contemplates antisense nucleic acids which have sufficient length and complementarity to hybridize to a transcriptional regulatory region of a eukaryotic LAG1 gene. These antisense oligonucleotides are used to regulate the transcription of the LAG1 gene, e.g. as described in Uhlmann et al. (1990 Chemical Reviews 90: 544–584) or Cooney et al. (1988 Science 241: 456–459). In a preferred embodiment, such antisense nucleic acids have at least about 50% complementarity to SEQ ID NO:7. For example, these transcriptional regulatory regions include a binding site for GCN4 protein or regulatory complex 2 (RC2).

The binding site for GCN4 is TGACT which is found at position −91 to −87 relative to the LAG1 transcriptional start site. This protein is an activator of several genes under general control, and the core DNA-binding sequence is found at HIS1, HIS3, HIS4 and TRP5 promoters. The consensus sequence to which regulatory complex 2 (RC2) binds (Arcangioli, 1985 EMBO J. 4: 2627–33), TGACCGA, is present at position −278 to −272 relative to the LAG1 transcriptional start site. Thus, the binding sites for GCN4 protein and regulatory complex 2 (RC2) are transcriptional regulatory regions of the 5' LAG1 transcriptional control region. This control region and its regulatory elements are used as a promoter to express LAG1. In another embodiment, the LAG1 control region and its regulatory elements are used to express a heterologous gene product.

Sense or antisense oligonucleotides and nucleic acids, e.g. of up to about 50 nucleotides, can be chemically synthesized by available synthetic procedures for nucleic acids. Chemical synthesis of nucleic acids is well known in the art and is achieved by solution or solid phase techniques. Moreover, oligonucleotides or nucleic acids of defined sequence are purchased commercially or are made by any of several different synthetic procedures including the phosphoramidite, phosphite triester, H-phosphonate and phosphotriester methods, typically by automated synthesis meincorporated id bases can also be incorporated into the nucleic acid, e.g. inosine. If modified phosphodiester linkages are used the synthetic procedures are altered as needed according to known procedures. In this regard, Uhlmann et al. (1990 Chemical Reviews 90:543–584) provide references and outline procedures for making nucleic acids with modified bases and modified phosphodiester linkages.

Enzymatic methods are also available for DNA, RNA or oligonucleotide synthesis. For DNA and oligodeoxyribonucleotide synthesis, these methods frequently employ Klenow, T7, T4, Taq or E. coli DNA polymerases, e.g. as described in Sambrook et al. Enzymatic methods of RNA or oligoribonucleotide synthesis frequently employ SP6, T3 or T7 RNA polymerase as described, for example, in Sambrook et al. Reverse transcriptase can also be used to synthesize DNA from RNA.

To prepare a nucleic acid or oligonucleotide enzymatically requires a template nucleic acid which can either be synthesized chemically, or be obtained as mRNA, genomic DNA, cloned genomic DNA, cloned cDNA or recombinant DNA. Some enzymatic methods of DNA or oligodeoxyribonucleotide synthesis can require a short primer oligonucleotide; this primer is obtained or synthesized by any available procedure.

After enzymatic or chemical synthesis, nucleic acids and oligonucleotides are purified by polyacrylamide gel electrophoresis, or by any of a number of chromatographic methods, including gel, ion-exchange and high pressure liquid chromatography. To confirm a nucleotide sequence, nucleic acids and oligonucleotides are subjected to DNA sequencing by available procedures, including Maxam and Gilbert sequencing, Sanger sequencing, capillary electrophoreses sequencing or by using selective chemical degradation of oligonucleotides bound to Hybond paper. Sequences of short oligonucleotides can also be analyzed by plasma desorption mass spectroscopy or by fast atom bombardment (McNeal et al. (1982) J. Am. Chem. Soc. 104:976; Viari et al. (1987) Biomed. Environ. Mass Spectrom. 14:83; Grotjahn et al. (1982) Nucleic. Acid Res. 10:4671). Sequencing methods are also available for RNA oligonucleotides.

The present invention also contemplates labeling the subject nucleic acids and oligonucleotides for use as probes to detect a target LAG1 nucleic acid. Labeled probes have utility in diagnostic and analytical hybridization procedures for localizing, quantitating or detecting a target nucleic acid in tissues, chromosomes or in mixtures of nucleic acids.

Labeling of a nucleic acid or an oligonucleotide is accomplished by incorporating a "reporter molecule" into the subject nucleic acids and oligonucleotides by known procedures, e.g. as provided in Sambrook et al. or Beaucage et al. (1993, Tetrahedron 49:1925–1963). A "reporter molecule", as defined herein, is a molecule or atom which, by its chemical nature, provides an identifiable signal allowing detection of the nucleic acid or the oligonucleotide. Detection is either qualitative or quantitative.

The present invention contemplates using any commonly used reporter molecule including, for example, radionuclides, enzymes, fluorophores, biotins, digoxigenin, chemiluminescent molecules, bioluminescent molecules, avidin, streptavidin, psoralens, chelated heavy metals, and luciferin. The most commonly used reporter molecules are either enzymes, digoxigenin, radionuclides or fluorophores which are linked to nucleotides either before or after nucleic acid or oligonucleotide synthesis.

Commonly used enzymes include horseradish peroxidase, alkaline phosphatase, glucose oxidase and β-galactosidase, among others. Enzymes can be conjugated to avidin or streptavidin for use with a biotinylated probe. Similarly, nucleic acid probes can be conjugated to avidin or streptavidin for use with a biotinylated enzyme. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1,2-phenylenediamine, 5-aminosalicylic acid or toluidine are commonly used.

A digoxigenin reporter molecule is detected by binding an anti-digoxigenin antibody which has conjugated thereto a second reporter molecule, e.g. an enzyme. The antibody-conjugated enzyme is then detected by application of a substrate for the enzyme.

Radionuclides are commonly used reporter molecules to form nucleic acid or oligonucleotide probes. Radionuclides can be incorporated into the present nucleic acids and oligonucleotides either during synthesis or by end-labeling after synthesis as described in Sambrook et al. To incorporate radionuclides during nucleic acid synthesis radioactively labeled nucleotides are used, e.g. nucleotides with an $\alpha$-$^{32}$P moiety. Radionuclides can be incorporated after oligonucleotide synthesis by end labeling either the 3' or 5' end of the present nucleic acids and oligonucleotides. Such end labeling can be done enzymatically, e.g. a 5'-phosphate can be enzymatically removed with alkaline phosphatase and then replaced with a radioactively labeled 5'-phosphate, e.g. the $\gamma$-$^{32}$P from adenosine 5'-[$\gamma$-$^{32}$P]triphosphate, using T4 polynucleotide kinase. Radioactively labeled nucleotide triphosphates are readily available commercially.

Fluorophores that are readily available and suitable for the methods of the present invention include fluorescein isothiocyanate (FITC), rhodamine red and the like. Such fluorophores can be covalently linked to the present nucleic acids and oligonucleotide by readily available procedures, e.g. as provided in Beaucage et al. (1993 Tetrahedron 49: 1925–1963).

Therefore, nucleic acid and oligonucleotide probes linked to reporter molecules are used as herein described in the detection and isolation of a LAG1 DNA or RNA from other eukaryotic species, e.g. from Podospora, human, bovine, mouse, galago, salmon and related eukaryotes. Moreover, these probes are also used to detect LAG1 nucleic acids from a variety of eukaryotes by solution hybridization, Southern analysis, Northern analysis, in situ hybridization to tissue sections or chromosomal squashes and other analytical and diagnostic procedures. The methods of using such hybridization probes are well known. Some examples of such methodology are provided by Sambrook et al.

In another embodiment, the present invention provides isolated eukaryotic LAG1 polypeptides which are encoded by any of the present LAG1 nucleic acids identified herein. The *Saccharomyces cerevisiae* LAG1 polypeptides provided herein include polypeptides having SEQ ID NO:2, SEQ ID NO:4, SEQ ID NO:6 and derivatives thereof. In a preferred embodiment the present isolated eukaryotic polypeptides have at least about 25% to 30% homology to SEQ ID NO:2, SEQ ID NO:4 or SEQ ID NO:6.

The SEQ ID NO:1 nucleic acid encodes a 411 amino acid polypeptide having SEQ ID NO:2. Hydropathy analysis of this LAG1 polypeptide, e.g. by the SOAP program, indicates LAG1 has several transmembrane domains. Thus, a LAG1 polypeptide with such a domain may be membrane bound.

According to the present invention, full-length LAG1 has at least two functional domains: a life-span limiting domain residing in the approximate N-terminal half of the protein and a C-terminal domain which extends cellular life span. The present invention is directed to all eukaryotic polypeptides which have one or the other or both of these two domains.

The life-span limiting domain of *Saccharomyces cerevisiae* LAG1 lies within the region of SEQ ID NO:2 delimited by about amino acid position 1 to about amino acid position 190. Deletion of the N-terminal 193 amino acids from SEQ ID NO:2 gives rise to a preferred LAG1 polypeptide, SEQ ID NO:4, which encodes the life span extending domain but not the life-span limiting domain.

Moreover, the present invention is directed to LAG1 polypeptides from other eukaryotic species such as, for example, human, bovine, murine, Podospora, galago salmon and related eukaryotes whether prepared synthetically or recombinantly. LAG1 polypeptides are isolated by recombinant techniques readily available to the skilled artisan. Preferably, these polypeptides have at least about 25% to 30% homology to SEQ ID NO:2, SEQ ID NO:4 or SEQ ID NO:6.

The present polypeptides include derivatives and fragments or peptides of the full length LAG1 polypeptides of the present invention which confer the biological activity of the polypeptides with, for example, SEQ ID NO:2, SEQ ID NO:4 or SEQ ID NO:6. Thus, such fragments and derivatives as defined below, include those polypeptides which increase the longevity, tolerance to stress and reproductive capacity of, for example, human, bovine, murine, Podospora, galago, salmon, yeast and other eukaryotic cells.

Derivatives of the present polypeptides include all modifications to the subject polypeptides, including, for example, substitutions, deletions and insertions where the modified polypeptide retains the biological activity of the unaltered polypeptide having for example, SEQ ID NO:2, SEQ ID NO:4 and SEQ ID NO:6 with respect to increasing longevity, tolerance to stress or improving reproductive capacity in the narrow respective species of eukaryotes.

According to the present invention, the longevity function of LAG1 is assayed by observing whether a polypeptide derivative, or a nucleic acid encoding the polypeptide derivative, can increase the life span of a eukaryotic cell. The tolerance to stress function of LAG1 is assayed by observing whether a polypeptide its fragments or derivatives, or a nucleic acid encoding same, can increase the life span or viability of a eukaryotic cell exposed to stress, e.g. low pH and starvation. The improved cellular reproduction function of LAG1 is assayed by observing whether a polypeptide, its fragments or derivatives, or a nucleic acid encoding same, can increase the number of cellular divisions of a eukaryotic cell. Each of these functions is observed relative to a control cell which is not possessed of the polypeptide, derivative, or fragment or a nucleic acid encoding such a polypeptide, fragment or derivative.

LAG1 polypeptides are isolated from a variety of eukaryotic species, for example, by first isolating a nucleic acid encoding a LAG1 polypeptide using the hybridization and in vitro amplification methods described hereinabove. These isolated LAG1 nucleic acids are placed in an expression vector and the encoded polypeptides are expressed as described hereinbelow. These procedures are known to the skilled artisan and are readily adapted as needed to produce the desired eukaryotic isolated LAG1 polypeptides. See, Sambrook et al. 1989 *Molecular Cloning: A Laboratory Manual*, Vols. 1–3, Cold Spring Harbor Press, Cold Spring Harbor, N.Y.; Goeddel, D. V. (Ed.) 1990, Gene Expression Technology, *Methods in Enzymology*, Vol 185, Academic Press; Perbal, B. 1988, *A Practical Guide to Molecular Cloning*, John Wiley & Sons, Inc.; and Romanos et al. 1992, Yeast 8: 423–488.

After expression LAG1 polypeptides are identified by polyacrylamide gel electrophoresis or other procedures. These polypeptides are then isolated or purified by known procedures, e.g. detergent solubilization, salt precipitation, differential centrifugation, gradient centrifugation, column chromatographic procedures using gel filtration, ion exchange or reversed phase resins, and immunoaffinity or immunoprecipitation procedures.

In another embodiment, the present invention provides methods for increasing the longevity, reproductive capacity, or tolerance to stress of a eukaryotic cell, which includes administering to a cell an effective amount of either a wild type LAG1 polypeptide or a mutant LAG1 polypeptide, e.g. a LAG1 polypeptide lacking the life span limitation domain. In one embodiment, such polypeptides can have SEQ ID NO:2 or SEQ ID NO:4.

Another embodiment of the present invention is directed to a method for increasing the longevity or reproductive capacity of a eukaryotic cell which includes expressing a LAG1 polypeptide in the cell. According to the present invention such expression can increase the longevity of eukaryotic cells, particularly when the LAG1 polypeptide is expressed late in the life of the target cell. Such cells include mammalian such as for example, human, bovine, murine, and Podospora, galago and salmon. Moreover, such methods can also increase the tolerance of a eukaryotic cell to stress, e.g. starvation and acidic pH, where an acidic pH is about 5.0 to about 5.5.

These methods have particular utility in the yeast fermentation industry where yeast are employed in a variety of ways to produce a wide range of beverages or food products. For example, yeast are often used for the production of alcoholic beverages, baked goods, single-cell protein and for the production of proteins and enzymes. However, during fermentation or cultivation yeast are subjected to ,stressful conditions such as low pH and starvation. See, for example, A. H. Rose et al., eds., *The Yeast*, Vols. 1–4 (*Academic Press*, New York, 1987, 1989, 1991) and Y. H. Hui, ed., *Encyclopedia of Food Science and Technology*, Vols. 1–4 (John Wiley & Sons, Inc., New York, 1992) for fermentation procedures and conditions. The present invention provides strains of yeast which not only are resistant to these stressful conditions but which have an increased reproductive capacity and greater longevity. Hence, the present methods are used to improve the culture kinetics and increase the production capacity of yeast, thereby decreasing the amounts of raw materials needed by yeast for making alcoholic beverages, baked goods, proteins and enzymes.

Therefore, according to the present invention, to increase yeast cell longevity in a method of yeast fermentation, a LAG1 polypeptide is administered to a yeast cell in an amount sufficient to increase the longevity of the cell. Similarly, to increase yeast cell tolerance to cellular stress in a method of yeast fermentation, the method includes administering to a yeast cell a LAG1 polypeptide in an amount sufficient to increase the tolerance to stress of said cell. As used herein cellular stress includes starvation conditions and low pH. Starvation conditions occur, for example, when the yeast cells reach stationary phase. Low pH as contemplated herein is about 5.0 to about 5.5. Preferred LAG1 polypeptides for these methods include polypeptides with SEQ ID NO:2 or SEQ ID NO:4.

In these methods of yeast fermentation, the method can also include expressing a LAG1 polypeptide in the yeast cell to increase the longevity, tolerance to stress or reproductive capacity of said cell. LAG1 polypeptides used in the present methods for increasing cellular longevity and tolerance to stress include both wild type and mutant polypeptides. The wild type LAG1 polypeptide, e.g. SEQ ID NO:2, is preferably overexpressed later in the life of the cell or the organism, which in yeast, is after about 10 generations. In a preferred embodiment, a mutant polypeptide lacking the life-span limiting domain or having the life span extending domain is used.

As is known to the skilled artisan, high levels of overexpression of many gene products can adversely affect the host cell. Hence, such high expression levels are avoided and moderate levels of LAG1 expression are used. The level of LAG1 expression used in accordance with the present invention is sufficient to avoid adverse effects of overexpression and achieve increased longevity and/or tolerance to stress. Such increase in longevity, reproductive capacity and tolerance to cellular stress in eukaryotic cells are achieved through balanced and controlled expression by techniques familiar to the skilled artisan.

In one embodiment, expression of full length or wild type LAG1 polypeptide in a eukaryotic cell is from the natural LAG1 promoter endogenous to the cell. Similarly, LAG1 is expressed from a natural promoter which has been mutated or modulated, e.g. by binding an exogenously added transcription factor or an antisense oligonucleotide which can control LAG1 transcription. Therefore, nucleic acids encoding factors which control the transcription or translation of LAG1 polypeptides can be provided to achieve increased expression, for example, GCN4 protein and regulatory complex 2 (RC2). These are known transcriptional regulators which may bind to LAG1 DNA and thereby effect its transcription (see, Hinnebusch 1983 *Proc. Natl. Acad. Sci. USA* 80: 5374–78; Arcangioli, 1985 EMBO J. 4: 2627–33 and references cited therein).

Alternatively, LAG1 expression in a eukaryotic cell is from a heterologous promoter which has been operably linked to a nucleic acid encoding the LAG1 gene product. Such recombinant expression can therefore, be in addition to any LAG1 expression which may be occurring endogenously.

Accordingly, expressed gene products contemplated by the present invention include recombinant and non-recombinant gene products. As used herein a recombinant gene product is a gene product expressed from a nucleic acid which has been isolated from its natural source. Recombinant gene products are expressed from an isolated cDNA, mRNA or genomic DNA. In contrast, non-recombinant, or native, gene products are expressed from nucleic acids naturally present in the host cell.

To achieve recombinant expression of wild type and mutant LAG1 polypeptides, a nucleic acid encoding such a polypeptide is placed into an expression vector. Such an expression vector minimally contains a segment which can effect expression of the polypeptide when the segment is operably linked to a nucleic acid encoding the polypeptide. However, such an expression vector can also contain additional elements like origins of replication, selectable markers, transcription or termination signals, centromeres, autonomous replication sequences, and the like.

As used herein, an expression vector is a replicable or a non-replicable expression vector. A replicable expression vector can replicate either independently of host cell chromosomal DNA or with the host cell chromosomal DNA by virtue of integration therein. Upon integration into host cell chromosomal DNA, such an expression vector can lose some structural elements but retains the nucleic acid encoding the LAG1 polypeptide and a segment which can effect expression of the polypeptide. Therefore, the expression vectors of the present invention are chromosomally integrating or chromosomally nonintegrating expression vectors.

Moreover, the present expression vectors can replicate in one host cell type, e.g., *Escherichia coli*, and undergo little or no replication in another host cell type, e.g., a eukaryotic host cell, so long as an expression vector permits expression of the present LAG1 polypeptides in a selected host cell type.

Expression vectors as described herein include DNA or RNA molecules engineered for controlled expression of a desired gene product which include nucleic acid segments operably linked to nucleic acids encoding such gene products. Operably linked in this context means that such segments can effect expression of nucleic acids encoding the present gene products. These nucleic acid segments include promoters, enhancers, upstream control elements, transcription factors or repressor binding sites, termination signals and other elements which can control gene expression in the contemplated host cell. Preferably the vectors are plasmids, bacteriophages, cosmids, artificial chromosomes or viruses.

Sambrook et al. 1989 Molecular Cloning: A Laboratory Manual, Vols. 1–3, Cold Spring Harbor Press, Cold Spring Harbor, N.Y.; Goeddel, D. V. (Ed.) 1990, Gene Expression Technology, *Methods in Enzymology*, Vol 185, Academic Press; Perbal, B. 1988, *A Practical Guide to Molecular Cloning*, John Wiley & Sons, Inc.; and Romanos et al. 1992, *Yeast* 8: 423–488, provide detailed reviews of vectors into which a nucleic acid encoding the present LAG1 polypeptides can be inserted and expressed.

Expression vectors of the present invention function in eukaryotic cells, including yeast and mammalian cells. Yeast vectors can include the yeast 2µ circle and derivatives thereof, yeast plasmids encoding yeast autonomous replication sequences, yeast minichromosomes, any yeast integrating vector and the like. A comprehensive listing of many types of yeast vectors is provided in Parent et al. (1985 Yeast 1: 83–138).

Mammalian vectors can include SV40 based vectors, polyoma based vectors, retrovirus based vectors, Epstein-Barr virus based vectors, papovavirus based vectors, bovine papilloma virus (BPV) vectors, vaccinia virus vectors, baculovirus insect vectors and the like. Muzyczka (ed. 1992 *Curr. Top. Microbiol. Immunol.* 158:97–129) provides a comprehensive review of eukaryotic expression vectors.

Control of gene expression as used herein includes the ability to regulate expression both positively and negatively (i.e., turning gene expression on or off) to obtain the desired level of expression.

Elements or nucleic acid segments capable of effecting expression of a gene product include promoters, enhancer elements, upstream activating sequences, transcription termination signals and polyadenylation sites. All such promoter and transcriptional regulatory elements, singly or in combination, are contemplated for use in the present expression vectors. Moreover, genetically-engineered and mutated regulatory sequences are also contemplated herein.

Promoters are DNA sequence elements for controlling gene expression. In particular, promoters specify transcription initiation sites and can include a TATA box and upstream promoter elements.

Yeast promoters are used in the present expression vectors when a yeast host cell is used. Such yeast promoters include the GDP, GAL1, PGK, GAP, TPI, CYC1, ADH2, PHO5, CUP1, MFα1, MFα2 and related promoters. Romanos et al. (1992 Yeast 8: 423–488) provide a review of yeast promoters and expression vectors.

Higher eukaryotic promoters which are useful in the present expression vectors include promoters of viral origin, such as the baculovirus polyhedron promoter, the vaccinia virus hemagglutinin (HA) promoter, SV40 early and late promoter, the herpes simplex thymidine kinase promoter, the Rous sarcoma virus LTR, the Moloney Leukemia Virus LTR, and the Murine Sarcoma Virus (MSV) LTR. Moreover, the present invention contemplates cellular promoters which may be cell specific or developmentally regulated. Sambrook et al. (1989) and Goeddel (1990) review higher eukaryote promoters.

Preferred promoters of the present invention include inducible promoters, i.e. promoters which direct transcription at an increased or decreased rate upon binding of a transcription factor. Transcription factors as used herein include any factor that can bind to a regulatory or control region of a promoter and thereby affect transcription. The synthesis or the promoter binding ability of a transcription factor within the host cell can be controlled by exposing the host to an inducer or removing an inducer from the host cell medium. Accordingly to regulate expression of an inducible promoter, an inducer is added or removed from the growth medium of the host cell. Such inducers can include sugars, phosphate, alcohol, metal ions, hormones, heat, cold and the like. For example, commonly used inducers in yeast are glucose, galactose, and the like.

The expression vectors of the present invention can also encode selectable markers. Selectable markers are genetic functions that confer an identifiable trait upon a host cell so that cells transformed with a vector carrying the selectable marker are distinguished from non-transformed cells. Inclusion of a selectable marker into a vector can also be used to ensure that genetic functions linked to the marker are retained in the host cell population. Such selectable markers can confer any easily identified dominant trait, e.g. drug resistance, the ability to synthesize or metabolize cellular nutrients and the like.

Yeast selectable markers include drug resistance markers and genetic functions which allow the yeast host cell to synthesize essential cellular nutrients, e.g. amino acids. Drug resistance markers which are commonly used in yeast include canavanine (CAN$^s$), G418 (geneticin) and the like. Genetic functions which allow the yeast host cell to synthesize essential cellular nutrients are used with available yeast strains having auxotrophic mutations in the corresponding genomic function. Common yeast selectable markers provide genetic functions for synthesizing leucine (LEU2), tryptophan (TRP1), uracil (URA3), histidine (HIS3), lysine (LYS2) and the like.

Higher eukaryotic selectable markers can include genetic functions encoding an enzyme required for synthesis of a required nutrient, e.g. the thymidine kinase (tk), dihydrofolate reductase (DHFR), uridine (CAD), adenosine deaminase (ADA), asparagine synthetase (AS) and the like. The presence of some of these enzymatic functions is also identified by exposing the host cell to a toxin which is inactivated by the enzyme encoded by the selectable marker. Moreover drug resistance markers are available for higher eukaryotic host cells, e.g. aminoglycoside phosphotransferase (APH) markers are frequently used to confer resistance to kanamycin, neomycin and geneticin, and hygromycin B phosphotransferase (hyg) confers resistance to hygromycin in higher eukaryotes. Some of the foregoing selectable markers can also be used to amplify linked genetic functions by slowly adding the appropriate inhibitor for the enzyme encoded by markers such as DHFR, CAD, ADA, AS and others.

Therefore the present expression vectors can encode selectable markers which are useful for identifying and maintaining vector-containing host cells within a cell population present in culture. In some circumstances selectable markers can also be used to amplify the copy number of the expression vector.

After inducing transcription from the present expression vectors to produce an RNA encoding a LAG1 polypeptide, the RNA is translated by cellular factors to produce the gene product.

In yeast and other eukaryotes, translation of a messenger RNA (mRNA) is initiated by ribosomal binding to the 5' cap of the mRNA followed by migration of the ribosome along the mRNA to the first AUG start codon where polypeptide synthesis can begin. Expression in yeast and mammalian cells generally does not require specific number of nucleotides between a ribosomal-binding site and an initiation codon, as is sometimes required in prokaryotic expression systems. However, for expression in a yeast or a mammalian host cell, the first AUG codon in an mRNA is preferably the desired translational start codon.

Moreover, when expression is performed in a yeast host cell the presence of long untranslated leader sequences, e.g. longer than 50–100 nucleotides, can diminish translation of an mRNA. Yeast mRNA leader sequences have an average length of about 50 nucleotides, are rich in adenine, have little secondary structure and almost always use the first AUG for initiation (Romanos et al. 1992; and Cigan et al. 1987 Gene 59: 1–18). Since leader sequences which do not have these characteristics can decrease the efficiency of protein translation, yeast leader sequences are preferably used for expression of LAG1 polypeptides in a yeast host cell. The sequences of many yeast leader sequences are known and are available to the skilled artisan, e.g. by reference to Cigan et al. (1987 *Gene* 59: 1–18).

In mammalian cells, nucleic acids encoding LAG1 gene products generally include the natural ribosomal-binding site and initiation codon because, while the number of nucleotides between transcription and translational start sites can vary, such variability does not greatly affect the expression of the polypeptide in a mammalian host. However, when expression is performed in a mammalian host cell, the first AUG codon in an mRNA is preferably the desired translational start codon.

In addition to the promoter, the ribosomal-binding site and the position of the start codon, factors which can effect the level of expression obtained include the copy number of a replicable expression vector. The copy number of a vector is generally determined by the vector's origin of replication and any cis-acting control elements associated therewith. For example, an increase in copy number of a yeast episomal vector encoding a regulated centromere is achieved by inducing transcription from a promoter which is closely juxtaposed to the centromere (Chlebowicz-Sledziewska et al. 1985 *Gene* 39: 25–31). Moreover, encoding the yeast FLP function in a yeast vector can also increase the copy number of the vector (Romanos et al.).

The skilled artisan has available many choices of expression vectors. For example, commonly available yeast expression vectors include pWYG-4, pWYG7L and the like. Goeddel (1990) provides a comprehensive listing of yeast expression vectors and sources for such vectors. Commercially available higher eukaryotic expression vectors include pSVL, PMSG, pKSV-10, pSVN9 and the like.

One skilled in the art can also readily design and make expression vectors which include the above-described sequences by combining DNA fragments from available vectors, by synthesizing nucleic acids encoding such regulatory elements or by cloning and placing new regulatory elements into the present vectors. Methods for making expression vectors are well-known. Overexpression methods are found in any of the myriad of standard laboratory manuals on genetic engineering (Sambrook et al., 1989; Goeddel, 1990 and Romanos et al. 1992).

After construction of the present expression vectors, such vectors are transformed into host cells where the LAG1 gene product is expressed. Methods for transforming yeast and higher eukaryotic cells with expression vectors are well known and readily available to the skilled artisan.

For example, expression vectors are transformed into yeast cells by any of several procedures including lithium acetate, spheroplast, electroporation and similar procedures. Such procedures are found in numerous references including Ito et al. (1983, *J. Bacteriol.* 153: 163), Hinnen et al. (1978 *Proc. Natl. Acad. Sci. U.S.A.* 75: 1929) and Guthrie et al. (1991 Guide to Yeast Genetics and Molecular Biology, in *Methods In Enzymology*, vol. 194, Academic Press, New York).

Yeast host cells which are used with yeast replicable expression vectors include any wild type or mutant strain of yeast, for example, derived from *Saccharomyces cerevisiae*, Candida, Kluyveromyces, *Hansenula polymorpha, Pichia pastoris, Schizosaccharomyces pombe, Yarrowia lipolytic* and related species of yeast. In general, preferred mutant strains of yeast are strains which have a genetic deficiency that is used in combination with a yeast vector encoding a selectable marker. Many types of yeast strains are available from the Yeast Genetic Stock Center (Donner Laboratory, University of California, Berkeley, Calif. 94720), the American Type Culture Collection (12301 Parklawn Drive, Rockville, Md. 20852, hereinafter ATCC), the National Collection of Yeast Cultures (Food Research Institute, Colney Lane, Norwich NR4 7UA, UK) and the Centraalbureau voor Schimmelcultures (Yeast Division, Julianalaan 67a, 2628 BC Delft, Netherlands).

Mammalian host cells can also be transformed with the present expression vectors by a variety of techniques including transfection, infection and other transformation procedures. For example, transformation procedures include calcium phosphate-mediated, DEAE-dextran-mediated or polybrene-mediated transformation, protoplast or liposomal fusion, electroporation, direct microinjection into nuclei and the like. Such procedures are provided in Sambrook et al. and the references cited therein.

Tissue culture cells that are used with eukaryotic expression vectors can include primary cells and cell lines as well as immortalized cell lines. For example, cell lines contemplated by the present invention include WI38 cells, IMR9 cells, VERO cells, MRC-5 cells, SCV-1 cells, COS-1 cells, CV-1 cells, LCC-MK$_2$ cells, NIH3T3 cells, CHO-K1 cells, mouse L cells, HeLa cells, *Antheraea eucalypti* moth ovarian cells, *Aedes aegypti* mosquito cells, *S. frugiperda* cells and other cultured cell lines known to one skilled in the art. Such host cells are also obtained from the American Type Culture Collection (12301 Parklawn Drive, Rockville, Md. 20852, hereinafter ATCC).

In another embodiment the present invention provides methods for increasing the longevity or tolerance to stress of a eukaryotic cell, which includes administering to a cell a pharmaceutically effective amount of a LAG1 wild type, mutant, or derivative polypeptide or a LAG1 polypeptide lacking the life span limitation domain. In one embodiment, such polypeptides can have SEQ ID NO:2 or SEQ ID NO:4.

A further aspect of this invention provides pharmaceutical compositions containing the subject LAG1 nucleic acids, oligonucleotides or polypeptides with a pharmaceutically acceptable carrier. In particular, these nucleic acids, oligonucleotides and polypeptides are provided in a therapeutically effective amount of about 0.1 μg to about 100 mg per kg of body weight per day, and preferably of about 0.1 μg to about 10 mg per kg of body weight per day. Dosages are readily determined by one of ordinary skill in the art and formulated into the subject pharmaceutical compositions.

As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The subject nucleic acids, oligonucleotides and polypeptides may be administered topically or parenterally by, for example, by osmotic pump, intravenous, intramuscular, intraperitoneal subcutaneous or intradermal route. When suitably protected, the present nucleic acids, oligonucleotides and polypeptides can be orally administered. When topical administration is contemplated the subject nucleic acids, oligonucleotides and polypeptides may be incorporated into a cream, solution or suspension. For oral administration, nucleic acids, oligonucleotides and polypeptides may be protected by enclosure in a gelatin capsule. Nucleic acids, oligonucleotides and polypeptides may be incorporated into liposomes or liposomes modified with polyethylene glycol for parenteral administration. Incorporation of additional substances into the liposome, for example, antibodies reactive against membrane proteins found on specific target cells, can help target LAG1 nucleic acids, oligonucleotides and polypeptides to specific cell types.

Moreover, the present invention contemplates administering the subject nucleic acids, oligonucleotides and polypeptides with an osmotic pump providing continuous infusion, for example, as described in Ratajczak et al. (1992, Proc. Natl. Acad. Sci. USA 89:11823-11827). Such osmotic pumps are commercially available, e.g., from Alzet Inc (Palo Alto, Calif.).

Parenteral administration, e.g. in a liposomal carrier, is preferred.

The present invention further contemplates an article of manufacture comprising a packing material and a pharmaceutical agent contained within the packing material. The pharmaceutical agents contemplated herein include the subject LAG1 nucleic acids, oligonucleotides and polypeptides. The packing material used to contain the pharmaceutical agent can include glass, plastic, metal or any other suitably inert material.

In accordance with the present invention, the LAG1 polypeptides or peptides thereof are used to generate an anti-LAG1 antibody. Such antibodies can be monoclonal or polyclonal. When monoclonal antibodies against LAG1 are produced, the present invention also includes the hybridoma cells which produce these antibodies.

Polyclonal antibodies against LAG1 can be obtained by preferably using pure a LAG1 polypeptide or peptide as immunogen. However, anti-LAG1 monoclonal antibodies can be produced using either pure or impure preparations of polypeptides or peptides because hybridoma cell lines secreting antibodies reactive with non-LAG1 antigens can be eliminated during screening and isolation of hybridomas.

Antibodies can be obtained using the entire LAG1 polypeptide as an antigen or by using short LAG1-specific peptides as antigens. If peptides are selected as immunogens, peptide sequences can be screened before use for a likelihood of being reactive only with anti-LAG1 antibodies by searching known protein sequence data banks for homology with known proteins.

Polyclonal antibodies directed against the LAG1 polypeptides are prepared by injection of a suitable laboratory animal with an immunoeffective amount of a LAG1 polypeptide or peptide. Suitable animals include rabbits, mice, rats, goats and chimpanzees. Rabbits are generally preferred animals for producing polyclonal antibodies. Immunoglobulin fractions can be isolated from polyclonal sera by any of the known immunoadsorbent techniques. Techniques for obtaining polyclonal antibodies are available, for example, in Harlow, et al. *Antibodies: A Laboratory Manual*, Cold Spring Harbor Press, 1988.

Monoclonal antibodies are generally preferred over polyclonal antibodies because large quantities of antibodies, all of similar reactivity, can be obtained. The preparation of hybridoma cell lines capable of secreting monoclonal antibodies is done by any procedure available in the art. In general, hybridoma cell lines are produced by fusing an immortalized cell with an antibody producing lymphocyte. This can be done by known techniques, for example, as provided in Harlow, et al. *Antibodies: A Laboratory Manual*, Cold Spring Harbor Press, 1988; or Douillard, et al. "Basic Facts About Hybridomas", in *Compendium of Immunology Vol. II*, L. Schwartz (Ed.), 1981.

The following examples further illustrate the invention.

EXAMPLE 1

EXPERIMENTAL PROCEDURES
Strains and Growth Conditions

Three strains of S. cerevisiae were used: SP1 (MATa, leu2, ura3, trpl, ade8, can1, his3, gal2); X2180-1A (MATa, SUC2, mal, mel, gal2, CUP1) from the Yeast Genetic Stock Center (Berkeley, Calif.); and YPHDF-1A (MATa, ade2-101$^{ochre}$, his3-Δ200, leu2-Δ1, lys2-801$^{amber}$, trpl-Δ 63, ura3-52). Strain YPHDH-1A is a haploid strain derived from diploid strain YPH501.

Diploid YPH501 was sporulated, a tetrad dissected, and a MATα strain was selected. The haploid MATα strain was transformed with the pGALHO plasmid, a single-copy plasmid with the URA3 selectable marker and the HO gene under the control of the GAL1-GAL10 promoter. Mating-type switch was induced in synthetic medium lacking uracil, using 5% galactose as a carbon source to induce HO expression. Cells of opposite mating type mated, and the zygotes were isolated by micromanipulation on YPD agar. The resulting diploid cells were grown on non-selective medium at 30° C. for 2 days, to cure the cells of the plasmid. The diploid cells (YPHDF-1) were sporulated, and tetrads were dissected by micromanipulation on YPD agar. One of the spores was designated as the strain YPHDF-1A. For meiotic mapping, the strains BZ34-801C (MATa, ade2-1, arg4, gal2, his5-2, leu, lysl, metl, pet1, thr1, trp5-48, ura3) and STX339-1C (MATa, adel, cdc12, gall, his7, leu1, lys2, met14, tyr1, ura1) from the Yeast Genetic Stock center (Berkeley, Calif.) were used.

Yeast strains were cultured in YPD medium (2% peptone, 1% yeast extract, 2% glucose) on a shaker at 30° C. Life span determinations were performed on YPD. To obtain age-synchronized cells, YPDG medium (2% peptone, 1% yeast extract, 0.04% glucose, 1.6% glycerol) was used for growing cells instead of YPD. During meiotic mapping studies and transformant selection, cells were plated on synthetic complete medium (SC) (Sherman et al., 1986 *Methods in Yeast Genetics*, Cold Spring Harbor Laboratory Press, Cold Spring Harbor, N.Y.) lacking the appropriate nutrients. In certain studies synthetic deficient medium (SD) (Sherman et al.) was used.

*Escherichia coli* DH5αF' was used for molecular cloning, and *E. coli* P2392 (Stratagene), a P2 lysogen of LE392 [hsdR514 ($r_k$-, $m_k$+), supE44, supF58, lacY1 or Δ(lacIZY), galK2, galT22, metB1, trpR55] was used to select recombinant phages. *E. coli* LE392 (Stratagene) was used to titer the phage. Bacteria was grown in LB medium (1% tryptone, 0.5% yeast extract, 1% NaCl) on a shaker at 37° C. Cells that were transformed with the plasmid pUC118 or pUC119 or their derivatives were selected on medium containing 100 μg/ml of ampicillin. Solid media contained 1.5% agar.

Construction of Meiotic Mapping Strains

Figure 1:
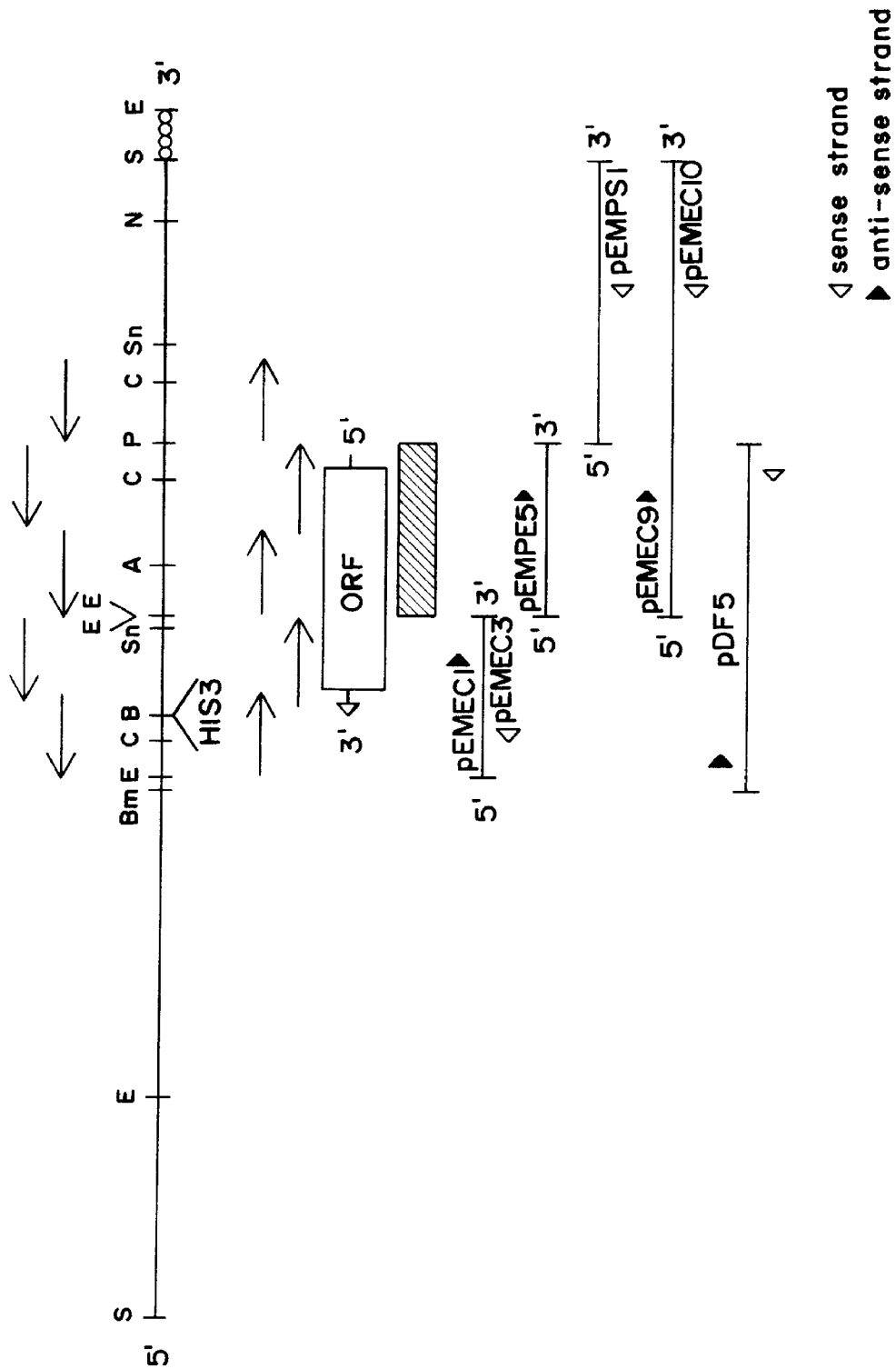
FIG. 1 depicts a restriction map of a 6 kilobase (kb) SstI fragment containing the Saccharomyces cerevisiae LAG1 gene. The LAG1 coding region (ORF) is provided with an arrow indicating the direction of transcription. A deletion mutation was made by replacing the PstI-EcoRI fragment (hatched box) with an integrative plasmid. To mark the gene for meiotic mapping, a 1.8 kb HIS3 DNA fragment was inserted at the BglII site. Arrows above and below the restriction map represent stretches of sequence obtained from the indicated clones. Clones pEMPE5, pEMPS1 and pDF5 were generated by inserting the indicated fragments in the multiple cloning site of the pUC118 vector. Clones pEMEC1, pEMEC3, pEMEC9 and pEMEC10 were generated by subcloning the indicated fragments in both orientations within pUC119. The restriction map was generated using enzymes: E=EcoRI; Bm=BamHI; B=BglII; A=ApaI; P=PstI; C=ClaI; N=NcoI; S=SstI; Sn=SnaBI.

Standard procedures in yeast genetics were used throughout (Guthrie et al. 1991 *Guide to Yeast Genetics and Molecular Biology*, Academic Press, Inc., San Diego, Calif.). A 1.8-kb BamHI fragment containing the entire HIS3 gene (flanked by parts of the PET56 and DED1 genes) (Struhl, 1985 *Nucl Acids Res.* 13: 8587–8601) was inserted into a unique BglII site in the clone pEMEC1, containing the 0.8-kb EcoRI fragment cloned in the plasmid pUC119 (FIG. 1). The yeast DNA was excised with EcoRI and used to transform the haploid strain SP1 using the lithium acetate procedure (Ito et al., 1983 *J. Bacteriol.* 153: 163–68). This yielded SP1 MATa LAG1::HIS3. The MATα strain XDF5-2B, isogenic to SP1 MATa LAG1:HIS3, was isolated by transforming the SP1 MATa LAG1::HIS3 strain with plasmid pGALHO as described above. One of the resulting MATα haploid colonies was designated strain XDF5-2B. The strain XDF7-6C (MATa, ade, arg4, cdc12, his3, leu, thrl, trp, ura) was derived as follows. BZ34-801C and STX339-1C were each mated with a MATα strain isogenic to SP1, obtained by pGALHO-induced mating-type switch as described above. The diploid cells were sporulated and tetrads dissected by micromanipulation on YPD agar. A BZ34-801C-derived haploid (MATa) was mated with an STX339-1C-derived haploid (MATα). The diploid cells of this final mating were sporulated and tetrads dissected. One of the MATa haploid colonies from this final mating was designated XDF7-6C.

Construction of a Yeast DNA Library

A yeast DNA library was constructed as described by Nasmyth et al. (1980 *Proc. Natl. Acad. Sci. USA.* 77: 2119–23). Yeast genomic DNA was digested with Sau3A1 (Bethesda Research Laboratories) to yield fragments of about 12 kb. The digested fragments were fractionated by centrifugation in 5–20% sucrose gradients. Fractions that yielded fragments of 10 kb to 14 kb were pooled, and the DNA was concentrated by ethanol precipitation. The DNA fragments (0.4 µg) were then ligated to 1 µg of predigested (BamHI and EcoRI) lambda EMBL3 arms that were obtained from Stratagene using T4 DNA ligase, according to instructions of the manufacturer. Half of the ligation mixture was packaged using the Gigapack Gold packaging extract (Stratagene). The resulting phages were then plated on *E. coli* P2392 to selected recombinant phage. A total of $1.25 \times 10^5$ recombinant plaques were obtained. The average insert size was 12 kb. The recombinants were amplified once using LE392 cells, and they were stored as plate lysates at –70° C. in 1 ml aliquots after addition of dimethyl sulfoxide to 0.7%.

Isolation of S. cerevisiae LAG1

The LAG1 gene was isolated in a 12-kb insert obtained from the lambda EMBL3 genomic DNA library. A 6-kb SstI fragment from this clone, (FIG. 1), which was found to contain the gene by Southern analysis using the originally isolated partial clone as a probe (Egilmez et al., 1989 *J. Biol. Chem.* 264: 14312–17), was subcloned into the plasmid pUC119. From this construct, various subclones were obtained by the isolation and subcloning of different restriction fragments into the multiple cloning sites of pUC118 and pUC119 (FIG. 1). The 0.8-kb EcoRI fragment was inserted in both orientations in the vector pUC119 to obtain the clones pEMEC1 and pEMEC3. Since the 6-kb SstI fragment was inserted in the multiple cloning site of the pUC119 vector, an EcoRI site was present adjacent to the SstI site. Using this EcoRI site and the EcoRI site located within the insert, a 2.5-kb fragment was removed and inserted into the multiple cloning site of the pUC119 vector in both orientations to obtain clones pEMEC9 and pEMEC10. The PstI-EcoRI fragment containing the coding region of the LAG1 gene was inserted in the multiple cloning site of the pUC118 vector to obtain the clone pEMPE5. The PstI-SstI fragment encompassing the upstream region of the LAG1 gene was subcloned into the vector pUC118 as well to generate pEMPS1, while the PstI-BamHI fragment containing the entire open reading frame in pUC118 was designated pDF5.

DNA Sequence and Sequence Analysis

The LAG1 gene was sequenced by cloning a series of restriction fragments into either pUC118 or pUC119 (Viera et al. 1987 *Meth. Enzymol.* 153: 3–11). Standard recombinant DNA techniques were used throughout (Ausubel et al., 1987 *Current Protocols in Molecular Biology*, John Wiley and Sons, Inc., New York, N.Y.). Single-stranded DNA was prepared by infecting *E. coli* DH5αF' cells carrying the specific plasmids with the defective phage M13KO7, resulting in production of M13 phage containing pUC118 or pUC119 DNA strands. The sequence of both strands of the yeast DNA inserts was determined by using the Sequenase 2.0 dideoxy-chain termination kit (U.S. Biochemical Corp.). Sequencing primers were obtained from commercial sources (Oligos Etc., Inc.) or prepared in the Biotechnology Core Laboratories, LSU Medical Center. Sequence analysis, homology searches, comparisons, pattern searching and structure prediction were performed by using programs in the PCGENE analysis package (Intelligenetics).

Southern and Northern Blots

Total yeast DNA was prepared from 10 ml cultures of mid-logarithmic phase yeast cells essentially as described by Ausubel et al. (1987 *Current Protocols in Molecular Biology*, John Wiley and Sons, Inc. New York, N.Y.). Zymolyase 100T (Seikagaku Kogyo Co.) was utilized to remove the yeast cell wall. Two procedures were used for the extraction and purification of plasmid DNA from bacterial cells. One of the procedures involved cell lysis with lysozyme followed by banding in isopycnic CsCl gradients containing ethidium bromide (Jazwinski et al., 1982 *Proc. Natl. Acad. Sci. USA* 79: 3428–32). This method was suitable for the large scale isolation of plasmid DNA. A rapid alkaline lysis method was used for small-scale minipreps (Kraft et al., 1988 Biotechniques 6: 549–46). To obtain total RNA, the yeast cell wall was removed by Zymolyase, and the cells were lysed with guanidine isothiocyanate (Bethesda Research Laboratories) as described by Egilmez et al. (1989 *J. Biol. Chem.* 264: 14312–17). The RNA was purified by banding in isopycnic cesium trifluoroacetate (Pharmacia LKB Biotechnology, Inc.) gradients.

Total DNA (3–4 µg) was digested with different restriction enzymes (Bethesda research Laboratories) and electrophoresed on a 0.7% agarose gel in TBE (0.09M Tris, 0.09M borate, 0.002M EDTA, pH 8.0) buffer. The DNA was transferred to nitrocellulose (Schleicher and Schuell) by utilizing the Posiblot pressure blotter (Stratagene). Prehybridization and hybridization were performed in 6× SSPE (1× SSPE=0.18M NaCl, 10 mM sodium phosphate pH7.7, 1 mM EDTA) with 5× Denhardt's solution (1× Denhardt's solution=0.02% Ficoll, 0.02% polyvinylpyrrolidone, and 0.02% bovine serum albumin), 0.1% SDS, 50% formamide, and 100 µg/ml denatured salmon sperm DNA. Prehybridization was performed for 4 h and hybridization for 16 h at 42° C. The probe, an 868-base pair ClaI-EcoRI fragment containing the open reading frame of the gene (FIG. 1) was prepared by random oligonucleotide-primed DNA synthesis using a random primer kit (U.S. Biochemical corp.) and [α-$^{32}$P]dATP, and added to the hybridization solution. The membrane was washed with 2× SSC (1× SSC=0.15M NaCl, 15 mM sodium citrate, pH 7.0) containing 0.2% SDS twice at 60° C. Autoradiography was performed with an intensifying screen at –70° C. To search for similar DNA sequences in other organisms, DNA was obtained from human, galago, mouse, bovine, and salmon sources. Eight micrograms of DNA from each source were digested with HindIII. The digested DNA was loaded on a 0.8% agarose gel, electrophoresed and then transferred to nitrocellulose. Prehybridization and hybridization were performed as described above, except 35% formamide was used in the solution. The membrane was washed twice, 20 min per wash, with 2× SSC containing 0.2% SDS at 30° C. The membrane was then subjected to autoradiography at −70° C. with intensifying screens.

Equivalent amounts (5 μg) of total RNA from yeast cells of different ages were denatured in 50% formamide/2.2M formaldehyde and electrophoresed in a 1.2% agarose gel in the presence of formaldehyde. The RNA was transferred to Zeta-probe (Bio-Rad Laboratories) membranes by capillary action in TE (10 mM Tris-HCl, 1 mM EDTA, pH 8.0) buffer. The membranes were prehybridized, hybridized and washed under conditions described previously (Egilmez et al. 1989 *J. Biol. Chem.* 264: 14312–17). A $^{32}$P-labeled, 1,052-base pair PstI-EcoRI fragment encompassing the coding region of the LAG1 gene (FIG. 1) was used as a probe. After washing, the membranes were exposed to a phosphor screen in an imaging plate (Molecular Dynamics) for one to two days at room temperature. The imaging plates were scanned using the Molecular Dynamics 400E phosphorimager. Analysis was performed using Molecular Dynamics ImageQuant software, version 3.15 (Johnson et al., 1990 *Electrophoresis* 11: 355–60). The blots were then reprobed with a clone of an anonymous gene whose expression remains constant during the life span (Egilmez et al., 1989 *J. Biol. Chem.* 264: 14312–17) to normalize for the amount of RNA loaded in each lane.

S1-Mapping

A primer 5'-GCATTAACAACTAACCTATCG-3' (Biotechnology Core Laboratories, LSU Medical Center) complementary to nucleotides +47 to +27 of the LAG1 gene was labeled at the 5' end with [γ-$^{32}$P]ATP using T4 polynucleotide kinase (Bethesda Research Laboratories). The oligonucleotide was hybridized to the LAG1 gene sense strand generated from the clone pEMEC10, containing the 2.5-kb EcoRI fragment (FIG. 1) in a pUC119 vector and extended using the Klenow fragment of *E. coli* DNA polymerase I (Bethesda research Laboratories). The double-stranded product was cut with the restriction enzyme PstI to generate a 200-bp fragment. The synthesized strand was therefore complementary to the mRNA and was used as a probe to map the transcription start site. The probe was purified on an alkaline agarose gel and 5×10$^4$ Cerenkov counts of labeled probe were hybridized to 50 μg of total RNA to obtain a molar excess of probe over LAG1 mRNA (see Ausubel et al. 1987).

The probe:mRNA mixture was treated with either 165, 220, or 330 units of S1 nuclease (Bethesda research Laboratories) for 60 min at 30° C. to digest unhybridized portions of the probe. The buffer used was 0.28M NaCl, 4.5 mM ZnSO$_4$, and 50 mM sodium acetate, pH 4.5 buffer. As a control, 20 μg of tRNA were hybridized with an equal amount of probe, and the mixture treated with 330 units of S1 nuclease.

The S1-protected fragments were sized by separation on an 8% polyacrylamide-urea sequencing gel. A DNA sequencing ladder was run alongside the S1 reaction fragments. This ladder was obtained with the same primer and pEMEC10 single-stranded template used to generate the probe used above.

Primer Extension Analysis

Primer extension analysis was performed by using 50 μg of total RNA, the same primer that was utilized for the S1 mapping, and avian myeloblastosis virus reverse transcriptase (Molecular Genetic Resources, Tampa, Fla.) as described by Ausubel et al. (1987). Labeled products were subjected to electrophoresis on an 8% polyacrylamide-urea sequencing gel. A DNA sequencing ladder generated using the same primer and the single-stranded DNA from clone pEMEC10 was used to determine the size of the extended fragments.

Construction of a LAG1 Deletion

The strategy of obtaining a deletion involved cloning, in inverse orientation, regions flanking the segment of the gene that was to be deleted. The 806-bp EcoRI fragment spanning the 3' end of LAG1 (FIG. 1) was ligated into the EcoRI site of the multiple cloning site in the integrative plasmid pRS404 (Sikorski et al. 1989 *Genetics* 122: 19–27). The pRS404 vector possesses the TRP1 selectable marker permitting selection of a construct with the appropriate orientation of the 806-bp fragment. Next, the ends of the 1,339-bp SstI-PstI fragment encompassing the upstream region of the LAG1 gene were made blunt with T4 DNA polymerase. This blunt-ended fragment was ligated into the SmaI site in the multiple cloning site of a fresh pRS404 plasmid. A clone with the suitable orientation of the LAG1 DNA with respect to the PstI and SstI sites in the vector was selected. Cleavage of this clone with PstI and SstI generated a LAG1 fragment that was cloned directionally between the PstI and SstI sites of the first pRS404 construct, in the inverse orientation with regard to the 806-bp EcoRI fragment of LAG1. The plasmid DNA from this final clone was digested with the enzyme PstI to create a linear DNA fragment. This linear fragment contained the integrative vector, pRS404 (4,271 bp), flanked by 806 bp from the 3' end and downstream of the gene (EcoRI to EcoRI) and 1,339 bp of the upstream region of the LAG1 gene (SstI to PstI). This linear fragment was isolated and used to transform diploid YPHDF-1. The cells were then plated on synthetic medium lacking tryptophan to select for cells with the integrated DNA fragment. The net effect was to delete 1,151 bp of the gene encompassing the transcriptional and translational start sites. This deletion included 158 bp upstream of the translational start site and 993 bp of the coding region. Deletion of one copy of the gene was confirmed by Southern blot analysis. This heterozygote was sporulated, and MATa, LAG1Δ::TRP1 haploids were retained. The deletion had no apparent effect on the vegetative growth and division of haploid cells.

Age-Synchronized Cells

Age-synchronized yeast cells were prepared according to Egilmez et al. (1990 *J. Gerontol. Biol. Sci.* 45: B9–17). Virgin cells (last buds) were obtained after sonication of a stationary culture of 4×10$^8$/ml X2180-1A cells by rate-zonal sedimentation of the cells in 10–30% sucrose gradients. Two bands were observed in these gradients. The upper band representing the smaller, virgin cells having no bud scars was retained. Virgin cells were pooled and synchronized in YPD medium with 400 nM yeast mating pheromone α-factor (Sigma Chemical Co.) for 2 h at 30° C. These virgin cells (0-generation cells) were washed and then resuspended in YPDG medium.

To obtain older cells virgin cells were incubated at 30° C. until they divided synchronously twice, to reach a density of 1.2×10$^8$ cells/ml. Cells increased in size with each cell division. On rate-zonal sedimentation in sucrose gradients, two bands were observed. The lower band representing the two generation-old cells (cells that divided twice and had two bud scars) was collected.

The second generation-old cells were resuspended in YPDG medium at 2.5×10$^7$/ml and incubated at 30° C. for three synchronous generations. The cells were again separated by rate-zonal sedimentation. The lowest band, representing five-generation-old cells, was collected. An aliquot of 1×10⁸ cells was saved. These steps were reiterated to obtain 8-, 11-, 14-, and 18-generation-old cells. At each step of the procedure, the purity of the mother cells was easily determined by virtue of the large difference in their size and the size of their synchronously-generated daughters. Each aliquot was >95% pure. A number of criteria have been applied to assess the age and purity of the cells in these preparations (Egilmez et al., 1990), including the determination of the remaining life spans of cells in the preparations.

Life Span Determination

Life span determinations were performed at 30° C. using a micromanipulator attached to a Nikon Labphot microscope with a 40× long-distance objective (Egilmez et al. 1989 *J. Bacteriol.* 171: 37–42). A slab of YPD medium was cut and placed on a 1×3 inch glass slide. A loopfull of cells from a fresh colony was resuspended in sterile water and streaked along one edge of the slab. The slide was then placed upside down on a 1×3 inch chamber. Thirty to forty cells were used to initiate each life span determination. Individual cells were placed at marked, isolated spots on the agar slab with the aid of the micromanipulator. The buds that emerged from these cells after the first cell cycle ('virgin' cells) were counted as zero-generation cells. Their mothers were removed with the micromanipulator and discarded, and the life spans of these virgin cells were determined. With every cell division or generation, the emerging bud was removed, and the mother cell was scored one generation older. This process was continued until budding ceased. The generational age of the cell after division ceased was determined by the number of buds that emerged from that cell. At the end of their reproductive life spans, many cells lysed outright. Others remained intact for several days but did not form a colony or divide even once, indicating these cells were inviable. The actual cause of death is not known at present. In order to slow division and provide relief for the investigator, the cells were refrigerated during the night. This procedure does not alter the replicative life span, as measured by the number of cell divisions (Muller et al., 1980 *Mech. Ageing Dev.* 12:47–52). The Student's t test was used to compare mean life spans.

Phenotypic analysis

The colony-forming ability of strains with LAG1 deletion mutations was examined under different conditions. In every case, overnight cell cultures grown in YPD were diluted so that 200, 400 and 1000 cells could be spread on the appropriate agar plates. Duplicate plates were prepared and incubated at 30° C. After incubation, the number of colonies formed on each test plate was counted and compared to the number formed on control plates.

To examine the effect of temperature, a series of YPD agar plates was incubated a 4° C., 14° C., 23° C., 30° C. (control), 37° C., or 42° C. To study the effect of heat shock, the cells were heated to 55° C. for 2 minutes and then plated on YPD agar plates and incubated at 30° C. To examine pH sensitivity, the various strains were plated on YPD agar plates at pH 2, pH 4, pH 6 (control), pH 8 and pH 10. To examine the utilization of non-fermentable carbon sources, the cells were plated on YP supplemented with either 3% glycerol, 2% lactic acid, 2% ethanol, or 2% potassium acetate. Plates were incubated at 30° C. for a week. Differential utilization of fermentable carbon sources was examined by plating on YP with either 2% glucose (control), 2% galactose, 5% galactose, or 2% raffinose. These plates were incubated at 30° C. for 2–4 days.

The ability of the strains to mate was examined by transforming the cells with the plasmid pGALHO and selecting for URA⁺ cells. Cells from positive colonies were streaked on plates with SC medium and galactose, instead of glucose, to induce expression of the HO gene. These plates were incubated overnight. A loopfull of cells was then observed for the presence of zygotes.

To examine sporulation ability, diploid strains were plated on sporulation medium, and the number of tetrads formed after 4–6 days at 30° C. was compared with the parent strain.

To examine the ability of cells to withstand salinity, cellular growth was monitored after inoculating 5×10⁵ cells/ml into YPD media containing 0, 0.25M, 0.5M, 0.75M, 1M, 1.25M or 1.5M NaCl.

To examine the ability of cells to withstand nitrogen starvation 5×10⁵ cells/ml were incubated in YPD broth, SD medium without ammonium sulfate, and SD with ammonium sulfate. After two days at 30° C., cells were counted, diluted and plated on YPD medium to determine colony forming units.

To study the sensitivity of the different strains to caffeine, cells were plated on YPD containing either 5 mM, 10 mM, or 15 mM caffeine and incubated at 30° C. Colonies on these plates were compared to colonies growing on YPD plates lacking caffeine, to determine colony forming ability (viability) and the rate of colony formation.

EXAMPLE 2

ISOLATION AND CHARACTERIZATION OF THE LAG1 GENE

Isolation of the LAG1 Gene

A differential hybridization procedure was set up to screen for genes that are preferentially expressed in young or old cells as described in Egilmez et al. (1989 J. Biol. Chem. 264: 14312–17). This screen yielded several small clones.

One clone obtained in this fashion was selected for further characterization. The clone was isolated from a genomic library constructed in the plasmid pBR322 where the average size of the inserts was about 1 kb. Because only part of the gene was present in the original clone in pBR322, it was necessary to obtain a full-length clone. For this purpose, a genomic library was constructed in the vector lambda EMBL3. The average size of the inserts in the lambda EMBL3 library was 12 kb, increasing the probability of obtaining the gene in its entirety. Using a fragment of the original clone in pBR322 as a probe, four clones were obtained, with inserts averaging 12 kb in length. These clones were purified through secondary and tertiary screens.

The insert from one of these clones was restriction mapped and a 6-kb SstI restriction fragment was identified that hybridized to the original pBR322 clone. This fragment was subcloned into the pUC119 vector. A restriction map of this clone was constructed using several different restriction enzymes, as shown in FIG. 1. EcoRI restriction fragments of 2.5 kb and 0.8 kb hybridized to mRNA by Northern analysis. Therefore, these fragments contained parts of the coding region.

Sequence

To initiate the sequencing of the gene, various portions of the 6-kb SstI fragment to which the gene was localized were subcloned into the pUC118 and pUC119 vectors (FIG. 1). Sequencing was carried out by the dideoxy chain-termination method (Sanger et al., 1977), using single-stranded DNA generated from the subclones. To fill in gaps, primers were synthesized on the basis of the sequences obtained (FIG. 1). Both DNA strands were sequenced completely two times, and some portions were sequenced a third time.

Figure 2A:
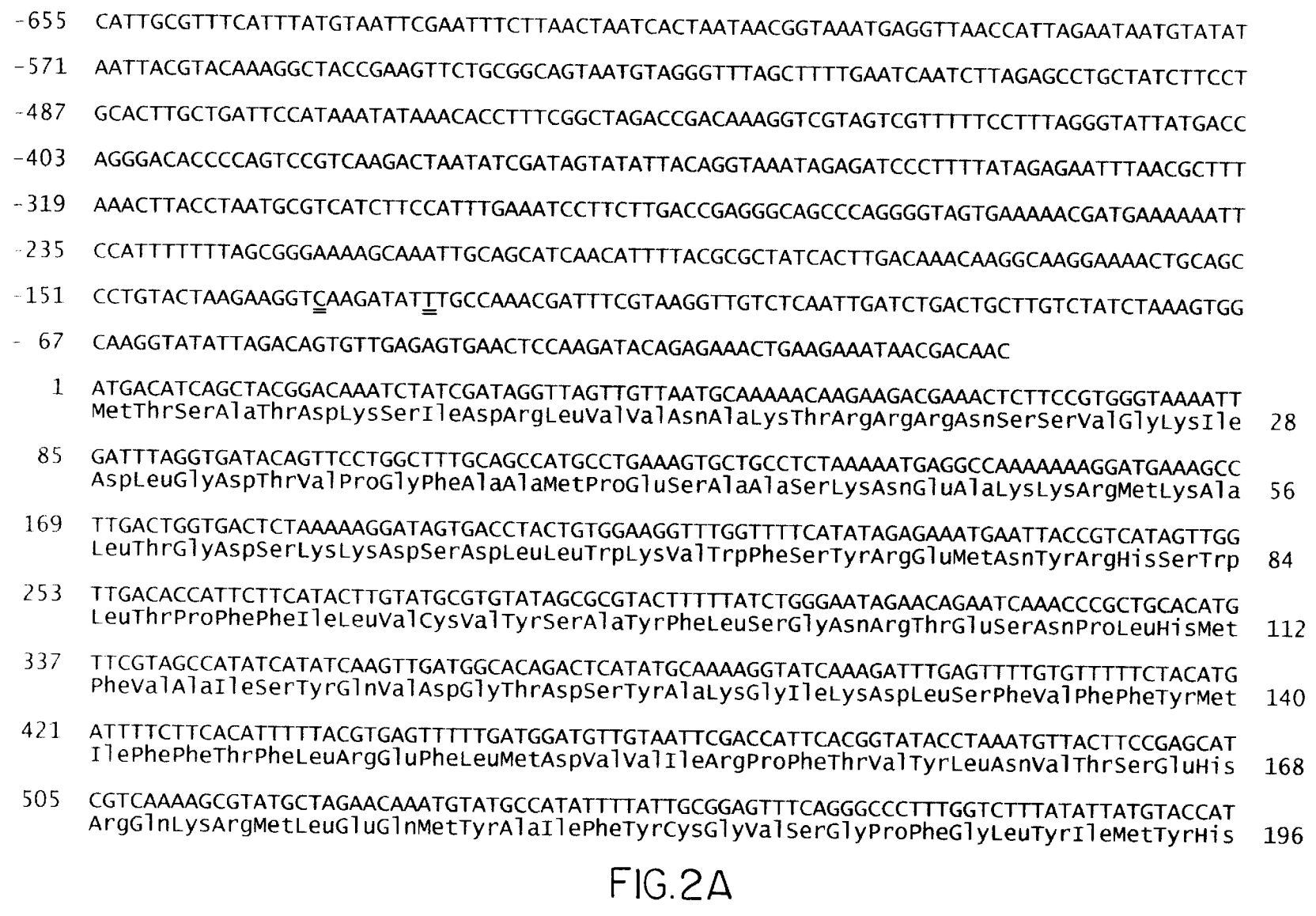

Analysis of the sequence reveals a single, long open reading frame of 1,233 bases (FIG. 2). The sequence context of the putative initiation codon, GACAACATGACA, is a suboptimal fit (67%) to the consensus sequence (A/T)A(A/C)A(A/C)AATGTC(T/C) of well-expressed yeast genes (Hamilton et al., 1987 Nucl. Acids. Res. 15:3581–93). This predicted initiation codon lies 127 bp and 135 bp downstream of the two transcriptional start sites, respectively. A second in-frame ATG, located at +118 is not likely to function as an initiation codon, because it has a poorer fit (58%) to the consensus sequence and is located far downstream of the transcriptional start sites. No intron consensus sequences were found within the gene. A transcription termination consensus sequence TAG * * * * TAGT followed by a pyrimidine-rich region was found at position +1,306, that is 70 bp downstream of the translational stop codon. This transcriptional termination sequence was similar but not identical to the consensus sequence of Zaret et al. (1982 Cell. 28:563–73).

The gene encodes a protein of 411 amino acids, when translation initiates a the first available start codon. The calculated molecular weight of the predicted protein is 48,454, with an isoelectric point of 9.19.

Figure 3A:
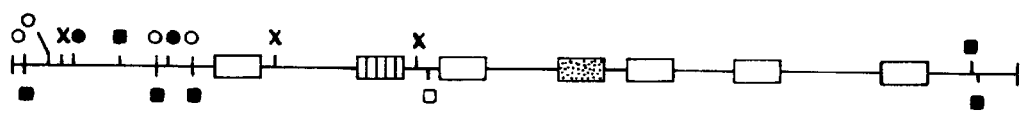
FIG. 3A provides a schematic representation of the S. cerevisiae LAG1 protein and its motifs. Predicted protein signatures are cAMP-(PK-A) and cGMP-(PK-G) dependent protein kinase phosphorylation sites (●); protein kinase C (PK-C)(○), casein kinase II(■), and tyrosine kinase phosphorylation sites (□); N-glycosylation sites (x). The membrane-spanning regions of the protein (open bars), region characterized as a hydrophobic surface domain (hatched bar), and globular regions of the protein (solid bar), as predicted by HELIXMEM, are indicated.
Figure 3B:
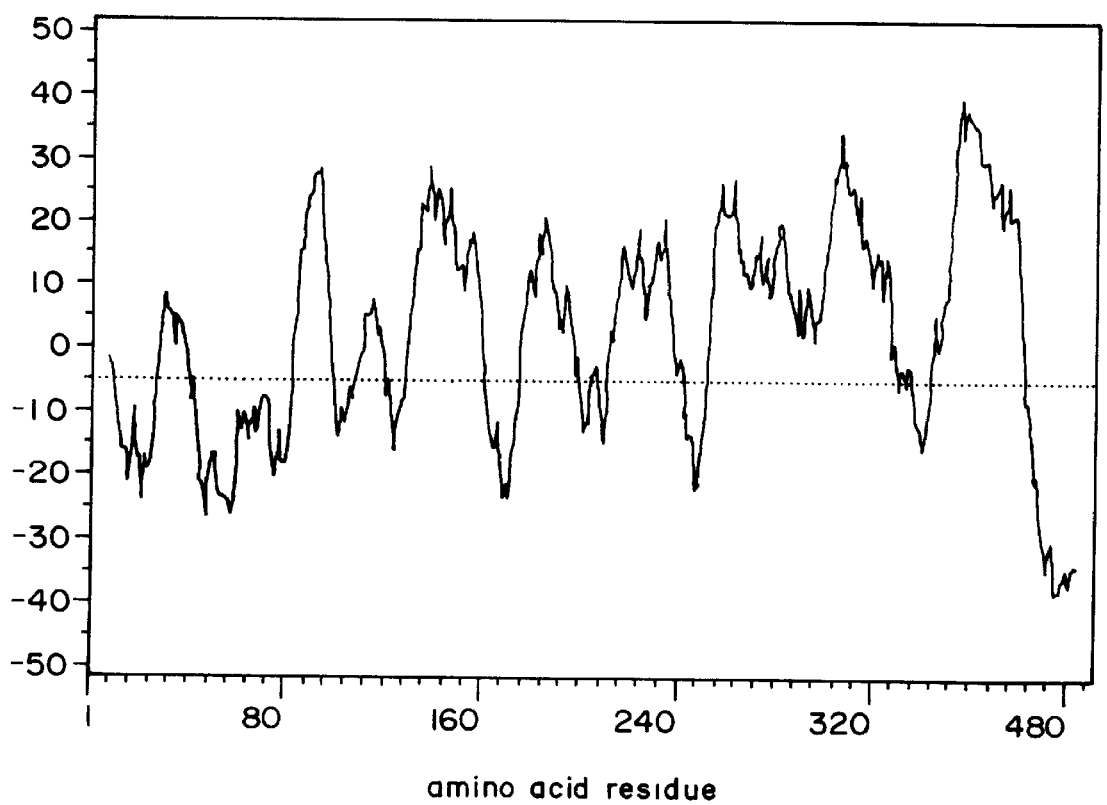
FIG. 3B depicts a hydropathy plot of the LAG1 gene product generated by the program SOAP, using a window size of 15 amino acids. The ordinate values refer to the hydropathy values of Kyte et al. (1982 J. Mol. Biol. 157: 105–32). Hydrophobicity increases above the horizontal, dotted line.

An analysis of the sequence of the predicted protein was done using the PROSITE program (Bairoch, 1990 PROSITE: A Dictionary of Protein Sites and Patterns, University of Geneva, Sixth Release) that identifies potential sites and signatures found in protein sequences. Clusters of potential phosphorylation sites close to the N-terminus and C-terminus of the protein were identified (FIG. 3A). Three different routines, RAOARGOS (Rao et al. 1986 Biochem. Biophys. Acta 869:197–214), HELIXMEM (Eisenberg et al., 1984 J. Mol. Biol. 179: 125–42), and SOAP (Kyte et al., 1982 J. Mol. Biol. 157: 105–32; Klein et al., 1985 Biochem. Biophys. Acta 815: 468–76), were utilized to determine potential transmembrane domains (FIG. 3A). These correspond to the hydrophobic regions of the protein observed on the hydropathy plot (FIG. 3B). Since no signal peptide, stop transfer sequences or signal peptidase recognition sequences were identified at the N-terminus of the protein, it appears that LAG1 polypeptides are not handled by the secretory pathway. No mitochondrial transit peptide consensus sequence (Gavel et al. 1990 Protein Eng. 4:33–37) was found either.

The sequence upstream of the initiation codon encompassing 655 bp was screened for DNA sequence motifs to which known regulatory proteins bind. A putative TATA-box element is present 62-bp 5' of the presumed ATG translational start codon. Also, the binding site of GCN4 also known as AAS3 (amino acid analog-sensitive) protein (Hinnebusch 1983 Proc. Natl. Acad. Sci. USA 80:5374–78), TGACT, was found at position –91 to –87. This protein is an activator of several genes under general control, and the core DNA-binding sequence is found at HIS1, HIS3, HIS4 and TRP5 promoters. The TATA box element and the binding site of the GCN4 protein are present downstream of the transcriptional start. The consensus sequence to which RC2 (regulatory complex 2) binds (Arcangioli, 1985 EMBO J. 4: 2627–33), TGACCGA, was identified at position –278 to –272. This is a regulatory protein that binds to DNA at UAS1-B of the CYC1 gene. Other consensus sequences in the UAS1-B region of the CYC1 gene were not present in the upstream region of LAG1.

Figure 4:
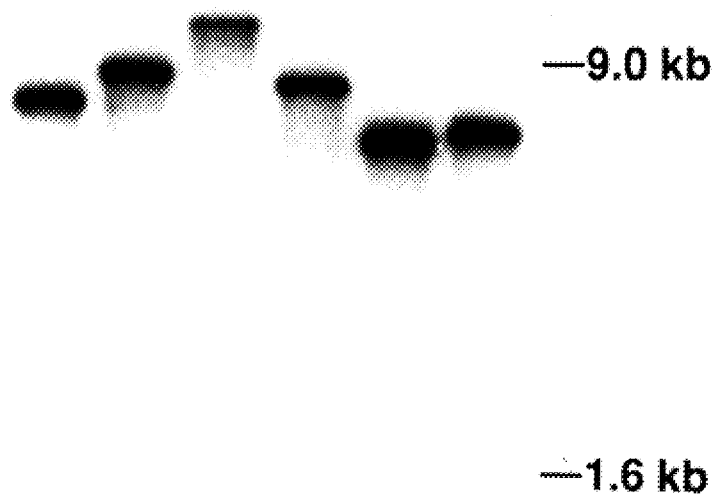
FIG. 4 depicts an autoradiogram of a Southern genomic blot of yeast DNA probed with an 868 bp ClaI-EcoRI fragment of the LAG1 gene. A 1 kb ladder (Bethesda Research Laboratories) was electrophoresed next to the digests as a size standard. Restriction enzymes used to digest genomic DNA (4 μg) were: 1, BamHI; 2, SstI; 3, XhoII; 4, SalI; 5, EcoRI; 6, SmaI.

To determine whether LAG1 is a single copy gene, yeast DNA was digested with several different restriction enzymes, and a Southern blot was prepared. The ClaI-EcoRI fragment contained within the coding region (FIG. 1) was used to probe the Southern blot (FIG. 4). None of the restriction enzymes that were selected cut within the DNA probe. In all the lanes, only a single band was detected, indicating that the gene is present in a single copy in the genome.

Although the sequence analysis did not identify any sequences similar to the gene in the databases, a Southern blot of human genomic DNA was probed with the coding region of the yeast gene. Under moderate stringency hybridization conditions, a band was identified in the Southern blot (FIG. 5). Under the same conditions, the probe also hybridized to genomic DNA obtained from galago, bovine, mouse, and salmon. These data indicate that LAG1 is present in higher eukaryotes.

EXAMPLE 3

CHROMOSOMAL LOCATION OF THE YEAST LAG1 GENE

Mapping of the Gene

The LAG1 gene was initially localized by probing a yeast chromosome blot obtained from Clontech Laboratories with the PstI-EcoRI fragment containing the LAG1 coding region. This procedure localized LAG1 to chromosome VIII. LAG1 was marked for meiotic mapping by inserting a 1.8-kb BamHI fragment containing the HIS3 gene into the BglII site located close to the 3' end of the gene (FIG. 1). This insertion was created in haploid cells. Southern analysis confirmed the chromosomal structure of this insertion. This insertion did not affect vegetative growth and division.

Figure 8:
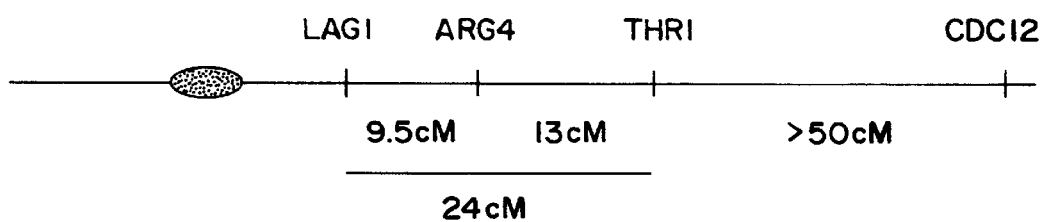
FIG. 8 provides a schematic representation of the genetic localization of the LAG1 gene. The strains XDF7-6C and XDF5-2B were used to meiotically map the LAG1 gene with reference to the genetic markers ARG4, THR1, and CDC12. For segregation of LAG1 and ARG4, the PD (parental ditype)=34, NPD (nonparental ditype)=0, and T (tetratype)=8. Segregation of LAG1 and THR1 resulted in PD=21, NPD=0, and T=19. LAG1 and CDC12 segregated to yield PD=2, NPD=10, and T=27. The segregation of ARG4 and THR1 resulted in PD=33, NPD=0, and T=12. For the segregation of ARG4 and CDC12, PD=5, NPD=6, T=24.

The LAG1 gene was meiotically mapped to the right arm of chromosome VIII using three markers: ARG4, THR1 and CDC12. The LAG1::HIS3 disruption strain XDF5-2B (MATα, ARG4, CDC12, his3, LAG1::HIS3, THR1) was mated with the congenic strain XDF7-6C (MATα, arg4, cdc12, his3, LAG1, thr1). The resulting diploids were subjected to tetrad analysis. As shown in FIG. 8, LAG1 mapped 9.5 cM from ARG4 and 24 cM from THR1. CDC12 is located greater than 50 cM from THR1 and therefore is beyond the range of linkage analysis.

EXAMPLE 4

EXPRESSION OF YEAST LAG1

LAG1 Transcript

Figures 6A, 6B:
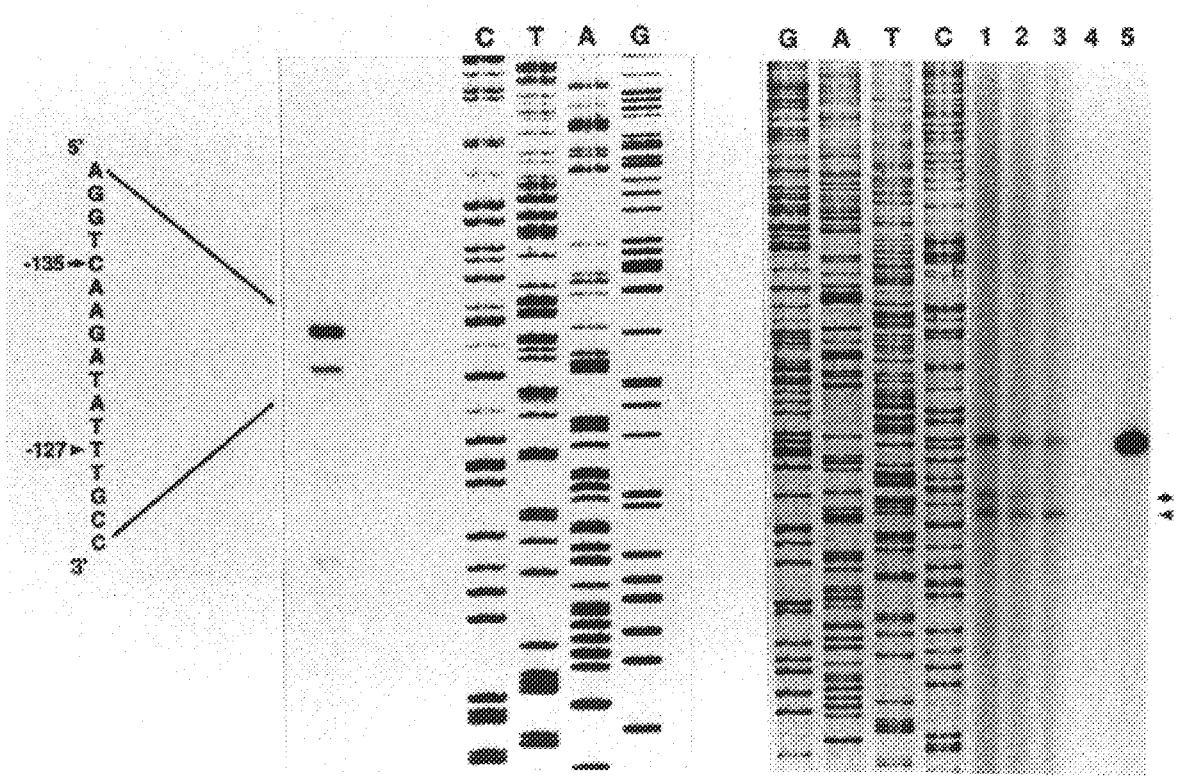
FIG. 6A provides a primer extension analysis of the 5' end of the S. cerevisiae LAG1 transcript. Lanes C,T,A, and G represent dideoxynucleotide chain-termination sequencing reactions with the primer used for the primer extension of the mRNA. A portion of the sequence of the sense strand is shown with the transcriptional start sites indicated by an arrowhead and an arrow.
FIG. 6B depicts an autoradiogram of S1 mapping of the 5' end of LAG1 S. cerevisiae mRNA. After hybridization of LAG1 probe to mRNA, varying amounts of S1 nuclease were added: lane 1, digestion with 165 units S1 nuclease; lane 2, digestion with 220 units S1 nuclease; lane 3, digestion with 330 units S1 nuclease. Lane 4 contains probe hybridized with 20 μg of tRNA followed by digestion with 330 units S1 nuclease. Lane 5 contains undigested probe. Lanes G, A, T, and C are size markers generated from dideoxynucleotide chain-termination sequencing reactions using the same primer utilized for probe generation. The arrowhead and arrow indicate the protected fragments of the probe corresponding to the transcriptional start sites observed in FIG. 6A.

The sites of transcription initiation were identified by primer extension using reverse transcriptase. Two different transcription initiation sites were identified, separated by 7 bp, as shown in FIG. 6. These results were confirmed by S1 nuclease mapping (FIG. 6). The upstream start site (–135) appeared to be utilized about 5-fold more frequently than the downstream site (–127), according to the primer extension analysis. These results were obtained using RNA from logarithmic phase cultures.

Because two different transcriptional start sites were identified, the two sites were tested for differential utilization in young and old cells. Total RNA was prepared from age-synchronized cells of different ages, and primer extension analysis was performed. No difference in the utilization of the two transcriptional start sites was observed between young and older cells up to 18 generations.

Expression During the Life Span

Figure 7:
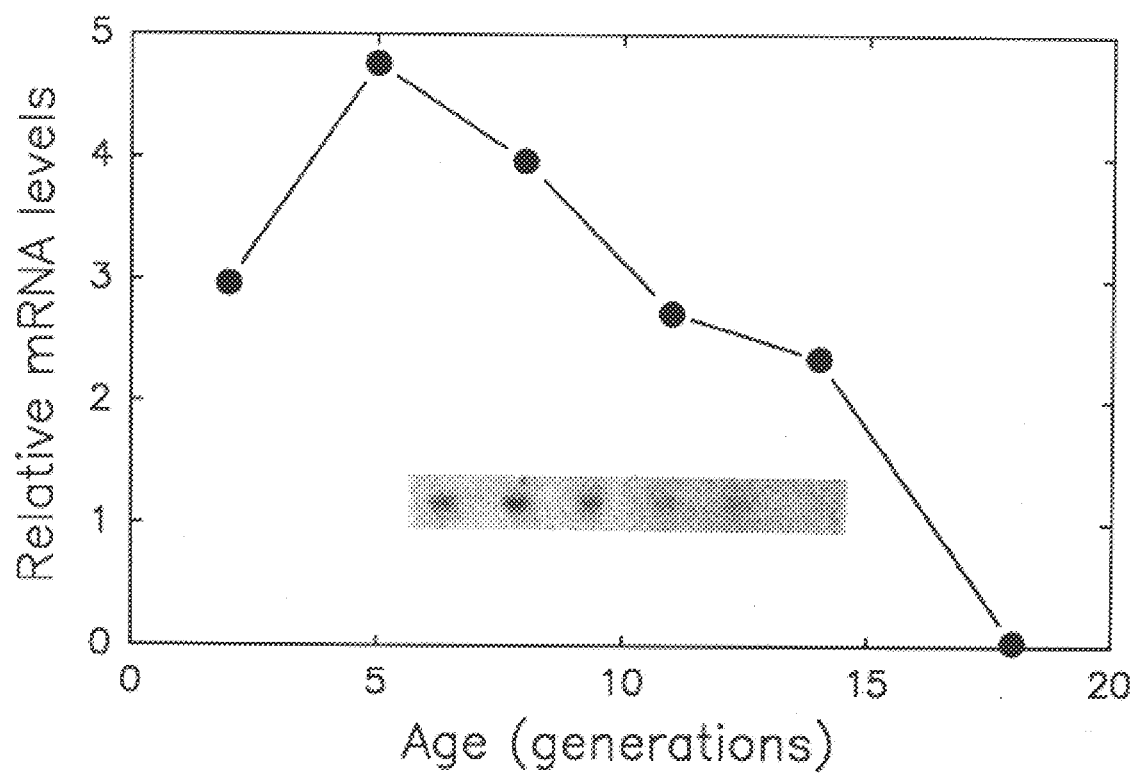
FIG. 7 depicts the LAG1 transcript levels observed in yeast of different ages by Northern analysis. Quantitation was performed by phosphorimaging. The results were normalized for the amounts of total mRNA present on each lane of the blots by probing for a transcript whose expression does not change during the life span. The inset shows an autoradiogram of the Northern blot of RNA from the cells of increasing age, left to right.

To examine LAG1 transcript levels throughout the yeast life span, age-synchronized cells of different ages were prepared. Total RNA was extracted from these cells, and a Northern analysis was performed. As shown in FIG. 7, a decrease in the transcript level was observed in older cells. Preferential expression of LAG1 in young cells was observed in each of five experiments. The majority of yeast genes do not display alterations in transcript levels as a function of replicative age (Egilmez et al., 1989 J. Biol. Chem 264:14312–17).

EXAMPLE 5

DELETION OF LAG1 CREATES A NULL MUTANT WITH INCREASED LONGEVITY

A LAG1 deletion was generated in a haploid strain by replacing 80% of the open reading frame with a DNA fragment carrying a TRP1 selectable marker. The deletion in the gene was confirmed by Southern analysis and this mutation completely abolished expression of LAG1 as determined on Northern blots. The deletion had no effect on the appearance, size, shape, budding pattern, viability, or the vegetative growth and division (culture growth kinetics) of the cells.

To examine the role of the gene in the aging process, a life span determination was performed on cells harboring the LAG1 deletion. Compared to the wild-type, the cells with the gene deletion exhibited a 47% increase in the mean life span (FIG. 9). The mean life span increased from about 17 to about 25 cell divisions. A concomitant increase (48%) was observed in the maximum life span. The maximum life span of the cells with the intact gene was 25, while the maximum life span of cells with the gene deletion was 37 cell divisions. Similar results were obtained in five experiments with three independently-derived LAG1-deletion clones.

The life span extension was not due to the TRP1 marker: life span determinations were performed on rich medium (YPD), eliminating the metabolic requirement for TRP1. Moreover, longevity was unaffected when the TRP1 gene was integrated into the parental strain bearing an intact LAG1 gene.

The null mutant created by deletion of LAG1 was complemented by expression of LAG1 from a plasmid transformed into the strain. These data demonstrate that the phenotype of yeast cells with the LAG1 deletion was due solely to the recessive mutation in LAG1.

EXAMPLE 6

A 5' DELETION IN THE LAG1 CODING REGION INCREASES LONGEVITY

A deletion of 5' half of the LAG1 coding region in haploid cells was made to map the functional domains of LAG1.
Methods The strategy for deletion of the 5' end of the gene was to clone in inverse orientation regions flanking the segment of the gene that was to be deleted, in two successive steps. These regions were cloned in the multiple cloning site of an integrative plasmid. Initially, a 525 bp ApaI-ClaI fragment (FIG. 10) was ligated into the multiple cloning site of the integrative plasmid pRS404 (which possesses the TRP1 selectable marker) (Sikorski et al. 1989 Genetics 122:19–27). In the second step, DNA from selected clones was digested with SmaI, which is present in the multiple cloning site, to create a blunt-ended fragment. The ends of the 1,339-bp SstI-PstI fragment encompassing the upstream region of the LAG1 gene were made blunt with T4 DNA polymerase and ligated into the SmaI site. A clone with the appropriate orientation of the inserted fragment was selected. The plasmid DNA from this clone was then digested with the enzymes NcoI and EcoRI to create a linear DNA fragment. This resulted in a fragment containing the integrative plasmid vector, pRS404 (4,271 bp), flanked by 341 bp of the 3' end of the coding region of the gene (ApaI to EcoRI) and 960 bp of the upstream region of the LAG1 gene (NcoI to PstI). This linear fragment was isolated and used to transform YPHDF-1A yeast cells. The cells were then plated on SC medium lacking tryptophan to select for cells with the integrated DNA fragment.

Thus, 158 bp of upstream region including the transcription start site at −135 and 563 bp from the 5' end of the coding region were deleted. The resulting strain was designated YPHDF-1A LAG1Δ::TRP1.
Results The LAG1 5' deletion was verified by Southern blot analysis. Northern blot analysis indicated that two LAG1 transcripts were expressed from the truncated gene. A 1.4 kb transcript initiated well within the pBR322 DNA replacing the LAG1 5' sequences, while a 0.9 kb transcript initiated close to the junction between the pBR322 and LAG1 sequences. In either case, the transcript would allow the production of the same truncated LAG1 protein, missing close to one-half of its sequences from the N-terminus.

As depicted in FIG. 11, the 5' deletion mutant had a 50% increase in its mean and maximum life span. Moreover, the 5' deletion of LAG1 had no effect on cell growth and viability.

Complementation of the mutation by an additional wild-type LAG1 gene did not restore the wild-type life span in a haploid strain. Thus, a 5' deletion of one-half of the LAG1 coding region creates a dominant mutation.

These data suggest that a life span limitation function resides in the 5' end of LAG1, whereas the life-span extending activity of the protein may reside in the 3' end of LAG1. Hence, removal of the 5' end leads to increased longevity but removal of the 3' end may remove a needed longevity function, thereby diminishing longevity.

Moreover, deletion of the 5' end of LAG1 postpones senescence. As yeast cells progress through their replicative life span, their generation time, as measured by the interval between buddings, increases. (Egilmez et al. 1989 *J. Bacteriol.* 171:37–42). At first this increase in generation time is gradual but later the generation time increases precipitously and constitutes the most accurate marker of the cell's physiological age.

However, as depicted in FIG. 14, yeast cells bearing LAG1 with the 5' deletion had a marked delay in increased generational time compared to control cells. Therefore, the increase in longevity resulting from manipulation of LAG1 is coupled to postponement of senescence. Yeast cells with the 5' LAG1 mutation live longer and also function longer as young cells.

EXAMPLE 7

OVEREXPRESSION OF LAG1 INCREASES CELLULAR LONGEVITY

Methods

The DNA fragment encompassing the entire LAG1 gene was obtained as a 2-kb BamHI fragment. This was achieved by removing the 3' overhang from PstI-cut LAG1 DNA to create blunt ends (FIG. 10) and ligating phosphorylated BamHI linkers (BRL) to this blunt-ended fragment. The ligation mixture was then digested with BamHI. A 2-kb BamHI fragment was isolated and inserted into the BamHI site of pBM150 (Johnston et al. 1984 *Mol. Cell. Biol.* 4: 1440–48), downstream of the GAL1 promoter (FIG. 10) to generate the plasmid pPB5. Clones were screened for inserts having the desired orientation. Plasmid DNA was purified and used to transform yeast strains. This construct expressed LAG1 at very high levels.

A binary expression system consisting of two plasmids (FIG. 10) was used to provide intermediate levels of LAG1 expression. One plasmid encoded the glucocorticoid receptor (G-N795) while the other contained glucocorticoid response elements fused upstream of the CYC1 basal promoter (2UG). The LAG1 coding region was excised as a 2-kb BamHI fragment from the plasmid pPB5 and ligated into the unique BamHI site located downstream of the CYC1 promoter. Clones were selected which had LAG1 in the correct orientation. The two plasmids, 2UG containing LAG1, and G-N795, were transformed into yeast cells. Transformants were selected on SC medium lacking tryptophan and uracil. Control yeast cells were prepared by transformation with G-N795 and 2UG having no LAG1 insert.

Results

The life span of yeast cells transformed with the pPB5 plasmid construct was determined either in the presence of galactose to induce LAG1 expression or in the presence of glucose to repress it. As shown in FIG. 12, an increase in mortality was observed early in the life span of cells overexpressing LAG1. However, cells that escaped this deleterious effect lived significantly longer than the cells in which the gene was not overexpressed. There was no difference in the life span of the yeast strain transformed with pBM150 lacking the LAG1 gene, whether it was determined on glucose or galactose.

Analysis of mRNA levels on Northern blots showed that induction by galactose resulted in a very substantial increase in LAG1 expression from the GAL1 promoter. Thus overexpression from the GAL1 promoter results in very high levels of expression.

To provide lower levels of expression, an alternate regulatable promoter was utilized consisting of the two plasmid expression system depicted in FIG. 10. One plasmid (G-N795) encodes the glucocorticoid receptor under the control of a constitutive yeast promoter. The other (2UG) possesses glucocorticoid response elements fused upstream of the CYC1 basal promoter to provide regulated expression of any gene inserted downstream, in this case LAG1. Addition of different amounts of hormone to the growth medium induces different levels of expression.

After transformation of these two plasmids into yeast cells, transformants containing both plasmids were selected. A Northern blot analysis was performed to confirm the levels of induction of the gene on addition of the glucocorticoid hormone. The level of expression was dependent on the concentration of the hormone in the growth medium.

The life spans of individual cells expressing LAG1 from the 2UG construct were determined. As a control, the life spans of transformants containing the two plasmids, G-N795 and 2UG, but without the LAG1 insert, were determined. As shown in FIG. 13A, a 60% extension was observed in the mean and maximum life span of cells in which the LAG1 gene was overexpressed. However, there was a decrease in the mean and maximum life span of the control cells to which the glucocorticoid hormone was added, as compared to control cells to which it was not, suggesting that the addition of the glucocorticoid hormone had a deleterious effect on the cells. This effect was dependent on the presence of the glucocorticoid receptor (data not shown). It was not clear from this study whether expression of LAG1 simply countered this deleterious effect or whether it had an intrinsic effect on yeast longevity.

To alleviate the deleterious effect of the hormone, LAG1 was induced in cells that had completed 12 generations. This was preformed by moving the cells during the life span determination to a second agar slab containing the glucocorticoid hormone. As shown in FIG. 13B, an increase in the life span of cells in which the gene was overexpressed was observed, and the deleterious effect of the hormone had been largely eliminated. Similar results were obtained when overexpression of LAG1 was induced at 10 generations of age. A delay in glucocorticoid treatment to 15 generations completely abolished the deleterious effect of the hormone. Moreover, no significant difference was observed when hormone addition was at 5 generations as compared to its presence throughout the life span. Therefore, these data suggest that overexpression of the gene early in the life span when endogenous LAG1 mRNA levels are high is detrimental to the cell. However, overexpression of LAG1 later in life, when the endogenous mRNA levels are low, can extend longevity.

EXAMPLE 8

LAG1 AND TOLERANCE TO STRESS

Methods

The phenotypic characteristics of cells which overexpressed full length LAG1 and of cells with 5' LAG1 mutations were compared to parental cells as described in Example 1.

Results

Culture growth kinetics, cell size, cell shape and budding pattern remained unaffected by the LAG1 mutation. No differences were observed in sporulation or mating ability. Sensitivity to physical parameters such as heat, cold and heat shock did not differ between mutants and wild type. Mutants also did not exhibit any difference in caffeine resistance. Mutant sensitivity to nitrogen starvation, pH, osmotic changes and salt did not differ significantly from wild type.

Wild type yeast display a pronounced attenuation of life span when the pH is lowered from 6.5–7.0 to about 5.3–5.5. However, overexpression of LAG1, as described in Example 7, dramatically improved survival (see FIG. 16).

EXAMPLE 9

IN VITRO TRANSLATION OF LAG1 POLYPEPTIDE

Subcloning

A 2.0 kb fragment of LAG1 containing BamHI ends was used for subcloning. The fragment contains the entire open reading frame of LAG1, about 150 bp upstream and about 760 bp downstream of the coding sequence. The 2.0 kb LAG1 fragment was subcloned into the BamHI site of the pSP64 vector from Promega (see Melton et al. 1984 *Nucl. Acids Res.* 12: 7035–56). The pSP64/LAG1 plasmid, approximately 5 kb in size, was then linearized with the restriction enzyme AvaI and separated by agarose gel electrophoresis to ensure complete digestion. The 5 kb band was excised from the gel and the DNA purified by Geneclean II (Wilson, 1988 *Bio Techniques* 6: 733; Vogelstein et al. 1979 *Proc. Natl. Acad. Sci.* 76: 615).

In Vitro Transcription

An in vitro transcription system was then used to synthesize LAG1 mRNA. The following components were added to the reaction at room temperature in the order listed: transcription buffer, 10 mM DTT, 50 units RNasin (RNase inhibitor), 0.5 mM ATP, 0.5 mM CTP, 0.5 mM UTP, 0.025 mM GTP, 0.5 mM cap analog [m$^7$G(5')ppp(5')G], 1 µg linearized LAG1 DNA template, 40 units SP6 RNA polymerase, and nuclease-free water to bring up the volume to 50 µl. The reaction was incubated for 90 minutes at 37° C. A portion of the reaction was separated by agarose gel electrophoresis. The in vitro transcription product was visualized as the expected 2.0 kb LAG1 message. The LAG1

DNA template was removed by adding 1 unit of RNase-free DNase to the reaction. This reaction mixture was incubated for a further 30 minutes at 37° C. The reaction was phenol/chloroform extracted and ethanol precipitated to remove unincorporated nucleotides. The RNA was pelleted by centrifugation and resuspended in nuclease-free water to a concentration of 1 mg/ml.

In Vitro Translation

The LAG1 RNA template was heated to 67° C. for 10 minutes and immediately cooled on ice to increase the efficiency of translation. A rabbit reticulocyte lysate in vitro translation system was then used to synthesize the LAG1 protein (Pelham et al. 1976 *Eur. J. Biochem.* 67: 247 and Promega Corporation, 1992, *Rabbit Reticulocyte Lysate System Technical Manual*). The following components were added on ice in the order listed: rabbit reticulocyte lysate, 40 units RNasin, 0.02 mM amino acid mixture minus methionine, 1 or 2 µg LAG1 RNA substrate, 10 mCi/ml$^{35}$S-Methionine, nuclease-free water to bring the reaction up to 50 µl. The in vitro translation reaction was incubated at 30° C. for 60 minutes. 10 µl of each reaction was added to 10 µl of sample buffer and boiled for 5 minutes. The samples were then separated by electrophoresis on a 10% SDS-polyacrylamide gel. The gel was dried by vacuum and direct autoradiography of the gel was used to detect the labeled LAG1 protein (FIG. 17). In lanes 1 and 2, 1 µg of LAG1 RNA was added to the reaction. In lanes 3 and 4, 2 µg of LAG1 RNA was added to the reaction. Lanes 2 and 4 had 1 µg of 1M potassium acetate added to bring the final potassium acetate concentration up to 99 mM. Lanes 1 and 3 had no potassium acetate added, thus the final potassium acetate concentration was 79 mM which was already present in the reticulocyte lysate, during translations. Lane 5 was a control in which no exogenous RNA was added. The arrow points to the LAG1 polypeptide.

EXAMPLE 10

THE HUMAN LAG1 IS EXPRESSED AS AN APPROXIMATE 7 KB mRNA

A Southern blot of human genomic DNA was probed with the coding region of the *S. cerevisiae* LAG1. Under moderate stringency hybridization conditions, a band was identified in the Southern blot (FIG. 5). Under the same conditions, the probe also hybridized to genomic DNA obtained from galago, bovine, mouse, and salmon.

A Northern blot of human mRNA was prepared using poly(A)$^+$ RNA isolated from heart, brain, placenta, lung, liver, skeletal muscle, kidney and pancreatic tissues. This blot was probed with the coding region of the *S. cerevisiae* LAG1 under moderate stringency hybridization conditions.

As illustrated by FIG. 15, an approximate 7.0 kb human mRNA was detected in all human tissues tested. However, this mRNA was most prominently expressed in placenta, lung, liver and especially skeletal muscle tissues.

What is claimed is:

1. An isolated nucleic acid encoding a Longevity Assurance Gene 1 (LAG1) polypeptide comprising the amino acid sequence of SEQ ID NO:2.

2. An isolated Longevity Assurance Gene (LAG1) nucleic acid comprising SEQ ID NO:1.

3. An isolated Longevity Assurance Gene (LAG1) nucleic acid comprising SEQ ID NO:3.

4. An isolated Longevity Assurance Gene (LAG1) nucleic acid comprising SEQ ID NO:5.

5. An isolated nucleic acid insert in pDF5 comprising ATCC No. 75790.

6. An isolated nucleic acid encoding a Longevity Assurance Gene 1 (LAG1) cDNA or S. cerevisiae (LAG1) genomic DNA.

7. The isolated nucleic acid of any one of claims 2 to 5 wherein said nucleic acid is RNA.

8. An isolated replication vector comprising any one of the nucleic acids of any one of claims 1 to 5.

9. An isolated expression vector comprising anyone of the nucleic acids of any one of claims 1 to 5 operably linked to nucleotide sequence for effecting expression of a polypeptide encoded by said nucleic acid.

10. The isolated expression vector of claim 8 which replicates in a bacterial, yeast, insect or mammalian host cell.

11. An isolated host cell comprising the replication vector of claim 8.

12. The host cell of claim 11 wherein said cell is a yeast, bacterial, mammalian or insect cell.

13. An isolated host cell comprising the expression vector of claim 9.

14. The host cell of claim 13 wherein said cell is a yeast, bacterial, mammalian or insect cell.

15. A method for preparing a human LAG1 polypeptide which comprises:

(a) isolating a human DNA encoding the human LAG1 polypeptide by contacting a cDNA library of human DNA with a LAG1 probe for a time and under moderately stringent hybridization conditions, identifying a hybridization complex of said probe bound to said human LAG1 DNA, and isolating the human LAG1 DNA;

(b) ligating said human LAG1 DNA into an expression vector comprising a nucleotide sequence for effecting expression of the LAG1 polypeptide encoded by said LAG1 DNA to generate a LAG1 expression vector;

(c) transforming a host cell with said LAG1 expression vector;

(d) culturing said host cell under conditions sufficient to express said LAG1 polypeptide; and (e) isolating said human LAG1 polypeptide;

wherein said LAG1 probe comprises at least about 14 contiguous nucleotides of SEQ ID NO:1 to specifically hybridize to the nucleic acid according to claim 1.

16. The method of claim 15 wherein said human LAG1 DNA is cDNA or genomic.

17. A method for preparing a human LAG1 polypeptide which comprises:

(a) isolating nucleic acid copies of a human LAG1 DNA or RNA which encodes the LAG1 polypeptide by contacting a sample containing said human LAG1 DNA or RNA with at least one oligonucleotide for a time and under conditions sufficient to select nucleic acid copies of said human LAG1 DNA or RNA, identifying said copies, and isolating said copies;

(b) ligating said nucleic acid copies into an expression vector comprising a nucleotide sequence for effecting expression of the human LAG1 polypeptide encoded by said nucleic acid copies;

(c) expressing said human LAG1 polypeptide; and (d) isolating said human LAG1 polypeptide;

wherein said oligonucleotide comprises at least about 14 contiguous nucleotides of SEQ ID NO:1 to specifically hybridize the nucleic acid according to claim 1.

18. A method of isolating a Longevity Assurance Gene 1 (LAG1) nucleic acid having a polypeptide sequence comprising the amino acid sequence of SEQ ID NO:2 by in vitro nucleic acid amplification which comprises:

(a) contacting a sample containing said LAG1 nucleic acid with at least one oligonucleotide for a time and under conditions sufficient to produce RNA or DNA copies of said LAG1 nucleic acid;

(b) identifying said copies; and (c) isolating said copies;

wherein said oligonucleotide comprises at least 14 contiguous nucleotides of SEQ ID NO:1 to specifically hybridize the nucleic acid according to claim 1.

19. An isolated LAG1 nucleic acid consisting of SEQ ID NO:1.

20. An isolated LAG1 nucleic acid consisting of SEQ ID NO:3.

21. An isolated LAG1 nucleic acid consisting of SEQ ID NO:5.

\* \* \* \* \*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2134 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 656..1891

( x i ) SEQUENCE DESCRIPTION: SEQ ID NO:1:

```
CATTGCGTTT   CATTTATGTA   ATTCGAATTT   CTTAACTAAT   CACTAATAAC   GGTAAATGAG        60

GTTAACCATT   AGAATAATGT   ATATAATTAC   GTACAAAGGC   TACCGAAGTT   CTGCGGCAGT       120

AATGTAGGGT   TTAGCTTTTG   AATCAATCTT   AGAGCCTGCT   ATCTTCCTGC   ACTTGCTGAT       180

TCCATAAATA   TAAACACCTT   TCGGCTAGAC   CGACAAAGGT   CGTAGTCGTT   TTTCCTTTAG       240

GGTATTATGA   CCAGGGACAC   CCCAGTCCGT   CAAGACTAAT   ATCGATAGTA   TATTACAGGT       300

AAATAGAGAT   CCCTTTTATA   GAGAATTTAA   CGCTTTAAAC   TTACCTAATG   CGTCATCTTC       360

CATTTGAAAT   CCTTCTTGAC   CGAGGGCAGC   CCAGGGGTAG   TGAAAAACGA   TGAAAAAATT       420

CCATTTTTTT   AGCGGGAAAA   GCAAATTGCA   GCATCAACAT   TTTACGCGCT   ATCACTTGAC       480

AAACAAGGCA   AGGAAAACTG   CAGCCCTGTA   CTAAGAAGGT   CAAGATATTT   GCCAAACGAT       540

TTCGTAAGGT   TGTCTCAATT   GATCTGACTG   CTTGTCTATC   TAAAGTGGCA   AGGTATATTA       600
```

-continued

| | | | | | | | | | | | |
|---|---|---|---|---|---|---|---|---|---|---|---|
| GACAGTGTTG | AGAGTGAACT | CCAAGATACA | GAGAAACTGA | AGAAATAACG | ACAAC | ATG<br>Met<br>1 | | | | | 658 |

| | | | | | | | | | | | | | | | |
|---|---|---|---|---|---|---|---|---|---|---|---|---|---|---|---|
| ACA<br>Thr | TCA<br>Ser | GCT<br>Ala | ACG<br>Thr<br>5 | GAC<br>Asp | AAA<br>Lys | TCT<br>Ser | ATC<br>Ile | GAT<br>Asp<br>10 | AGG<br>Arg | TTA<br>Leu | GTT<br>Val | GTT<br>Val | AAT<br>Asn<br>15 | GCA<br>Ala | AAA<br>Lys | 706 |
| ACA<br>Thr | AGA<br>Arg | AGA<br>Arg<br>20 | CGA<br>Arg | AAC<br>Asn | TCT<br>Ser | TCC<br>Ser | GTG<br>Val<br>25 | GGT<br>Gly | AAA<br>Lys | ATT<br>Ile | GAT<br>Asp | TTA<br>Leu<br>30 | GGT<br>Gly | GAT<br>Asp | ACA<br>Thr | 754 |
| GTT<br>Val | CCT<br>Pro<br>35 | GGC<br>Gly | TTT<br>Phe | GCA<br>Ala | GCC<br>Ala | ATG<br>Met<br>40 | CCT<br>Pro | GAA<br>Glu | AGT<br>Ser | GCT<br>Ala | GCC<br>Ala<br>45 | TCT<br>Ser | AAA<br>Lys | AAT<br>Asn | GAG<br>Glu | 802 |
| GCC<br>Ala<br>50 | AAA<br>Lys | AAA<br>Lys | AGG<br>Arg | ATG<br>Met | AAA<br>Lys<br>55 | GCC<br>Ala | TTG<br>Leu | ACT<br>Thr | GGT<br>Gly | GAC<br>Asp<br>60 | TCT<br>Ser | AAA<br>Lys | AAG<br>Lys | GAT<br>Asp | AGT<br>Ser<br>65 | 850 |
| GAC<br>Asp | CTA<br>Leu | CTG<br>Leu | TGG<br>Trp | AAG<br>Lys<br>70 | GTT<br>Val | TGG<br>Trp | TTT<br>Phe | TCA<br>Ser | TAT<br>Tyr<br>75 | AGA<br>Arg | GAA<br>Glu | ATG<br>Met | AAT<br>Asn | TAC<br>Tyr<br>80 | CGT<br>Arg | 898 |
| CAT<br>His | AGT<br>Ser | TGG<br>Trp | TTG<br>Leu<br>85 | ACA<br>Thr | CCA<br>Pro | TTC<br>Phe | TTC<br>Phe | ATA<br>Ile<br>90 | CTT<br>Leu | GTA<br>Val | TGC<br>Cys | GTG<br>Val | TAT<br>Tyr<br>95 | AGC<br>Ser | GCG<br>Ala | 946 |
| TAC<br>Tyr | TTT<br>Phe | TTA<br>Leu<br>100 | TCT<br>Ser | GGG<br>Gly | AAT<br>Asn | AGA<br>Arg | ACA<br>Thr<br>105 | GAA<br>Glu | TCA<br>Ser | AAC<br>Asn | CCG<br>Pro | CTG<br>Leu<br>110 | CAC<br>His | ATG<br>Met | TTC<br>Phe | 994 |
| GTA<br>Val | GCC<br>Ala<br>115 | ATA<br>Ile | TCA<br>Ser | TAT<br>Tyr | CAA<br>Gln<br>120 | GTT<br>Val | GAT<br>Asp | GGC<br>Gly | ACA<br>Thr | GAC<br>Asp<br>125 | TCA<br>Ser | TAT<br>Tyr | GCA<br>Ala | AAA<br>Lys | GGT<br>Gly | 1042 |
| ATC<br>Ile<br>130 | AAA<br>Lys | GAT<br>Asp | TTG<br>Leu | AGT<br>Ser | TTT<br>Phe<br>135 | GTG<br>Val | TTT<br>Phe | TTC<br>Phe | TAC<br>Tyr | ATG<br>Met<br>140 | ATT<br>Ile | TTC<br>Phe | TTC<br>Phe | ACA<br>Thr | TTT<br>Phe<br>145 | 1090 |
| TTA<br>Leu | CGT<br>Arg | GAG<br>Glu | TTT<br>Phe | TTG<br>Leu<br>150 | ATG<br>Met | GAT<br>Asp | GTT<br>Val | GTA<br>Val | ATT<br>Ile<br>155 | CGA<br>Arg | CCA<br>Pro | TTC<br>Phe | ACG<br>Thr | GTA<br>Val<br>160 | TAC<br>Tyr | 1138 |
| CTA<br>Leu | AAT<br>Asn | GTT<br>Val | ACT<br>Thr<br>165 | TCC<br>Ser | GAG<br>Glu | CAT<br>His | CGT<br>Arg | CAA<br>Gln<br>170 | AAG<br>Lys | CGT<br>Arg | ATG<br>Met | CTA<br>Leu | GAA<br>Glu<br>175 | CAA<br>Gln | ATG<br>Met | 1186 |
| TAT<br>Tyr | GCC<br>Ala | ATA<br>Ile<br>180 | TTT<br>Phe | TAT<br>Tyr | TGC<br>Cys | GGA<br>Gly | GTT<br>Val<br>185 | TCA<br>Ser | GGG<br>Gly | CCC<br>Pro | TTT<br>Phe | GGT<br>Gly<br>190 | CTT<br>Leu | TAT<br>Tyr | ATT<br>Ile | 1234 |
| ATG<br>Met | TAC<br>Tyr<br>195 | CAT<br>His | AGT<br>Ser | GAT<br>Asp | TTG<br>Leu<br>200 | TGG<br>Trp | TTG<br>Leu | TTC<br>Phe | AAG<br>Lys | ACA<br>Thr<br>205 | AAA<br>Lys | CCA<br>Pro | ATG<br>Met | TAC<br>Tyr | AGA<br>Arg | 1282 |
| ACA<br>Thr<br>210 | TAT<br>Tyr | CCT<br>Pro | GTT<br>Val | ATA<br>Ile | ACC<br>Thr<br>215 | AAT<br>Asn | CCG<br>Pro | TTC<br>Phe | TTG<br>Leu | TTT<br>Phe<br>220 | AAG<br>Lys | ATA<br>Ile | TTT<br>Phe | TAC<br>Tyr | TTG<br>Leu<br>225 | 1330 |
| GGT<br>Gly | CAA<br>Gln | GCG<br>Ala | GCA<br>Ala | TTT<br>Phe<br>230 | TGG<br>Trp | GCG<br>Ala | CAA<br>Gln | CAG<br>Gln | GCT<br>Ala<br>235 | TGT<br>Cys | GTT<br>Val | CTT<br>Leu | GTT<br>Val | CTA<br>Leu<br>240 | CAA<br>Gln | 1378 |
| TTA<br>Leu | GAA<br>Glu | AAG<br>Lys | CCA<br>Pro<br>245 | AGA<br>Arg | AAG<br>Lys | GAT<br>Asp | TAC<br>Tyr | AAG<br>Lys<br>250 | GAA<br>Glu | TTG<br>Leu | GTT<br>Val | TTT<br>Phe | CAT<br>His<br>255 | CAC<br>His | ATT<br>Ile | 1426 |
| GTG<br>Val | ACA<br>Thr | TTA<br>Leu<br>260 | TTA<br>Leu | TTA<br>Leu | ATT<br>Ile | TGG<br>Trp | TCA<br>Ser<br>265 | TCA<br>Ser | TAT<br>Tyr | GTT<br>Val | TTC<br>Phe | CAT<br>His<br>270 | TTT<br>Phe | ACC<br>Thr | AAA<br>Lys | 1474 |
| ATG<br>Met | GGA<br>Gly<br>275 | TTG<br>Leu | GCT<br>Ala | ATC<br>Ile | TAT<br>Tyr<br>280 | ATT<br>Ile | ACT<br>Thr | ATG<br>Met | GAT<br>Asp | GTG<br>Val<br>285 | TCA<br>Ser | GAT<br>Asp | TTT<br>Phe | TTC<br>Phe | CTT<br>Leu | 1522 |
| TCT<br>Ser<br>290 | TTG<br>Leu | TCT<br>Ser | AAG<br>Lys | ACA<br>Thr | TTA<br>Leu<br>295 | AAC<br>Asn | TAT<br>Tyr | CTG<br>Leu | AAT<br>Asn | TCT<br>Ser<br>300 | GTA<br>Val | TTT<br>Phe | ACT<br>Thr | CCC<br>Pro | TTT<br>Phe<br>305 | 1570 |

```
GTG  TTC  GGC  TTG  TTC  GTG  TTC  TTT  TGG  ATC  TAT  CTG  CGC  CAT  GTC  GTG    1618
Val  Phe  Gly  Leu  Phe  Val  Phe  Phe  Trp  Ile  Tyr  Leu  Arg  His  Val  Val
               310                      315                      320

AAT  ATC  AGA  ATA  TTA  TGG  TCA  GTC  TTA  ACA  GAA  TTC  CGT  CAT  GAA  GGT    1666
Asn  Ile  Arg  Ile  Leu  Trp  Ser  Val  Leu  Thr  Glu  Phe  Arg  His  Glu  Gly
               325                      330                      335

AAT  TAT  GTG  TTG  AAT  TTT  GCC  ACA  CAA  CAA  TAC  AAA  TGT  TGG  ATT  TCG    1714
Asn  Tyr  Val  Leu  Asn  Phe  Ala  Thr  Gln  Gln  Tyr  Lys  Cys  Trp  Ile  Ser
               340                      345                      350

TTG  CCA  ATT  GTA  TTT  GTA  CTA  ATT  GCT  GCG  TTA  CAA  TTA  GTT  AAC  CTG    1762
Leu  Pro  Ile  Val  Phe  Val  Leu  Ile  Ala  Ala  Leu  Gln  Leu  Val  Asn  Leu
               355                      360                      365

TAT  TGG  CTG  TTT  TTA  ATT  CTT  AGA  ATC  TTG  TAC  AGA  TTG  ATA  TGG  CAA    1810
Tyr  Trp  Leu  Phe  Leu  Ile  Leu  Arg  Ile  Leu  Tyr  Arg  Leu  Ile  Trp  Gln
370                      375                      380                      385

GGT  ATC  CAA  AAG  GAC  GAA  AGA  AGT  GAC  AGT  GAT  TCT  GAT  GAG  AGC  GCT    1858
Gly  Ile  Gln  Lys  Asp  Glu  Arg  Ser  Asp  Ser  Asp  Ser  Asp  Glu  Ser  Ala
               390                      395                      400

GAA  AAT  GAA  GAA  TCT  AAG  GAA  AAG  TGT  GAA       TAAACGTATC  TTAAGGAGAA    1908
Glu  Asn  Glu  Glu  Ser  Lys  Glu  Lys  Cys  Glu
               405                      410

TACGTATCAT  CATATGATTT  CCCCCCTGTA  TGAAGGCCAA  GTTAACATGG  TATAGCTCAT            1968

AGTTGTTGTT  ATAAGAAGCA  TAAACCCAAG  TACGAAAGTA  ATAATTCTGT  AAAAAAAAAA            2028

AAAATGCGTT  TATTTAGCGT  CTTCGGGTTG  GCTATATATA  TATATTTAAG  GATATATGGG            2088

CATATGTACA  AGTTTAGGTT  AACAAGCCAA  AAGAAAATAA  AAGTGT                            2134
```

( 2 ) INFORMATION FOR SEQ ID NO:2:

( i ) SEQUENCE CHARACTERISTICS:
        ( A ) LENGTH: 411 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Ser  Ala  Thr  Asp  Lys  Ser  Ile  Asp  Arg  Leu  Val  Val  Asn  Ala
 1                   5                    10                       15

Lys  Thr  Arg  Arg  Arg  Asn  Ser  Ser  Val  Gly  Lys  Ile  Asp  Leu  Gly  Asp
               20                        25                       30

Thr  Val  Pro  Gly  Phe  Ala  Ala  Met  Pro  Glu  Ser  Ala  Ala  Ser  Lys  Asn
               35                        40                       45

Glu  Ala  Lys  Lys  Arg  Met  Lys  Ala  Leu  Thr  Gly  Asp  Ser  Lys  Lys  Asp
          50                   55                       60

Ser  Asp  Leu  Leu  Trp  Lys  Val  Trp  Phe  Ser  Tyr  Arg  Glu  Met  Asn  Tyr
 65                      70                       75                       80

Arg  His  Ser  Trp  Leu  Thr  Pro  Phe  Phe  Ile  Leu  Val  Cys  Val  Tyr  Ser
                    85                       90                       95

Ala  Tyr  Phe  Leu  Ser  Gly  Asn  Arg  Thr  Glu  Ser  Asn  Pro  Leu  His  Met
                    100                      105                      110

Phe  Val  Ala  Ile  Ser  Tyr  Gln  Val  Asp  Gly  Thr  Asp  Ser  Tyr  Ala  Lys
               115                       120                      125

Gly  Ile  Lys  Asp  Leu  Ser  Phe  Val  Phe  Phe  Tyr  Met  Ile  Phe  Phe  Thr
          130                      135                       140

Phe  Leu  Arg  Glu  Phe  Leu  Met  Asp  Val  Val  Ile  Arg  Pro  Phe  Thr  Val
145                      150                      155                      160

Tyr  Leu  Asn  Val  Thr  Ser  Glu  His  Arg  Gln  Lys  Arg  Met  Leu  Glu  Gln
                    165                      170                      175
```

|   |   |   |   |   |   |   |   |   |   |   |   |   |   |   |
|---|---|---|---|---|---|---|---|---|---|---|---|---|---|---|
| Met | Tyr | Ala | Ile | Phe | Tyr | Cys | Gly | Val | Ser | Gly | Pro | Phe | Gly | Leu | Tyr |
|  |  |  | 180 |  |  |  |  | 185 |  |  |  |  | 190 |  |  |
| Ile | Met | Tyr | His | Ser | Asp | Leu | Trp | Leu | Phe | Lys | Thr | Lys | Pro | Met | Tyr |
|  |  | 195 |  |  |  |  | 200 |  |  |  |  | 205 |  |  |  |
| Arg | Thr | Tyr | Pro | Val | Ile | Thr | Asn | Pro | Phe | Leu | Phe | Lys | Ile | Phe | Tyr |
|  | 210 |  |  |  |  | 215 |  |  |  |  | 220 |  |  |  |  |
| Leu | Gly | Gln | Ala | Ala | Phe | Trp | Ala | Gln | Gln | Ala | Cys | Val | Leu | Val | Leu |
| 225 |  |  |  |  | 230 |  |  |  |  | 235 |  |  |  |  | 240 |
| Gln | Leu | Glu | Lys | Pro | Arg | Lys | Asp | Tyr | Lys | Glu | Leu | Val | Phe | His | His |
|  |  |  |  | 245 |  |  |  |  | 250 |  |  |  |  | 255 |  |
| Ile | Val | Thr | Leu | Leu | Leu | Ile | Trp | Ser | Ser | Tyr | Val | Phe | His | Phe | Thr |
|  |  |  | 260 |  |  |  |  | 265 |  |  |  |  | 270 |  |  |
| Lys | Met | Gly | Leu | Ala | Ile | Tyr | Ile | Thr | Met | Asp | Val | Ser | Asp | Phe | Phe |
|  |  | 275 |  |  |  |  | 280 |  |  |  |  | 285 |  |  |  |
| Leu | Ser | Leu | Ser | Lys | Thr | Leu | Asn | Tyr | Leu | Asn | Ser | Val | Phe | Thr | Pro |
|  | 290 |  |  |  |  | 295 |  |  |  |  | 300 |  |  |  |  |
| Phe | Val | Phe | Gly | Leu | Phe | Val | Phe | Trp | Ile | Tyr | Leu | Arg | His | Val |
| 305 |  |  |  |  | 310 |  |  |  |  | 315 |  |  |  |  | 320 |
| Val | Asn | Ile | Arg | Ile | Leu | Trp | Ser | Val | Leu | Thr | Glu | Phe | Arg | His | Glu |
|  |  |  |  | 325 |  |  |  |  | 330 |  |  |  |  | 335 |  |
| Gly | Asn | Tyr | Val | Leu | Asn | Phe | Ala | Thr | Gln | Gln | Tyr | Lys | Cys | Trp | Ile |
|  |  |  | 340 |  |  |  |  | 345 |  |  |  |  | 350 |  |  |
| Ser | Leu | Pro | Ile | Val | Phe | Val | Leu | Ile | Ala | Ala | Leu | Gln | Leu | Val | Asn |
|  |  | 355 |  |  |  |  | 360 |  |  |  |  | 365 |  |  |  |
| Leu | Tyr | Trp | Leu | Phe | Leu | Ile | Leu | Arg | Ile | Leu | Tyr | Arg | Leu | Ile | Trp |
|  | 370 |  |  |  |  | 375 |  |  |  |  | 380 |  |  |  |  |
| Gln | Gly | Ile | Gln | Lys | Asp | Glu | Arg | Ser | Asp | Ser | Asp | Ser | Asp | Glu | Ser |
| 385 |  |  |  |  | 390 |  |  |  |  | 395 |  |  |  |  | 400 |
| Ala | Glu | Asn | Glu | Glu | Ser | Lys | Glu | Lys | Cys | Glu |
|  |  |  |  | 405 |  |  |  |  | 410 |  |

(2) INFORMATION FOR SEQ ID NO:3:

(i) SEQUENCE CHARACTERISTICS:
        (A) LENGTH: 900 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..654

(xi) SEQUENCE DESCRIPTION: SEQ ID NO:3:

| ATG | TAC | CAT | AGT | GAT | TTG | TGG | TTG | TTC | AAG | ACA | AAA | CCA | ATG | TAC | AGA | 48 |
|---|---|---|---|---|---|---|---|---|---|---|---|---|---|---|---|---|
| Met | Tyr | His | Ser | Asp | Leu | Trp | Leu | Phe | Lys | Thr | Lys | Pro | Met | Tyr | Arg |  |
| 1 |  |  |  | 5 |  |  |  |  | 10 |  |  |  |  | 15 |  |  |
| ACA | TAT | CCT | GTT | ATA | ACC | AAT | CCG | TTC | TTG | TTT | AAG | ATA | TTT | TAC | TTG | 96 |
| Thr | Tyr | Pro | Val | Ile | Thr | Asn | Pro | Phe | Leu | Phe | Lys | Ile | Phe | Tyr | Leu |  |
|  |  |  | 20 |  |  |  |  | 25 |  |  |  |  | 30 |  |  |  |
| GGT | CAA | GCG | GCA | TTT | TGG | GCG | CAA | CAG | GCT | TGT | GTT | CTT | GTT | CTA | CAA | 144 |
| Gly | Gln | Ala | Ala | Phe | Trp | Ala | Gln | Gln | Ala | Cys | Val | Leu | Val | Leu | Gln |  |
|  |  | 35 |  |  |  |  | 40 |  |  |  |  | 45 |  |  |  |  |
| TTA | GAA | AAG | CCA | AGA | AAG | GAT | TAC | AAG | GAA | TTG | GTT | TTT | CAT | CAC | ATT | 192 |
| Leu | Glu | Lys | Pro | Arg | Lys | Asp | Tyr | Lys | Glu | Leu | Val | Phe | His | His | Ile |  |
|  | 50 |  |  |  |  | 55 |  |  |  |  | 60 |  |  |  |  |  |
| GTG | ACA | TTA | TTA | TTA | ATT | TGG | TCA | TCA | TAT | GTT | TTC | CAT | TTT | ACC | AAA | 240 |

| | | | | | | | | | | | | | | | |
|---|---|---|---|---|---|---|---|---|---|---|---|---|---|---|---|
| Val | Thr | Leu | Leu | Leu | Ile | Trp | Ser | Ser | Tyr | Val | Phe | His | Phe | Thr | Lys |
| 65 | | | | | 70 | | | | | 75 | | | | | 80 |

| ATG | GGA | TTG | GCT | ATC | TAT | ATT | ACT | ATG | GAT | GTG | TCA | GAT | TTT | TTC | CTT | 288 |
|---|---|---|---|---|---|---|---|---|---|---|---|---|---|---|---|---|
| Met | Gly | Leu | Ala | Ile | Tyr | Ile | Thr | Met | Asp | Val | Ser | Asp | Phe | Phe | Leu | |
| | | | | 85 | | | | | 90 | | | | | 95 | | |

| TCT | TTG | TCT | AAG | ACA | TTA | AAC | TAT | CTG | AAT | TCT | GTA | TTT | ACT | CCC | TTT | 336 |
|---|---|---|---|---|---|---|---|---|---|---|---|---|---|---|---|---|
| Ser | Leu | Ser | Lys | Thr | Leu | Asn | Tyr | Leu | Asn | Ser | Val | Phe | Thr | Pro | Phe | |
| | | | | 100 | | | | | 105 | | | | | 110 | | |

| GTG | TTC | GGC | TTG | TTC | GTG | TTC | TTT | TGG | ATC | TAT | CTG | CGC | CAT | GTC | GTG | 384 |
|---|---|---|---|---|---|---|---|---|---|---|---|---|---|---|---|---|
| Val | Phe | Gly | Leu | Phe | Val | Phe | Phe | Trp | Ile | Tyr | Leu | Arg | His | Val | Val | |
| | | | 115 | | | | | 120 | | | | | 125 | | | |

| AAT | ATC | AGA | ATA | TTA | TGG | TCA | GTC | TTA | ACA | GAA | TTC | CGT | CAT | GAA | GGT | 432 |
|---|---|---|---|---|---|---|---|---|---|---|---|---|---|---|---|---|
| Asn | Ile | Arg | Ile | Leu | Trp | Ser | Val | Leu | Thr | Glu | Phe | Arg | His | Glu | Gly | |
| | | 130 | | | | | 135 | | | | | 140 | | | | |

| AAT | TAT | GTG | TTG | AAT | TTT | GCC | ACA | CAA | CAA | TAC | AAA | TGT | TGG | ATT | TCG | 480 |
|---|---|---|---|---|---|---|---|---|---|---|---|---|---|---|---|---|
| Asn | Tyr | Val | Leu | Asn | Phe | Ala | Thr | Gln | Gln | Tyr | Lys | Cys | Trp | Ile | Ser | |
| 145 | | | | | 150 | | | | | 155 | | | | | 160 | |

| TTG | CCA | ATT | GTA | TTT | GTA | CTA | ATT | GCT | GCG | TTA | CAA | TTA | GTT | AAC | CTG | 528 |
|---|---|---|---|---|---|---|---|---|---|---|---|---|---|---|---|---|
| Leu | Pro | Ile | Val | Phe | Val | Leu | Ile | Ala | Ala | Leu | Gln | Leu | Val | Asn | Leu | |
| | | | | 165 | | | | | 170 | | | | | 175 | | |

| TAT | TGG | CTG | TTT | TTA | ATT | CTT | AGA | ATC | TTG | TAC | AGA | TTG | ATA | TGG | CAA | 576 |
|---|---|---|---|---|---|---|---|---|---|---|---|---|---|---|---|---|
| Tyr | Trp | Leu | Phe | Leu | Ile | Leu | Arg | Ile | Leu | Tyr | Arg | Leu | Ile | Trp | Gln | |
| | | | 180 | | | | | 185 | | | | | 190 | | | |

| GGT | ATC | CAA | AAG | GAC | GAA | AGA | AGT | GAC | AGT | GAT | TCT | GAT | GAG | AGC | GCT | 624 |
|---|---|---|---|---|---|---|---|---|---|---|---|---|---|---|---|---|
| Gly | Ile | Gln | Lys | Asp | Glu | Arg | Ser | Asp | Ser | Asp | Ser | Asp | Glu | Ser | Ala | |
| | | 195 | | | | | 200 | | | | | 205 | | | | |

| GAA | AAT | GAA | GAA | TCT | AAG | GAA | AAG | TGT | GAA | TAAACGTATC | TTAAGGAGAA | 674 |
|---|---|---|---|---|---|---|---|---|---|---|---|---|
| Glu | Asn | Glu | Glu | Ser | Lys | Glu | Lys | Cys | Glu | | | |
| | 210 | | | | | 215 | | | | | | |

| TACGTATCAT | CATATGATTT | CCCCCCTGTA | TGAAGGCCAA | GTTAACATGG | TATAGCTCAT | 734 |
|---|---|---|---|---|---|---|
| AGTTGTTGTT | ATAAGAAGCA | TAAACCCAAG | TACGAAAGTA | ATAATTCTGT | AAAAAAAAAA | 794 |
| AAAATGCGTT | TATTTAGCGT | CTTCGGGTTG | GCTATATATA | TATATTTAAG | GATATATGGG | 854 |
| CATATGTACA | AGTTTAGGTT | AACAAGCCAA | AAGAAAATAA | AAGTGT | | 900 |

( 2 ) INFORMATION FOR SEQ ID NO:4:

( i ) SEQUENCE CHARACTERISTICS:
        ( A ) LENGTH: 218 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Tyr | His | Ser | Asp | Leu | Trp | Leu | Phe | Lys | Thr | Lys | Pro | Met | Tyr | Arg |
|---|---|---|---|---|---|---|---|---|---|---|---|---|---|---|---|
| 1 | | | | 5 | | | | | 10 | | | | | 15 | |

| Thr | Tyr | Pro | Val | Ile | Thr | Asn | Pro | Phe | Leu | Phe | Lys | Ile | Phe | Tyr | Leu |
|---|---|---|---|---|---|---|---|---|---|---|---|---|---|---|---|
| | | | 20 | | | | | 25 | | | | | 30 | | |

| Gly | Gln | Ala | Ala | Phe | Trp | Ala | Gln | Ala | Cys | Val | Leu | Val | Leu | Gln |
|---|---|---|---|---|---|---|---|---|---|---|---|---|---|---|
| | | | 35 | | | | 40 | | | | | 45 | | |

| Leu | Glu | Lys | Pro | Arg | Lys | Asp | Tyr | Lys | Glu | Leu | Val | Phe | His | His | Ile |
|---|---|---|---|---|---|---|---|---|---|---|---|---|---|---|---|
| | | 50 | | | | | 55 | | | | | 60 | | | |

| Val | Thr | Leu | Leu | Leu | Ile | Trp | Ser | Ser | Tyr | Val | Phe | His | Phe | Thr | Lys |
|---|---|---|---|---|---|---|---|---|---|---|---|---|---|---|---|
| 65 | | | | | 70 | | | | | 75 | | | | | 80 |

| Met | Gly | Leu | Ala | Ile | Tyr | Ile | Thr | Met | Asp | Val | Ser | Asp | Phe | Phe | Leu |
|---|---|---|---|---|---|---|---|---|---|---|---|---|---|---|---|
| | | | | 85 | | | | | 90 | | | | | 95 | |

| Ser | Leu | Ser | Lys | Thr | Leu | Asn | Tyr | Leu | Asn | Ser | Val | Phe | Thr | Pro | Phe |
|---|---|---|---|---|---|---|---|---|---|---|---|---|---|---|---|
| | | | | 100 | | | | | 105 | | | | | 110 | |

```
Val  Phe  Gly  Leu  Phe  Val  Phe  Phe  Trp  Ile  Tyr  Leu  Arg  His  Val  Val
          115                 120                      125

Asn  Ile  Arg  Ile  Leu  Trp  Ser  Val  Leu  Thr  Glu  Phe  Arg  His  Glu  Gly
130                           135                      140

Asn  Tyr  Val  Leu  Asn  Phe  Ala  Thr  Gln  Gln  Tyr  Lys  Cys  Trp  Ile  Ser
145                           150                      155                      160

Leu  Pro  Ile  Val  Phe  Val  Leu  Ile  Ala  Ala  Leu  Gln  Leu  Val  Asn  Leu
                    165                      170                      175

Tyr  Trp  Leu  Phe  Leu  Ile  Leu  Arg  Ile  Leu  Tyr  Arg  Leu  Ile  Trp  Gln
               180                      185                      190

Gly  Ile  Gln  Lys  Asp  Glu  Arg  Ser  Asp  Ser  Asp  Ser  Asp  Glu  Ser  Ala
          195                      200                      205

Glu  Asn  Glu  Glu  Ser  Lys  Glu  Lys  Cys  Glu
210                           215
```

(2) INFORMATION FOR SEQ ID NO:5:

(i) SEQUENCE CHARACTERISTICS:
        (A) LENGTH: 1234 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 656..1234

(xi) SEQUENCE DESCRIPTION: SEQ ID NO:5:

```
CATTGCGTTT  CATTTATGTA  ATTCGAATTT  CTTAACTAAT  CACTAATAAC  GGTAAATGAG    60

GTTAACCATT  AGAATAATGT  ATATAATTAC  GTACAAGGC   TACCGAAGTT  CTGCGGCAGT   120

AATGTAGGGT  TTAGCTTTTG  AATCAATCTT  AGAGCCTGCT  ATCTTCCTGC  ACTTGCTGAT   180

TCCATAAATA  TAAACACCTT  TCGGCTAGAC  CGACAAAGGT  CGTAGTCGTT  TTTCCTTTAG   240

GGTATTATGA  CCAGGGACAC  CCCAGTCCGT  CAAGACTAAT  ATCGATAGTA  TATTACAGGT   300

AAATAGAGAT  CCCTTTTATA  GAGAATTTAA  CGCTTTAAAC  TTACCTAATG  CGTCATCTTC   360

CATTTGAAAT  CCTTCTTGAC  CGAGGGCAGC  CCAGGGGTAG  TGAAAAACGA  TGAAAAAATT   420

CCATTTTTTT  AGCGGGAAAA  GCAAATTGCA  GCATCAACAT  TTTACGCGCT  ATCACTTGAC   480

AAACAAGGCA  AGGAAAACTG  CAGCCCTGTA  CTAAGAAGGT  CAAGATATTT  GCCAAACGAT   540

TTCGTAAGGT  TGTCTCAATT  GATCTGACTG  CTTGTCTATC  TAAAGTGGCA  AGGTATATTA   600

GACAGTGTTG  AGAGTGAACT  CCAAGATACA  GAGAAACTGA  AGAAATAACG  ACAAC ATG    658
                                                                Met
                                                                 1

ACA  TCA  GCT  ACG  GAC  AAA  TCT  ATC  GAT  AGG  TTA  GTT  GTT  AAT  GCA  AAA   706
Thr  Ser  Ala  Thr  Asp  Lys  Ser  Ile  Asp  Arg  Leu  Val  Val  Asn  Ala  Lys
               5                        10                       15

ACA  AGA  AGA  CGA  AAC  TCT  TCC  GTG  GGT  AAA  ATT  GAT  TTA  GGT  GAT  ACA   754
Thr  Arg  Arg  Arg  Asn  Ser  Ser  Val  Gly  Lys  Ile  Asp  Leu  Gly  Asp  Thr
          20                        25                       30

GTT  CCT  GGC  TTT  GCA  GCC  ATG  CCT  GAA  AGT  GCT  GCC  TCT  AAA  AAT  GAG   802
Val  Pro  Gly  Phe  Ala  Ala  Met  Pro  Glu  Ser  Ala  Ala  Ser  Lys  Asn  Glu
     35                        40                       45

GCC  AAA  AAA  AGG  ATG  AAA  GCC  TTG  ACT  GGT  GAC  TCT  AAA  AAG  GAT  AGT   850
Ala  Lys  Lys  Arg  Met  Lys  Ala  Leu  Thr  Gly  Asp  Ser  Lys  Lys  Asp  Ser
50                       55                       60                       65

GAC  CTA  CTG  TGG  AAG  GTT  TGG  TTT  TCA  TAT  AGA  GAA  ATG  AAT  TAC  CGT   898
Asp  Leu  Leu  Trp  Lys  Val  Trp  Phe  Ser  Tyr  Arg  Glu  Met  Asn  Tyr  Arg
```

|     |     |     |     |     | 70  |     |     |     |     | 75  |     |     |     |     | 80  |     |      |
| --- | --- | --- | --- | --- | --- | --- | --- | --- | --- | --- | --- | --- | --- | --- | --- | --- | ---- |
| CAT | AGT | TGG | TTG | ACA | CCA | TTC | TTC | ATA | CTT | GTA | TGC | GTG | TAT | AGC | GCG |     | 946  |
| His | Ser | Trp | Leu | Thr | Pro | Phe | Phe | Ile | Leu | Val | Cys | Val | Tyr | Ser | Ala |     |      |
|     |     |     | 85  |     |     |     |     | 90  |     |     |     |     | 95  |     |     |     |      |
| TAC | TTT | TTA | TCT | GGG | AAT | AGA | ACA | GAA | TCA | AAC | CCG | CTG | CAC | ATG | TTC |     | 994  |
| Tyr | Phe | Leu | Ser | Gly | Asn | Arg | Thr | Glu | Ser | Asn | Pro | Leu | His | Met | Phe |     |      |
|     |     |     | 100 |     |     |     | 105 |     |     |     |     | 110 |     |     |     |     |      |
| GTA | GCC | ATA | TCA | TAT | CAA | GTT | GAT | GGC | ACA | GAC | TCA | TAT | GCA | AAA | GGT |     | 1042 |
| Val | Ala | Ile | Ser | Tyr | Gln | Val | Asp | Gly | Thr | Asp | Ser | Tyr | Ala | Lys | Gly |     |      |
|     | 115 |     |     |     |     | 120 |     |     |     |     | 125 |     |     |     |     |     |      |
| ATC | AAA | GAT | TTG | AGT | TTT | GTG | TTT | TTC | TAC | ATG | ATT | TTC | TTC | ACA | TTT |     | 1090 |
| Ile | Lys | Asp | Leu | Ser | Phe | Val | Phe | Phe | Tyr | Met | Ile | Phe | Phe | Thr | Phe |     |      |
| 130 |     |     |     |     | 135 |     |     |     |     | 140 |     |     |     |     | 145 |     |      |
| TTA | CGT | GAG | TTT | TTG | ATG | GAT | GTT | GTA | ATT | CGA | CCA | TTC | ACG | GTA | TAC |     | 1138 |
| Leu | Arg | Glu | Phe | Leu | Met | Asp | Val | Val | Ile | Arg | Pro | Phe | Thr | Val | Tyr |     |      |
|     |     |     |     | 150 |     |     |     |     | 155 |     |     |     |     | 160 |     |     |      |
| CTA | AAT | GTT | ACT | TCC | GAG | CAT | CGT | CAA | AAG | CGT | ATG | CTA | GAA | CAA | ATG |     | 1186 |
| Leu | Asn | Val | Thr | Ser | Glu | His | Arg | Gln | Lys | Arg | Met | Leu | Glu | Gln | Met |     |      |
|     |     |     | 165 |     |     |     | 170 |     |     |     |     | 175 |     |     |     |     |      |
| TAT | GCC | ATA | TTT | TAT | TGC | GGA | GTT | TCA | GGG | CCC | TTT | GGT | CTT | TAT | ATT |     | 1234 |
| Tyr | Ala | Ile | Phe | Tyr | Cys | Gly | Val | Ser | Gly | Pro | Phe | Gly | Leu | Tyr | Ile |     |      |
|     | 180 |     |     |     |     | 185 |     |     |     |     | 190 |     |     |     |     |     |      |

( 2 ) INFORMATION FOR SEQ ID NO:6:

( i ) SEQUENCE CHARACTERISTICS:
        ( A ) LENGTH: 193 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Thr | Ser | Ala | Thr | Asp | Lys | Ser | Ile | Asp | Arg | Leu | Val | Val | Asn | Ala |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Lys | Thr | Arg | Arg | Arg | Asn | Ser | Ser | Val | Gly | Lys | Ile | Asp | Leu | Gly | Asp |
|     |     |     | 20  |     |     |     |     | 25  |     |     |     |     | 30  |     |     |
| Thr | Val | Pro | Gly | Phe | Ala | Ala | Met | Pro | Glu | Ser | Ala | Ala | Ser | Lys | Asn |
|     |     | 35  |     |     |     |     | 40  |     |     |     |     | 45  |     |     |     |
| Glu | Ala | Lys | Lys | Arg | Met | Lys | Ala | Leu | Thr | Gly | Asp | Ser | Lys | Lys | Asp |
|     | 50  |     |     |     |     | 55  |     |     |     |     | 60  |     |     |     |     |
| Ser | Asp | Leu | Leu | Trp | Lys | Val | Trp | Phe | Ser | Tyr | Arg | Glu | Met | Asn | Tyr |
| 65  |     |     |     |     | 70  |     |     |     |     | 75  |     |     |     |     | 80  |
| Arg | His | Ser | Trp | Leu | Thr | Pro | Phe | Phe | Ile | Leu | Val | Cys | Val | Tyr | Ser |
|     |     |     |     | 85  |     |     |     |     | 90  |     |     |     |     | 95  |     |
| Ala | Tyr | Phe | Leu | Ser | Gly | Asn | Arg | Thr | Glu | Ser | Asn | Pro | Leu | His | Met |
|     |     |     | 100 |     |     |     |     | 105 |     |     |     |     | 110 |     |     |
| Phe | Val | Ala | Ile | Ser | Tyr | Gln | Val | Asp | Gly | Thr | Asp | Ser | Tyr | Ala | Lys |
|     |     | 115 |     |     |     |     | 120 |     |     |     |     | 125 |     |     |     |
| Gly | Ile | Lys | Asp | Leu | Ser | Phe | Val | Phe | Phe | Tyr | Met | Ile | Phe | Phe | Thr |
|     | 130 |     |     |     |     | 135 |     |     |     |     | 140 |     |     |     |     |
| Phe | Leu | Arg | Glu | Phe | Leu | Met | Asp | Val | Val | Ile | Arg | Pro | Phe | Thr | Val |
| 145 |     |     |     |     | 150 |     |     |     |     | 155 |     |     |     |     | 160 |
| Tyr | Leu | Asn | Val | Thr | Ser | Glu | His | Arg | Gln | Lys | Arg | Met | Leu | Glu | Gln |
|     |     |     |     | 165 |     |     |     |     | 170 |     |     |     |     | 175 |     |
| Met | Tyr | Ala | Ile | Phe | Tyr | Cys | Gly | Val | Ser | Gly | Pro | Phe | Gly | Leu | Tyr |
|     |     |     | 180 |     |     |     |     | 185 |     |     |     |     | 190 |     |     |
| Ile |     |     |     |     |     |     |     |     |     |     |     |     |     |     |     |

(2) INFORMATION FOR SEQ ID NO:7:

(i) SEQUENCE CHARACTERISTICS:
        (A) LENGTH: 655 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

```
CATTGCGTTT   CATTTATGTA   ATTCGAATTT   CTTAACTAAT   CACTAATAAC   GGTAAATGAG    60
GTTAACCATT   AGAATAATGT   ATATAATTAC   GTACAAAGGC   TACCGAAGTT   CTGCGGCAGT   120
AATGTAGGGT   TTAGCTTTTG   AATCAATCTT   AGAGCCTGCT   ATCTTCCTGC   ACTTGCTGAT   180
TCCATAAATA   TAAACACCTT   TCGGCTAGAC   CGACAAAGGT   CGTAGTCGTT   TTTCCTTTAG   240
GGTATTATGA   CCAGGGACAC   CCCAGTCCGT   CAAGACTAAT   ATCGATAGTA   TATTACAGGT   300
AAATAGAGAT   CCCTTTTATA   GAGAATTTAA   CGCTTTAAAC   TTACCTAATG   CGTCATCTTC   360
CATTTGAAAT   CCTTCTTGAC   CGAGGGCAGC   CCAGGGGTAG   TGAAAAACGA   TGAAAAAATT   420
CCATTTTTTT   AGCGGGAAAA   GCAAATTGCA   GCATCAACAT   TTTACGCGCT   ATCACTTGAC   480
AAACAAGGCA   AGGAAAACTG   CAGCCCTGTA   CTAAGAAGGT   CAAGATATTT   GCCAAACGAT   540
TTCGTAAGGT   TGTCTCAATT   GATCTGACTG   CTTGTCTATC   TAAAGTGGCA   AGGTATATTA   600
GACAGTGTTG   AGAGTGAACT   CCAAGATACA   GAGAAACTGA   AGAAATAACG   ACAAC        655
```